United States Patent
Maillard et al.

(10) Patent No.: US 10,053,434 B2
(45) Date of Patent: Aug. 21, 2018

(54) HISTONE DEACETYLASE INHIBITORS AND COMPOSITIONS AND METHODS OF USE THEREOF

(71) Applicant: CHDI Foundation, Inc., New York, NY (US)

(72) Inventors: Michel C. Maillard, Playa Vista, CA (US); Perla Breccia, Saffron Walden (GB); Celia Dominguez, Los Angeles, CA (US); Alan F. Haughan, Saffron Walden (GB); Amanda Van de Poël, Saffron Walden (GB); Andrew J. Stott, Saffron Walden (GB); Christopher A. Luckhurst, Saffron Walden (GB); Elizabeth A. Saville-Stones, Saffron Walden (GB); Grant Wishart, Saffron Walden (GB); Michael Wall, Saffron Walden (GB); Rebecca E. Jarvis, Saffron Walden (GB)

(73) Assignee: CHDI FOUNDATION, INC., New York, NY (US)

( * ) Notice: Subject to any disclaimer, the term of this patent is extended or adjusted under 35 U.S.C. 154(b) by 0 days.

(21) Appl. No.: 15/148,907

(22) Filed: May 6, 2016

(65) Prior Publication Data

US 2016/0326124 A1    Nov. 10, 2016

Related U.S. Application Data

(60) Provisional application No. 62/158,363, filed on May 7, 2015.

(51) Int. Cl.
| | | |
|---|---|---|
| *C07D 413/12* | (2006.01) | |
| *C07D 271/06* | (2006.01) | |
| *C07D 471/04* | (2006.01) | |

(52) U.S. Cl.
CPC .......... *C07D 271/06* (2013.01); *C07D 413/12* (2013.01); *C07D 471/04* (2013.01)

(58) Field of Classification Search
CPC ... C07D 413/12; C07D 271/06; C07D 471/04
See application file for complete search history.

(56) References Cited

U.S. PATENT DOCUMENTS

| | | |
|---|---|---|
| 9,056,843 B2 | 6/2015 | Hebach et al. |
| 2009/0048228 A1 | 2/2009 | Attenni et al. |
| 2015/0057238 A1 | 2/2015 | Toledo-Sherman et al. |
| 2016/0333001 A1 | 11/2016 | Dominguez et al. |

FOREIGN PATENT DOCUMENTS

| | | | |
|---|---|---|---|
| CA | | 2841113 A1 * | 1/2013 |
| WO | WO 2011/088181 A1 | | 7/2011 |
| WO | WO-2013/006408 A1 | | 1/2013 |
| WO | WO 2013/008162 A1 | | 1/2013 |
| WO | WO 2013/009810 A1 | | 1/2013 |
| WO | WO-2013/009830 A1 | | 1/2013 |
| WO | WO-2013/033085 A1 | | 3/2013 |
| WO | WO 2013/080120 A1 | | 6/2013 |
| WO | WO 2017/018803 A1 | | 2/2017 |
| WO | WO 2017/018805 A1 | | 2/2017 |
| WO | WO 2017/023133 A2 | | 2/2017 |

OTHER PUBLICATIONS

International Search Report and Written Opinion for PCT/ US16/31335 dated Jul. 29, 2016, 9 pages.
International Search Report and Written Opinion dated Aug. 11, 2016 for PCT/US2016/031329, 9 pages.
Lobera, et al. Selective class IIa histone deacetylase inhibition via a nonchelating zinc-binding group. Nat Chem Biol. May 2013;9(5):319-25. doi: 10.1038/nchembio.1223. Epub Mar. 24, 2013.

* cited by examiner

*Primary Examiner* — Laura L. Stockton
(74) *Attorney, Agent, or Firm* — Sheppard Mullin Richter & Hampton LLP

(57) ABSTRACT

Provided are certain histone deacetylase (HDAC) inhibitors of Formula I, compositions thereof, and methods of their use.

Formula I

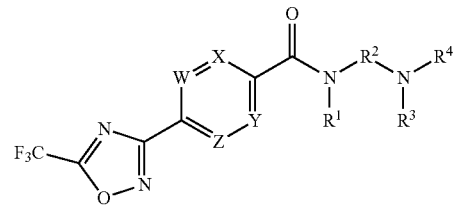

36 Claims, No Drawings

HISTONE DEACETYLASE INHIBITORS AND COMPOSITIONS AND METHODS OF USE THEREOF

CROSS-REFERENCE TO RELATED APPLICATIONS

This application claims the benefit under 35 U.S.C. § 119(e) of U.S. Provisional Application 62/158,363, filed on May 7, 2015, which is hereby incorporated by reference in its entirety.

FIELD

Provided herein are certain histone deacetylase (HDAC) inhibitors, compositions thereof, and methods of their use.

BACKGROUND

Histone deacetylases (HDACs) are zinc-containing enzymes which catalyze the removal of acetyl groups from the ε-amino termini of lysine residues clustered near the amino terminus of nucleosomal histones. There are 11 known metal-dependent human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to Class IIa and have homology to yeast HDAC1. HDAC6 and HDAC10 contain two catalytic sites and are classified as Class IIb, whereas HDAC11 has conserved residues in its catalytic center that are shared by both Class I and Class II deacetylases and is sometimes placed in Class IV.

SUMMARY

Provided is a compound of Formula I:

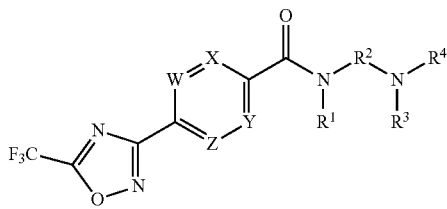

Formula I or a pharmaceutically acceptable salt, an optical isomer, or a mixture of optical isomers thereof;
wherein:
W is N or $CR^5$; X is N or $CR^6$; Y is N or $CR^7$; and Z is N or $CR^8$; provided not more than two of W, X, Y, and Z are N;
$R^1$ is selected from H and $C_1$-$C_3$ alkyl;
$R^2$ is $C_2$-$C_3$ alkylene optionally substituted with $C_1$-$C_2$ haloalkyl or 3 or 4-membered cycloalkyl;
$R^3$ and $R^4$, together with the nitrogen atom to which they are attached, form:
  a 4, 5, 6, or 7-membered heteromonocyclic group, or
  a 6, 7, 8, 9, or 10-membered heterobicyclic group,
  each of which is optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo,
provided that if $R^3$ and $R^4$, together with the nitrogen atom to which they are attached,
form a 5 or 6-membered heteromonocyclic group, then:
  i) $R^2$ is $C_2$-$C_3$ alkylene substituted with $C_1$-$C_2$ haloalkyl or 3 or 4-membered cycloalkyl, or
  ii) $R^8$ is halo or $C_1$-$C_3$ alkyl, or
  iii) the 5 or 6-membered heteromonocyclic group is substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo; and
$R^5$, $R^6$, $R^7$ and $R^8$ are each independently selected from H, $C_1$-$C_4$ alkyl, $C_1$-$C_4$ haloalkyl, and halo.

Also provided is a pharmaceutical composition comprising a compound, or a pharmaceutically acceptable salt thereof, described herein and a pharmaceutically acceptable carrier.

Also provided is a process for preparing a pharmaceutical composition comprising admixing a compound, or a pharmaceutically acceptable salt thereof, described herein and a pharmaceutically acceptable carrier.

Also provided is a method for treating a condition or disorder mediated by at least one histone deacetylase in a patient in need thereof comprising administering to the patient a therapeutically effective amount of a compound, or a pharmaceutically acceptable salt thereof, described herein.

DETAILED DESCRIPTION

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses a straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkylene" encompasses straight chain and branched chain di-radical having the indicated number of carbon atoms, usually from 1 to 20 carbon atoms, for example 1 to 8 carbon atoms, such as 1 to 6 carbon atoms, or 1 to 4 carbon atoms. Examples of $C_1$-$C_4$ alkylene include methylene, 1,1-ethyene, 1,2-ethylene, 1,1-propylene, 1,2-propylene, 1,3-propylene, 1,1-butylene, 1,2-butylene, 1,3-butylene, 1,4-butylene, 2-methyl-1,2-propylene, and 2-methyl-1,3-propylene.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Carboxy" indicates —C(O)OH.

"Cyano" refers to —CN.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged, spirocyclic, and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group, i.e., it is considered an aryl group.

The term "cycloalkoxy" refers to "—O-cycloalkyl," wherein cycloalkyl is as defined herein.

The term "halo" includes fluoro, chloro, bromo, and iodo, and the term "halogen" includes fluorine, chlorine, bromine, and iodine.

The term "haloalkyl" denotes an $C_{1-6}$ alkyl group wherein the alkyl is substituted with one halogen up to fully substituted and a fully substituted $C_{1-6}$ haloalkyl can be represented by the formula $C_nL_{2n+1}$ wherein L is a halogen and "n" is 1, 2, 3 or 4; when more than one halogen is present then they may be the same or different and selected from the group consisting of F, Cl, Br and I, such as F. Examples of $C_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "haloalkoxy" denotes a haloalkyl which is directly attached to an oxygen atom. Examples include, but not limited to, difluoromethoxy, trifluoromethoxy, 2,2,2-trifluoroethoxy, pentafluoroethoxy and the like.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon.

Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic (i.e., heteromonocyclic) or polycyclic (e.g., bicyclic (i.e., heterobicyclic), including spirocyclic and bridged ring systems). That is, the definition of heterobicyclic encompasses a heteromonocyclic ring 1,1-disubstituted with a cycloalkyl or heteromonocyclic group, as well as a ring system wherein a heteromonocyclic ring is 1,2- or 1,3-fused to another cycloalkyl or heteromonocyclic ring (where a carbon or nitrogen atom can form the ring junction (where the structure is chemically feasible)), as well as a ring system wherein a heteromonocyclic ring has a $C_1$-$C_2$ alkyl bridge, as well as a ring system wherein a heteromonocyclic ring is 1,2-fused to an aromatic or heteroaromatic ring, provided that the moiety is bound to the parent structure via a non-aromatic carbon or nitrogen atom.

Examples of monocyclic heterocycloalkyl (i.e., heteromonocyclic) groups include oxiranyl, aziridinyl, azetidinyl, oxetanyl, pyrrolidinyl, imidazolidinyl, pyrazolidinyl, piperidinyl, piperazinyl, morpholinyl and thiomorpholinyl.

Examples of a $C_6$ heterobicyclyl group include 3-azabicyclo[3.1.0]hexan-3-yl.

Examples of a $C_8$-$C_{10}$ heterobicyclyl group having an aromatic ring include indolin-1-yl, isoindolin-2-yl, 1,2,3,4-tetrahydroquinolin-2-yl, 3,4-dihydroquinolin-1(2H)-yl, and 7,8-dihydro-1,6-naphthyridin-6(5H)-yl.

Examples of heterobicyclyl ring systems including a spirocycle include: 1-oxa-5-azaspiro[3.3]heptan-5-yl, 1-oxa-6-azaspiro[3.3]heptan-6-yl, 6-oxa-1-azaspiro[3.3]heptan-1-yl, 2-oxa-6-azaspiro[3.3]heptan-6-yl, 1,5-diazaspiro[3.3]heptan-1-yl, 1,6-diazaspiro[3.3]heptan-6-yl, 1,6-diazaspiro[3.3]heptan-1-yl, 2,6-diazaspiro[3.3]heptan-2-yl, 1-oxa-5-azaspiro[3.4]octan-5-yl, 1-oxa-6-azaspiro[3.4]octan-6-yl, 2-oxa-5-azaspiro[3.4]octan-5-yl, 2-oxa-6-azaspiro[3.4]octan-6-yl, 1,5-diazaspiro[3.4]octan-5-yl, 1,6-diazaspiro[3.4]octan-6-yl, 2,5-diazaspiro[3.4]octan-5-yl, 2,6-diazaspiro[3.4]octan-6-yl, 1-oxa-5-azaspiro[3.5]nonan-5-yl, 1-oxa-6-azaspiro[3.5]nonan-6-yl, 1-oxa-7-azaspiro[3.5]nonan-7-yl, 2-oxa-5-azaspiro[3.5]nonan-5-yl, 2-oxa-6-azaspiro[3.5]nonan-6-yl, 2-oxa-7-azaspiro[3.5]nonan-7-yl, 1,5-diazaspiro[3.5]nonan-5-yl, 1,6-diazaspiro[3.5]nonan-6-yl, 1,7-diazaspiro[3.5]nonan-7-yl, 2,5-diazaspiro[3.5]nonan-5-yl, 2,6-diazaspiro[3.5]nonan-6-yl, 2,7-diazaspiro[3.5]nonan-7-yl, 1-oxa-5-azaspiro[3.6]decan-5-yl, 1-oxa-6-azaspiro[3.6]decan-6-yl, 1-oxa-7-azaspiro[3.6]decan-7-yl, 2-oxa-5-azaspiro[3.6]decan-5-yl, 2-oxa-6-azaspiro[3.6]decan-6-yl, 2-oxa-7-azaspiro[3.6]decan-7-yl, 1,5-diazaspiro[3.6]decan-5-yl, 1,6-diazaspiro[3.6]decan-6-yl, 1,7-diazaspiro[3.6]decan-7-yl 2,5-diazaspiro[3.6]decan-5-yl, 2,6-diazaspiro[3.6]decan-6-yl, 2,7-diazaspiro[3.6]decan-7-yl.

Examples of heterobicyclyl ring systems including a $C_1$-$C_4$ bridged-alkylene include 2-azabicyclo[2.2.1]heptan-2-yl, 2-azabicyclo[3.2.1]octan-2-yl, 3-azabicyclo[3.2.1]octan-3-yl, and 6-azabicyclo[3.2.1]octan-6-yl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

"Oxo" refers to (=O) or (O).

"Nitro" refers to —$NO_2$.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, —$O(C_1$-$C_2$ alkyl) O— (e.g., methylenedioxy-), —$SR^b$, guanidine (—NHC(=NH)$NH_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) or supercritical fluid chromatograph (SFC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

Where a configuration of a single diastereomer is not known the configuration has been denoted, for example, as D1 (diastereomer 1) and D2 (diastereomer 2) and the unknown chiral center(s) labeled with an asterisk. For example, D1 N—((R)-1-((abs)-3-(difluoromethoxy)piperidin-1-yl)propan-2-yl)-4-(5-(trifluoromethyl)-1,2,4-oxadiazol-3-yl)benzamide and D2 N—((R)-1-((abs)-3-(difluoromethoxy)piperidin-1-yl)propan-2-yl)-4-(5-(trifluoromethyl)-1,2,4-oxadiazol-3-yl)benzamide are single diastereomers for which the configuration at one chiral center is known absolutely (with configuration drawn accordingly) and the configuration at the second chiral center is absolute but unknown (drawn as a bond with an asterisk), i.e. opposite configuration at the unknown center for D1 versus D2.

Where a single isomer has been isolated for a compound with three chiral centers where one stereocenter is known, and the absolute configuration of the other two centers are unknown but the relative configuration known to be cis, e.g. a homochiral azabicycloheptanyl ring system, the compound has been drawn where the unknown chiral center(s) are labeled with an asterisk, and named accordingly, i.e. D1: N—((R)-1-((abs-1,5-cis)-6-azabicyclo[3.2.0]heptan-6-yl)propan-2-yl)-4-(5-(trifluoromethyl)-1,2,4-oxadiazol-3-yl)benzamide; and D2: N—((R)-1-((abs-1,5-cis)-6-azabicyclo[3.2.0]heptan-6-yl)propan-2-yl)-4-(5-(trifluoromethyl)-1,2,4-oxadiazol-3-yl)benzamide.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_q$—COOH where q is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic free base or non-toxic pharmaceutically acceptable addition salts.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of HDAC activity.

As used herein, the terms "histone deacetylase" and "HDAC" are intended to refer to any one of a family of enzymes that remove $N^\epsilon$-acetyl groups from the ε-amino groups of lysine residues of a protein (for example, a histone, or tubulin). Unless otherwise indicated by context, the term "histone" is meant to refer to any histone protein, including H1, H2A, H2B, H3, H4, and H5, from any species. In some embodiments, the histone deacetylase is a human HDAC, including, but not limited to, HDAC-4, HDAC-5, HDAC-6, HDAC-7, HDAC-9, and HDAC-10. In some embodiments, at least one histone deacetylase is selected from HDAC-4, HDAC-5, HDAC-7, and HDAC-9. In some embodiments, the histone deacetylase is a class IIa HDAC. In some embodiments, the histone deacetylase is HDAC-4. In some embodiments, the histone deacetylase is HDAC-5. In some embodiments, the histone deacetylase is derived from a protozoal or fungal source.

The terms "histone deacetylase inhibitor" and "inhibitor of histone deacetylase" are intended to mean a compound, or a pharmaceutically acceptable salt thereof, described herein which is capable of interacting with a histone deacetylase and inhibiting its enzymatic activity.

The term "a condition or disorder mediated by HDAC" or "a condition or disorder mediated by histone deacetylase" as used herein refers to a condition or disorder in which HDAC and/or the action of HDAC is important or necessary, e.g., for the onset, progress, expression, etc. of that condition, or a condition which is known to be treated by HDAC inhibitors (such as, trichostatin A).

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "inhibiting histone deacetylase enzymatic activity" or "inhibiting histone deacetylase" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some embodiments, such reduction of histone deacetylase activity is at least 50%, such as at least about 75%, for example, at least about 90%. In some embodiments, histone deacetylase activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

In some embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. In some embodiments, the concentration of the inhibitor required for histone deacetylase inhibitory activity is at least 2-fold lower, such as at least 5-fold lower, for example, at least 10-fold lower, such as at least 20-fold lower than the concentration required to produce an unrelated biological effect.

"Treatment" or "treating" means any treatment of a disease state in a patient, including
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I, are specifically embraced by herein just as if each and every combination was individually and explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, such as those conditions or disorders mediated by HDAC, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

Provided is a compound of Formula I:

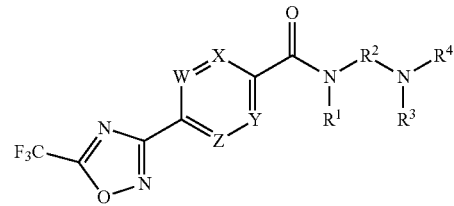

Formula I or a pharmaceutically acceptable salt thereof;
wherein:
W is N or $CR^5$; X is N or $CR^6$; Y is N or $CR^7$; and Z is N or $CR^8$; provided not more than two of W, X, Y, and Z are N;
$R^1$ is selected from H and $C_1$-$C_3$ alkyl;
$R^2$ is $C_2$-$C_3$ alkylene optionally substituted with $C_1$-$C_2$ haloalkyl or 3 or 4-membered cycloalkyl;
$R^3$ and $R^4$, together with the nitrogen atom to which they are attached, form:
  a 4, 5, 6, or 7-membered heteromonocyclic group, or
  a 6, 7, 8, 9, or 10-membered heterobicyclic group,
  each of which is optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo,
provided that if $R^3$ and $R^4$, together with the nitrogen atom to which they are attached, form a 5 or 6-membered heteromonocyclic group, then:
i) $R^2$ is $C_2$-$C_3$ alkylene substituted with $C_1$-$C_2$ haloalkyl or 3 or 4-membered cycloalkyl, or
ii) $R^8$ is halo or $C_1$-$C_3$ alkyl, or
iii) the 5 or 6-membered heteromonocyclic group is substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo; and
$R^5$, $R^6$, $R^7$ and $R^8$ are each independently selected from H, $C_1$-$C_4$ alkyl, $C_1$-$C_4$ haloalkyl, and halo.

In some embodiments, $R^1$ is selected from H and methyl. In some embodiments, $R^1$ is H.

In some embodiments, $R^2$ is $C_2$-$C_3$ alkylene optionally substituted with 3 or 4-membered cycloalkyl. In some embodiments, $R^2$ is chosen from —$(CH_2)_2$— and —CH$(CH_3)CH_2$—.

In some embodiments, $R^5$ is H.
In some embodiments, $R^6$ is H.
In some embodiments, $R^7$ is H.
In some embodiments, $R^8$ is selected from H, halo, and methyl.

In some embodiments, $R^3$ and $R^4$, together with the nitrogen atom to which they are attached, form a 4 or 7-membered heteromonocyclic group optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 4 or 7-membered heteromonocyclic group optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, aryl, and heteroaryl, wherein aryl and heteroaryl are optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 4 or 7-membered heteromonocyclic group optionally substituted with one to five substituents each independently selected from: $C_1$-$C_3$ alkyl, $C_1$-$C_3$ haloalkoxy, and aryl, wherein aryl is optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 4 or 7-membered heteromonocyclic group optionally substituted with one to five substituents each independently selected from: $C_1$-$C_3$ alkyl, $C_1$-$C_3$ haloalkoxy, and phenyl, wherein phenyl is optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 4 or 7-membered heteromonocyclic group optionally substituted with one to five substituents each independently selected from: methyl, difluoromethoxy, and phenyl.

In some embodiments, $R^3$ and $R^4$, together with the nitrogen atom to which they are attached, form a 4 or 7-membered heteromonocyclic group selected from 3-phenylazetidin-1-yl, and azepan-1-yl.

In some embodiments, $R^3$ and $R^4$, together with the nitrogen atom to which they are attached, form a 5 or 6-membered heteromonocyclic group and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, aryl, and heteroaryl, wherein aryl and heteroaryl are optionally further substituted with one to five substituents each independently selected from $C_1$-$C_3$ alkyl, $C_1$-$C_3$ haloalkyl, and halo and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkyl, $C_1$-$C_3$ haloalkoxy, and aryl, wherein aryl is optionally further substituted with one to five substituents each independently selected from $C_1$-$C_3$ alkyl, $C_1$-$C_3$ haloalkyl, and halo and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkyl, $C_1$-$C_3$ haloalkoxy, and phenyl, wherein phenyl is optionally further substituted with one to five substituents each independently selected from $C_1$-$C_3$ alkyl, $C_1$-$C_3$ haloalkyl, and halo and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group optionally substituted with one to five substituents each independently selected from: methyl, difluoromethoxy, and phenyl and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group selected from pyrrolidin-1-yl, and piperidin-1-yl, each of which is optionally substituted with one substituent selected from: methyl, difluoromethoxy, and phenyl and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group selected from pyrrolidin-1-yl, 2-methyl-pyrrolidin-1-yl, and 3-(difluoromethoxy)piperidin-1-yl and $R^2$ is $C_2$-$C_3$ alkylene substituted with $C_1$-$C_2$ haloalkyl or 3 or 4-membered cycloalkyl, such as $R^2$ is $C_2$-$C_3$ alkylene substituted with cyclopropyl.

In some embodiments, $R^3$ and $R^4$, together with the nitrogen atom to which they are attached, form a 5 or 6-membered heteromonocyclic group and $R^8$ is halo or $C_1$-$C_3$ alkyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo and $R^8$ is halo or $C_1$-$C_3$ alkyl, e.g., methyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, aryl, and heteroaryl, wherein aryl and heteroaryl are optionally further substituted with one to five substituents each independently selected from $C_1$-$C_3$ alkyl, $C_1$-$C_3$ haloalkyl, and halo and $R^8$ is halo or $C_1$-$C_3$ alkyl, e.g., methyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkyl, $C_1$-$C_3$ haloalkoxy, and aryl, wherein aryl is optionally further substituted with one to five substituents each independently selected from $C_1$-$C_3$ alkyl, $C_1$-$C_3$ haloalkyl, and halo and $R^8$ is halo or $C_1$-$C_3$ alkyl, e.g., methyl.

In some embodiments, $R^3$ and $R^4$, together with the nitrogen atom to which they are attached, form a 5 or 6-membered heteromonocyclic group optionally substituted with one to five substituents each independently selected from: $C_1$-$C_3$ alkyl, $C_1$-$C_3$ haloalkoxy, and phenyl, wherein phenyl is optionally further substituted with one to five substituents each independently selected from $C_1$-$C_3$ alkyl, $C_1$-$C_3$ haloalkyl, and halo and $R^8$ is halo or $C_1$-$C_3$ alkyl, e.g., methyl.

In some embodiments, $R^3$ and $R^4$, together with the nitrogen atom to which they are attached, form a 5 or 6-membered heteromonocyclic group optionally substituted with one to five substituents each independently selected from: methyl, difluoromethoxy, and phenyl and $R^8$ is halo or $C_1$-$C_3$ alkyl, e.g., methyl.

In some embodiments, $R^3$ and $R^4$, together with the nitrogen atom to which they are attached, form a 5 or 6-membered heteromonocyclic group selected from pyrrolidin-1-yl, and piperidin-1-yl, each of which is optionally substituted with one substituent selected from: methyl, difluoromethoxy, and phenyl and $R^8$ is halo or $C_1$-$C_3$ alkyl, e.g., methyl.

In some embodiments, $R^3$ and $R^4$, together with the nitrogen atom to which they are attached, form a 5 or 6-membered heteromonocyclic group selected from pyrrolidin-1-yl, 2-methyl-pyrrolidin-1-yl, and 3-(difluoromethoxy)piperidin-1-yl and $R^8$ is halo or $C_1$-$C_3$ alkyl, e.g., methyl.

In some embodiments, $R^3$ and $R^4$, together with the nitrogen atom to which they are attached, form a 5 or 6-membered heteromonocyclic group substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 5 or 6-membered heteromonocyclic group substituted with one to five substituents each independently selected from: $C_1$-$C_3$ alkyl, $C_1$-$C_3$ haloalkoxy, and aryl, wherein aryl is optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 5 or 6-membered heteromonocyclic group substituted with one to five substituents each independently selected from: $C_1$-$C_3$ alkyl, $C_1$-$C_3$ haloalkoxy, and phenyl, wherein phenyl is optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 5 or 6-membered heteromonocyclic group substituted with one to five substituents each independently selected from: methyl, difluoromethoxy, and phenyl.

In some embodiments, $R^3$ and $R^4$, together with the nitrogen atom to which they are attached, form a 5 or 6-membered heteromonocyclic group selected from pyrrolidin-1-yl, and piperidin-1-yl, each of which is substituted with one substituent selected from: methyl, difluoromethoxy, and phenyl.

In some embodiments, $R^3$ and $R^4$, together with the nitrogen atom to which they are attached, form a 5 or 6-membered heteromonocyclic group selected from 2-methyl-pyrrolidin-1-yl, and 3-(difluoromethoxy)piperidin-1-yl.

In some embodiments, $R^3$ and $R^4$, together with the nitrogen atom to which they are attached, form a (2S)-methyl-pyrrolidin-1-yl.

In some embodiments, $R^3$ and $R^4$, together with the nitrogen atom to which they are attached, form a 6, 7, 8, 9, or 10-membered heterobicyclic group, which is optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 6, 7, 8, 9, or 10-membered heterobicyclic group selected from:
1-azaspiro[3.3]heptan-1-yl,
3-azabicyclo[3.1.0]hexan-3-yl,
3-azabicyclo[3.2.0]heptan-3-yl,
3-azabicyclo[3.2.1]heptan-3-yl,
3-azabicyclo[3.2.1]octan-3-yl,
3,4-dihydroisoquinolin-2(1H)-yl,
3,4-dihydro-2,7-naphthyridin-2(1H)-yl,
5-azaspiro[2.4]heptan-5-yl,
5-azaspiro[2.5]octan-5-yl,
6-azaspiro[2.5]octan-6-yl,
1-azaspiro[3.3]heptan-1-yl,
6-azabicyclo[3.2.0]heptan-6-yl,
isoindolin-2-yl, and
octahydrocyclopenta[c]pyrrol-2-yl, and
  each of which is optionally substituted with one to five substituents each independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from $C_1$-$C_3$ alkyl, $C_1$-$C_3$ haloalkyl, and halo.

In some embodiments, $R^3$ and $R^4$, together with the nitrogen atom to which they are attached, form a 6, 7, 8, 9, or 10-membered heterobicyclic group selected from:
1-azaspiro[3.3]heptan-1-yl,
3-azabicyclo[3.1.0]hexan-3-yl,
3-azabicyclo[3.2.0]heptan-3-yl,
3-azabicyclo[3.2.1]heptan-3-yl,
3-azabicyclo[3.2.1]octan-3-yl,
3,4-dihydroisoquinolin-2(1H)-yl,
3,4-dihydro-2,7-naphthyridin-2(1H)-yl,
5-azaspiro[2.4]heptan-5-yl,
5-azaspiro[2.5]octan-5-yl,
6-azaspiro[2.5]octan-6-yl,
1-azaspiro[3.3]heptan-1-yl,
6-azabicyclo[3.2.0]heptan-6-yl,
isoindolin-2-yl, and
octahydrocyclopenta[c]pyrrol-2-yl, and
  each of which is optionally substituted with one or two substituents each independently selected from: $C_1$-$C_3$ alkoxy, $C_1$-$C_3$ alkyl, $C_1$-$C_3$ haloalkoxy, $C_1$-$C_3$ haloalkyl, and carboxy.

In some embodiments, $R^3$ and $R^4$, together with the nitrogen atom to which they are attached, form a 6, 7, 8, 9, or 10-membered heterobicyclic group selected from:
1-azaspiro[3.3]heptan-1-yl,
3-azabicyclo[3.1.0]hexan-3-yl,
3-azabicyclo[3.2.0]heptan-3-yl,
3-azabicyclo[3.2.1]heptan-3-yl,
3-azabicyclo[3.2.1]octan-3-yl,
3,4-dihydroisoquinolin-2(1H)-yl,
3,4-dihydro-2,7-naphthyridin-2(1H)-yl,
5-azaspiro[2.4]heptan-5-yl,
5-azaspiro[2.5]octan-5-yl,
6-azaspiro[2.5]octan-6-yl,
1-azaspiro[3.3]heptan-1-yl,
6-azabicyclo[3.2.0]heptan-6-yl,
isoindolin-2-yl, and
octahydrocyclopenta[c]pyrrol-2-yl, and
  each of which is optionally substituted with one or two substituents each independently selected from $C_1$-$C_3$ alkyl.

Also provided is a compound of Formula II, or a pharmaceutically acceptable salt thereof,

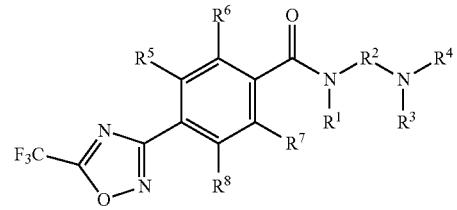

Formula II wherein $R^1$, $R^2$, $R^3$, $R^4$, $R^5$, $R^6$, $R^7$, and $R^8$ are as described herein.

Also provided is a compound of Formula III, or a pharmaceutically acceptable salt thereof,

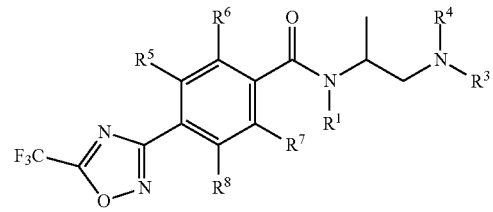

Formula III wherein $R^1$, $R^3$, $R^4$, $R^5$, $R^6$, $R^7$, and $R^8$ are as described herein.

Also provided is a compound of Formula IV, or a pharmaceutically acceptable salt thereof, of Formula VI, or a pharmaceutically acceptable salt thereof,

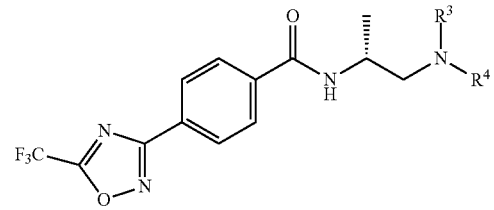

Formula IV wherein $R^3$ and $R^4$ are as described herein.

Also provided is a compound of Formula V, or a pharmaceutically acceptable salt thereof,

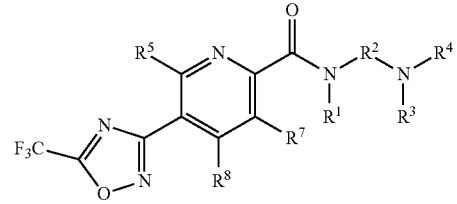

Formula V wherein $R^1$, $R^2$, $R^3$, $R^4$, $R^5$, $R^7$, and $R^8$ are as described herein.

Also provided is a compound of Formula VI, or a pharmaceutically acceptable salt thereof, Formula VI

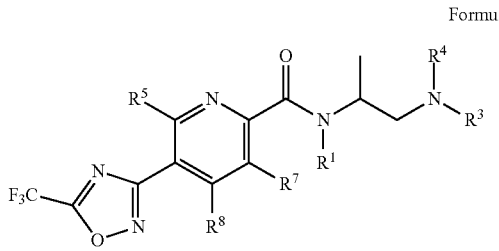

wherein $R^1$, $R^3$, $R^4$, $R^5$, $R^7$, and $R^8$ are as described herein.

Also provided is a compound of Formula VII, or a pharmaceutically acceptable salt thereof, Formula VII

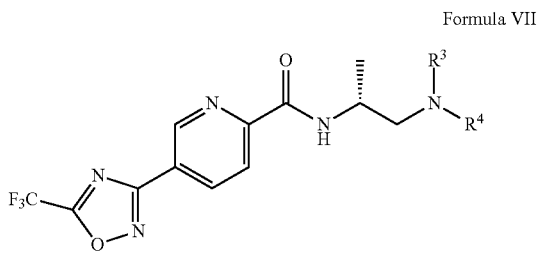

wherein $R^3$ and $R^4$ are as described herein.

Also provided is a compound selected from:
(2S)-2-Methyl-1-((R)-2-(3-methyl-4-(5-(trifluoromethyl)-1,2,4-oxadiazol-3-yl)benzamido)propyl)pyrrolidin-1-ium formate;
N-(2-(3-Azabicyclo[3.2.1]octan-3-yl)ethyl)-4-(5-(trifluoromethyl)-1,2,4-oxadiazol-3-yl)benzamide;
(R)—N-(1-(Isoindolin-2-yl)propan-2-yl)-4-(5-(trifluoromethyl)-1,2,4-oxadiazol-3-yl)benzamide;
N-((2R)-1-(3-Azabicyclo[3.1.0]hexan-3-yl)propan-2-yl)-4-(5-(trifluoromethyl)-1,2,4-oxadiazol-3-yl)benzamide;
(S)—N-(1-Cyclopropyl-2-(pyrrolidin-1-yl)ethyl)-4-(5-(trifluoromethyl)-1,2,4-oxadiazol-3-yl)benzamide;
(R)—N-(1-Cyclopropyl-2-(pyrrolidin-1-yl)ethyl)-4-(5-(trifluoromethyl)-1,2,4-oxadiazol-3-yl)benzamide;
(R)—N-(1-(3,4-Dihydroisoquinolin-2(1H)-yl)propan-2-yl)-4-(5-(trifluoromethyl)-1,2,4-oxadiazol-3-yl)benzamide;
(R)—N-(1-(3-Phenylazetidin-1-yl)propan-2-yl)-4-(5-(trifluoromethyl)-1,2,4-oxadiazol-3-yl)benzamide;
D1: N—((R)-1-((abs)-3-(Difluoromethoxy)piperidin-1-yl)propan-2-yl)-4-(5-(trifluoromethyl)-1,2,4-oxadiazol-3-yl)benzamide;
D2: N—((R)-1-((abs)-3-(Difluoromethoxy)piperidin-1-yl)propan-2-yl)-4-(5-(trifluoromethyl)-1,2,4-oxadiazol-3-yl)benzamide;
(R)—N-(1-(5-Azaspiro[2.5]octan-5-yl)propan-2-yl)-4-(5-(trifluoromethyl)-1,2,4-oxadiazol-3-yl)benzamide;
(R)—N-(1-(6-Azaspiro[2.5]octan-6-yl)propan-2-yl)-4-(5-(trifluoromethyl)-1,2,4-oxadiazol-3-yl)benzamide;
(R)—N-(1-(Azepan-1-yl)propan-2-yl)-4-(5-(trifluoromethyl)-1,2,4-oxadiazol-3-yl)benzamide;
(R)—N-(1-(1-Azaspiro[3.3]heptan-1-yl)propan-2-yl)-4-(5-(trifluoromethyl)-1,2,4-oxadiazol-3-yl)benzamide;
(R)—N-(1-(5-Azaspiro[2.4]heptan-5-yl)propan-2-yl)-4-(5-(trifluoromethyl)-1,2,4-oxadiazol-3-yl)benzamide;
N—((R)-1-(3-Azabicyclo[3.2.1]octan-3-yl)propan-2-yl)-4-(5-(trifluoromethyl)-1,2,4-oxadiazol-3-yl)benzamide;
2-((R)-2-(4-(5-(Trifluoromethyl)-1,2,4-oxadiazol-3-yl)benzamido)propyl)octahydrocyclopenta[c]pyrrol-2-ium formate;
(R)—N-(1-(3,4-dihydro-2,7-naphthyridin-2(1H)-yl)propan-2-yl)-4-(5-(trifluoromethyl)-1,2,4-oxadiazol-3-yl)benzamide;
N-((2R)-1-(3-Azabicyclo[3.2.0]heptan-3-yl)propan-2-yl)-4-(5-(trifluoromethyl)-1,2,4-oxadiazol-3-yl)benzamide;
D1: N—((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide;
D2: N—((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide;
N-((2R)-1-(6,6-Dimethyl-3-azabicyclo[3.1.0]hexan-3-yl)propan-2-yl)-4-(5-(trifluoromethyl)-1,2,4-oxadiazol-3-yl)benzamide;
(2S)-1-((R)-2-(3-Fluoro-4-(5-(trifluoromethyl)-1,2,4-oxadiazol-3-yl)benzamido)propyl)-2-methylpyrrolidin-1-ium formate; and
N—((R)-1-((S)-2-Methylpyrrolidin-1-yl)propan-2-yl)-5-(5-(trifluoromethyl)-1,2,4-oxadiazol-3-yl)picolinamide,
or a pharmaceutically acceptable salt thereof.
Also provided is a compound selected from:
(2S)-2-Methyl-1-((R)-2-(3-methyl-4-(5-(trifluoromethyl)-1,2,4-oxadiazol-3-yl)benzamido)propyl)pyrrolidin-1-ium formate;
N-(2-(3-Azabicyclo[3.2.1]octan-3-yl)ethyl)-4-(5-(trifluoromethyl)-1,2,4-oxadiazol-3-yl)benzamide;
(R)—N-(1-(Isoindolin-2-yl)propan-2-yl)-4-(5-(trifluoromethyl)-1,2,4-oxadiazol-3-yl)benzamide;
N-((2R)-1-(3-Azabicyclo[3.1.0]hexan-3-yl)propan-2-yl)-4-(5-(trifluoromethyl)-1,2,4-oxadiazol-3-yl)benzamide;
(S)—N-(1-Cyclopropyl-2-(pyrrolidin-1-yl)ethyl)-4-(5-(trifluoromethyl)-1,2,4-oxadiazol-3-yl)benzamide;
(R)—N-(1-Cyclopropyl-2-(pyrrolidin-1-yl)ethyl)-4-(5-(trifluoromethyl)-1,2,4-oxadiazol-3-yl)benzamide;
(R)—N-(1-(3,4-Dihydroisoquinolin-2(1H)-yl)propan-2-yl)-4-(5-(trifluoromethyl)-1,2,4-oxadiazol-3-yl)benzamide;
(R)—N-(1-(3-Phenylazetidin-1-yl)propan-2-yl)-4-(5-(trifluoromethyl)-1,2,4-oxadiazol-3-yl)benzamide;
D1: N—((R)-1-((abs)-3-(Difluoromethoxy)piperidin-1-yl)propan-2-yl)-4-(5-(trifluoromethyl)-1,2,4-oxadiazol-3-yl)benzamide;
D2: N—((R)-1-((abs)-3-(Difluoromethoxy)piperidin-1-yl)propan-2-yl)-4-(5-(trifluoromethyl)-1,2,4-oxadiazol-3-yl)benzamide;
(R)—N-(1-(5-Azaspiro[2.5]octan-5-yl)propan-2-yl)-4-(5-(trifluoromethyl)-1,2,4-oxadiazol-3-yl)benzamide;
(R)—N-(1-(6-Azaspiro[2.5]octan-6-yl)propan-2-yl)-4-(5-(trifluoromethyl)-1,2,4-oxadiazol-3-yl)benzamide;
(R)—N-(1-(Azepan-1-yl)propan-2-yl)-4-(5-(trifluoromethyl)-1,2,4-oxadiazol-3-yl)benzamide;
(R)—N-(1-(1-Azaspiro[3.3]heptan-1-yl)propan-2-yl)-4-(5-(trifluoromethyl)-1,2,4-oxadiazol-3-yl)benzamide;
(R)—N-(1-(5-Azaspiro[2.4]heptan-5-yl)propan-2-yl)-4-(5-(trifluoromethyl)-1,2,4-oxadiazol-3-yl)benzamide;
N—((R)-1-(3-Azabicyclo[3.2.1]octan-3-yl)propan-2-yl)-4-(5-(trifluoromethyl)-1,2,4-oxadiazol-3-yl)benzamide;
2-((R)-2-(4-(5-(Trifluoromethyl)-1,2,4-oxadiazol-3-yl)benzamido)propyl)octahydrocyclopenta[c]pyrrol-2-ium formate;
(R)—N-(1-(3,4-dihydro-2,7-naphthyridin-2(1H)-yl)propan-2-yl)-4-(5-(trifluoromethyl)-1,2,4-oxadiazol-3-yl)benzamide;

N-((2R)-1-(3-Azabicyclo[3.2.0]heptan-3-yl)propan-2-yl)-4-(5-(trifluoromethyl)-1,2,4-oxadiazol-3-yl)benzamide;

D1: N—((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide;

D2: N—((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide;

N-((2R)-1-(6,6-Dimethyl-3-azabicyclo[3.1.0]hexan-3-yl)propan-2-yl)-4-(5-(trifluoromethyl)-1,2,4-oxadiazol-3-yl)benzamide;

(2S)-1-((R)-2-(3-Fluoro-4-(5-(trifluoromethyl)-1,2,4-oxadiazol-3-yl)benzamido)propyl)-2-methylpyrrolidin-1-ium formate;

N—((R)-1-((S)-2-Methylpyrrolidin-1-yl)propan-2-yl)-5-(5-(trifluoromethyl)-1,2,4-oxadiazol-3-yl)picolinamide;

3-methyl-N—((R)-1-((S)-2-methylpyrrolidin-1-yl)propan-2-yl)-4-(5-(trifluoromethyl)-1,2,4-oxadiazol-3-yl)benzamide;

N-((2R)-1-(hexahydrocyclopenta[c]pyrrol-2(1H)-yl)propan-2-yl)-4-(5-(trifluoromethyl)-1,2,4-oxadiazol-3-yl)benzamide;

3-fluoro-N—((R)-1-((S)-2-methylpyrrolidin-1-yl)propan-2-yl)-4-(5-(trifluoromethyl)-1,2,4-oxadiazol-3-yl)benzamide; and or a pharmaceutically acceptable salt thereof.

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting at least one histone deacetylase. Also provided is a use of at least one compound, or pharmaceutically acceptable salt thereof, described herein in the manufacture of medicament for inhibiting at least one histone deacetylase. Also provided is at least one compound, or pharmaceutically acceptable salt thereof, described herein for use in a method for inhibiting at least one histone deacetylase. In some embodiments, the at least one histone deacetylase is a Class IIa HDAC. In some embodiments, the at least one histone deacetylase has homology to yeast HDA1. In some embodiments, the at least one histone deacetylase is selected from HDAC-4, HDAC-5, HDAC-7, and HDAC-9. In some embodiments, the inhibition is in a cell. In some embodiments, the compound, or pharmaceutically acceptable salt thereof, described herein is selective for inhibiting at least one class II histone deacetylase. In some embodiments, the compound, or pharmaceutically acceptable salt thereof, described herein is a selective inhibitor of HDAC-4 and/or HDAC-5.

Also provided is a method of treating a condition or disorder mediated by HDAC in a subject in need of such a treatment, comprising administering to the subject a therapeutically effective amount of at least one compound, or pharmaceutically acceptable salt thereof, described herein. Also provided is a method of treating a condition or disorder mediated by HDAC in a subject in need of such a treatment, comprising administering to the subject a therapeutically effective amount of at least one compound, or pharmaceutically acceptable salt thereof, described herein. Also provided is a use of at least one compound, or pharmaceutically acceptable salt thereof, described herein in the manufacture of medicament for the treatment of a condition or disorder mediated by HDAC. Also provided is at least one compound, or pharmaceutically acceptable salt thereof, described herein for use in a method for the treatment of the human or animal body by therapy. Also provided is at least one compound, or pharmaceutically acceptable salt thereof, described herein for use in a method for the treatment of a condition or disorder.

Also provided is a method of treating a condition or disorder responsive to inhibition of at least one histone deacetylase in a patient in need thereof comprising administering to the patient a therapeutically effective amount of a compound, or pharmaceutically acceptable salt thereof, described herein. In some embodiments, the at least one histone deacetylase is HDAC-4. In some embodiments, the condition or disorder involves a neurodegenerative pathology. In some embodiments, the condition or disorder is Huntington's disease.

In some embodiments, the condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

In some embodiments, the neurodegenerative pathology is chosen from Alzheimer's disease, Parkinson's disease, neuronal intranuclear inclusion disease (NIID), dentatorubral pallidolusyian atrophy (DRPLA), Friedreich's ataxia, Rubenstein-Taubi syndrome, and polyglutamine diseases such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, and mixed connective tissue disease.

In some embodiments, the neurodegenerative pathology is an acute or chronic degenerative disease of the eye. Acute or chronic degenerative diseases of the eye include glaucoma, dry age-related macular degeneration, retinitis pigmentosa and other forms of heredodegenerative retinal disease, retinal detachment, macular pucker, ischemia affecting the outer retina, cellular damage associated with diabetic retinopathy and retinal ischemia, damage associated with laser therapy, ocular neovascular, diabetic retinopathy, rubeosis iritis, uveitis, Fuch's heterochromatic iridocyclitis, neovascular glaucoma, corneal neovascularization, retinal ischemia, choroidal vascular insufficinency, choroidal thrombosis, carotid artery ischemia, contusive ocular injury, retinopathy of permaturity, retinal vein occlusion, proliferative vitreoretinopathy, corneal angiogenesis, retinal microvasculopathy, and retinal edema.

In some embodiments, the condition or disorder mediated by HDAC comprises a fibrotic disease such as liver fibrosis, cystic fibrosis, cirrhosis, and fibrotic skin diseases, e.g., hypertrophic scars, keloid, and Dupuytren's contracture.

Accordingly, also provided is a method of treating a fibrotic disease mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a psychological disorder, such as depression, bipolar disease and dementia. In some embodiments, the condition or disorder mediated by HDAC comprises depression. Accordingly, also provided is a method of treating a psychological disorder, such as depression, mediated by HDAC in a subject in need of such a treatment, comprising administering to the subject a therapeutically effective amount of at least one compound, or pharmaceutically acceptable salt thereof, described herein. In some embodiments, the depression is chosen from major depressive disorder, and bipolar disorder.

In some embodiments, the condition or disorder mediated by HDAC comprises anxiety. Accordingly, also provided is a method of treating an anxiety mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises schizophrenia. Accordingly, also provided is a method of treating a schizophrenia mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a motor neuron disease, muscle atrophy/muscle wasting disorders, or amyotrophic lateral sclerosis (ALS). Accordingly, also provided is a method of treating a motor neuron disease, muscle atrophy/muscle wasting disorders, or amyotrophic lateral sclerosis (ALS) mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a cardiovascular condition. Accordingly, also provided is a method of treating a cardiovascular condition mediated by HDAC in a subject in need of such a treatment, comprising administering to the subject a therapeutically effective amount of at least one compound, or pharmaceutically acceptable salt thereof, described herein. In some embodiments, the cardiovascular condition is chosen from cardiomyopathy, cardiac hypertrophy, myocardial ischemia, heart failure, cardiac restenosis, and arteriosclerosis.

In some embodiments, the condition or disorder mediated by HDAC comprises cancer. Accordingly, also provided is a method of treating cancer mediated by HDAC in a subject in need of such a treatment, comprising administering to the subject a therapeutically effective amount of at least one compound, or pharmaceutically acceptable salt thereof, described herein. In some embodiments, the cancer is chosen from lymphoma, pancreatic cancer, colorectal cancer, hepatocellular carcinoma, Waldenstrom macroglobulinemia, hormone refractory cancer of the prostate, and leukaemia, breast cancer, lung cancer, ovarian cancer, prostate cancer, head and neck cancer, renal cancer, gastric cancer, brain cancer, B-cell lymphoma, peripheral T-cell lymphoma, and cutaneous T-cell lymphoma. In some further embodiments, the cancer is chosen from the following cancer types. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Also provided are methods of sensitization of tumors to radiotherapy by administering the compound according to the present disclosure before, during or after irradiation of the tumor for treating cancer.

In some embodiments, the condition or disorder mediated by HDAC comprises a condition or disorder treatable by immune modulation. Accordingly, also provided is a method of treating a condition or disorder treatable by immune modulation mediated by HDAC in a subject in need of such a treatment, comprising administering to the subject a therapeutically effective amount of at least one compound, or pharmaceutically acceptable salt thereof, described herein. In some embodiments, the condition or disorder treatable by immune modulation is chosen from asthma, irritable bowel syndrome, Crohn's disease, ulcerative colitis, bowel motility disorders, hypertension, rheumatoid arthritis, osteoarthritis, juvenile chronic arthritis, graft versus host disease, psoriasis, spondyloarthropathy, inflammatory bowel disease, alcoholic hepatitis, Sjogren's syndrome, ankylosing spondylitis, membranous glomerulopathy, discogenic pain, systemic lupus erythematosus, allergic bowel disease, coeliac disease, bronchitis, cystic fibrosis, rheumatoid spondylitis, osteoarthritis, uveitis, iritis, and conjunctivitis, ischemic bowel disease, psoriasis, eczema, dermatitis, septic arthritis, gout, pseudogout, juvenile arthritis, Still's disease, Henoch-Schonlein purpura, psoriatic arthritis, myalgia, reactive arthritis (Reiter's syndrome), hemochromatosis, Wegener's granulomatosis, familial Mediterranean fever (FMF), HBDS (hyperimmunoglobulinemia D and periodic fever syndrome), TRAPS (TNF-alpha receptor associated periodic fever syndrome), chronic obstructive pulmonary disease, neonatal-onset multisystem inflammatory disease (NOMID), cryopyrin-associated periodic syndrome (CAPS), and familial cold autoinflammatory syndrome (FCAS).

In some embodiments, the condition or disorder mediated by HDAC comprises an allergic disease. Accordingly, also provided is a method of treating an allergic disease, mediated by HDAC in a subject in need of such a treatment, comprising administering to the subject a therapeutically effective amount of at least one compound, or pharmaceutically acceptable salt thereof, described herein. Allergic diseases include, but are not limited to, respiratory allergic diseases such as allergic rhinitis, hypersensitivity lung diseases, hypersensitivity pneumonitis, eosinophilic pneumonias, Loeffler's syndrome, chronic eosinophilic pneumonia, delayed-type hypersensitivity, interstitial lung diseases (ILD), idiopathic pulmonary fibrosis, polymyositis, dermatomyositis, systemic anaphylaxis, drug allergies (e.g., to penicillin or cephalosporins), and insect sting allergies.

In some embodiments, the condition or disorder mediated by HDAC comprises an infectious disease such as a fungal infection, bacterial infection, viral infection, and protozoal infection, e.g., malaria, giardiasis, leishmaniasis, Chaga's disease, dysentery, toxoplasmosis, and coccidiosis. In some embodiments, the condition or disorder mediated by HDAC comprises malaria. Accordingly, also provided is a method of treating an infectious disease, such as malaria, mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises autism or Rett syndrome. Accordingly, also provided is a method of treating autism or Rett syndrome mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a hematological disorder such as thalassemia, anemia, and sickle cell anemia. Accordingly, also provided is a method of treating a hematological disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a metabolic disease such as prediabetes or diabetes (type I or II). Accordingly, also provided is a method of treating a metabolic disease, such as prediabetes or diabetes (type I or II), mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder that may also be treated by progenitor/stem cell based therapies such as: disorders related to diabetes (organ failure, cirrhosis, and hepatitis); central nervous system (CNS) disorders associated with dysregulation of progenitor cells in the brain (e.g., post-traumatic stress disorder (PTSD); tumors (e.g., retinoblastomas); disorders affecting oligodendrocyte progenitor cells (e.g., astrocytomas and ependimal cell tumors); multiple sclerosis; demyelinating disorders such as the leukodystrophies; neuropathies associated with white matter loss; and cerebellar disorders such as ataxia; and olfactory progenitor disorders (e.g., anosmic conditions). Accordingly, also provided is a method of treating a disorder that is mediated by HDAC in a subject in need of such a treatment, comprising administering to the subject a therapeutically effective amount of at least one compound, or pharmaceutically acceptable salt thereof, described herein, either before, during, or after a treatment with progenitor/stem cell based therapies.

In some embodiments, the condition or disorder mediated by HDAC comprises a disorder related to the proliferation of epithelial and mesenchymal cells (e.g., tumors, wound healing, and surgeries). Accordingly, also provided is a method of treating a disorder related to the proliferation of epithelial and mesenchymal cells that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder related to the proliferation of bone progenitors (e.g., osteoblasts and osteoclasts), disorders related to hair and epidermal progenitors (e.g., hair loss, cutaneous tumors, skin regeneration, burns, and cosmetic surgery); and disorders related to bone loss during menopause. Accordingly, also provided is a method of treating disorders related to the proliferation of bone progenitors, disorders related to hair and epidermal progenitors, or disorders related to bone loss that are mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is a viral disorder for which blood cells become sensitized to other treatments after HDAC inhibition, following administering to the subject a therapeutically effective amount of at least one compound, or pharmaceutically acceptable salt thereof, as described herein. Accordingly, also provided is a method of treating a viral disorder, wherein blood cells become sensitized to other treatments after HDAC inhibition, that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is an immune disorder that may be co-treated with TNFα or other immune modulators, upon administering to the subject a therapeutically effective amount of at least one compound, or pharmaceutically acceptable salt thereof, as described herein. Accordingly, also provided is a method of treating an immune disorder that is mediated by HDAC in a subject in need of such a treatment, comprising administering to the subject a therapeutically effective amount of at least one compound, or pharmaceutically acceptable salt thereof, described herein, either before, during, or after a treatment with TNFα or other immune modulators.

In some embodiments, the condition or disorder mediated by HDAC comprises a graft rejection or transplant rejection. Accordingly, also provided is a method of treating a disorder related to a graft rejection or a transplant rejection that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a blood pressure disorder related to nitric oxide (NO) regulation (e.g., hypertension, erectile dysfunction, asthma; and ocular disorders as glaucoma). Accordingly, also provided is a method of treating a blood pressure disorder related to nitric oxide (NO) regulation that is mediated by HDAC in a subject in need of such a treatment, comprising administering to the subject a therapeutically effective amount of at least one compound, or pharmaceutically acceptable salt thereof, described herein. In some embodiments, the condition or disorder is a cardiac hypertrophic disorder. Accordingly, also provided is a method of treating a cardiac hypertrophic disorder that is mediated by HDAC in a subject in need of such a treatment, comprising administering to the subject a therapeutically effective amount of at least one compound, or pharmaceutically acceptable salt thereof, described herein.

Also provided are methods of treatment in which at least one compound, or pharmaceutically acceptable salt thereof, described herein is the only active agent given to the subject and methods of treatment in which at least one compound, or pharmaceutically acceptable salt thereof, described herein is given to the subject in combination with one or more additional active agents.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, such as once or twice a day.

In some embodiments, the compounds, or pharmaceutically acceptable salts thereof, described herein are administered as a pharmaceutical composition. Accordingly, provided are pharmaceutical compositions comprising at least one compound, or pharmaceutically acceptable salt thereof, described herein, together with at least one pharmaceutically acceptable vehicle chosen from carriers, adjuvants, and excipients. A compound of the present disclosure can be formulated into pharmaceutical compositions using techniques well known to those in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, is sufficient to provide a practical quantity of material for administration per unit dose of the compound, or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein.

Effective concentrations of at least one compound, or pharmaceutically acceptable salt thereof, described herein are mixed with a suitable pharmaceutically acceptable vehicle. In instances in which the compound, or pharmaceutically acceptable salt thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of a compound, or pharmaceutically acceptable salt thereof, described herein, the resulting mixture may be a solution, suspension, emulsion or the like. The form of the resulting mixture depends upon a number of factors, including the intended mode of administration and the solubility of the compound, or pharmaceutically acceptable salt thereof, in the chosen vehicle. The effective concentration sufficient for ameliorating the symptoms of the disease treated may be empirically determined.

The compounds, or pharmaceutically acceptable salts thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt thereof, described herein. In some embodiments, oral pharmaceutical compositions contain at least 5% (weight %) of at least one compound, or pharmaceutically acceptable salt thereof, described herein. Some embodiments contain from 25% to 50% or from 5% to 75% of at least one compound, or pharmaceutically acceptable salt thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein can be incorporated into oral liquid preparations such as aqueous or oily suspensions, solutions, emulsions, syrups, or elixirs, for example. Furthermore, pharmaceutical compositions containing the compound, or pharmaceutically acceptable salt thereof, described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein may be administered parenterally in a sterile medium. Parenteral administration includes subcutaneous injections, intravenous, intramuscular, intrathecal injection or infusion techniques. The compound, or pharmaceutically acceptable salt thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein may also be formulated for transdermal administration as a transdermal patch.

Topical pharmaceutical compositions comprising at least one compound, or pharmaceutically acceptable salt thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or pharmaceutically acceptable salt thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt thereof, described herein, and instructions for using the composition to treat a subject (typically a human patient). In some embodiments, the instructions are for using the pharmaceutical composition to treat a subject suffering a condition or disorder mediated by HDAC. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt thereof, can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt thereof, described herein and one or more additional agents used in the treatment of Huntington's disease such as, but not limited to, Amitriptyline, Imipramine, Desipramine, Nortriptyline, Paroxetine, Fluoxetine, Sertraline, Tetrabenazine, Haloperidol, Chlorpromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt thereof, described herein and one or more additional pharmaceutical agents used in the treatment of Huntington's disease such as, but not limited to, Amitriptyline, Imipramine, Desipramine, Nortriptyline, Paroxetine, Fluoxetine, Setraline, Terabenazine, Haloperidol, Chlorpromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Huntington's disease such as, but not limited to, Amitriptyline, Imipramine, Desipramine, Nortriptyline, Paroxetine, Fluoxetine, Setraline, Terabenazine, Haloperidol, Chlorpromazine, Thioridazine, Sulpride, Quetiapine, Clozapine, and Risperidone.

Also provided are methods for treating Alzheimer's disease, including treating memory and/or cognitive impairment associated with Alzheimer's disease, comprising administering to a subject, simultaneously or sequentially, at least one compound, or pharmaceutically acceptable salt thereof, described herein and one or more additional agents used in the treatment of Alzheimer's disease such as, but not limited to, Reminyl®, Cognex®, Aricept®, Exelon®, Akatinol®, Neotropin™, Eldepryl®, Estrogen and Clioquinol. In methods using simultaneous administration, the agents can be present in a combined composition or can be administered separately. Also provided are pharmaceutical compositions comprising at least one compound, or pharmaceutically acceptable salt thereof, described herein, and one or more additional pharmaceutical agents used in the treatment of Alzheimer's disease such as, but not limited to, Reminyl®, Cognex®, Aricept®, Exelon®, Akatinol®, Neotropin™, Eldepryl®, Estrogen and Clioquinol. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Alzheimer's disease such as, but not limited to Reminyl®, Cognex®, Aricept®, Exelon®, Akatinol®, Neotropin™, Eldepryl®, Estrogen and Clioquinol.

Also provided are methods for treating cancer comprising administering to a subject, simultaneously or sequentially, at least one compound, or pharmaceutically acceptable salt thereof, described herein and one or more additional agents used in the treatment of cancer such as, but not limited to, the following categories of anti-tumor agents:

(i) other cell cycle inhibitory agents that work by the same or different mechanisms from those defined herein before, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined herein before (for example receptor tyrosine kinases like Tie-2, inhibitors of integrin $\alpha_v\beta_3$ function, angiostatin, razoxin, thalidomide), and including vascular targeting agents; and (v) differentiation agents (for example retinoic acid and vitamin D).

In methods using simultaneous administration, the agents can be present in a combined composition or can be administered separately. Also provided are pharmaceutical compositions comprising at least one compound, or pharmaceutically acceptable salt thereof, described herein, and one or more anti-tumor agent as described herein. Similarly, also provided are packaged pharmaceutical compositions containing a pharmaceutical composition comprising at least one compound, or pharmaceutically acceptable salt thereof, described herein, and another composition comprising one or more one or more anti-tumor agent as described herein. When used in combination with one or more additional pharmaceutical agent or agents, the compounds described herein may be administered prior to, concurrently with, or following administration of the additional pharmaceutical agent or agents.

In some embodiments, the compounds, or pharmaceutically acceptable salts thereof, described herein, are administered in conjunction with surgery or radiotherapy, optionally in combination with one or more additional agents used in the treatment of cancer.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein is typically administered at dosage levels and in a manner customary for HDAC inhibitors. For example, the compound, or pharmaceutically acceptable salt thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt thereof, described herein, for example, 0.1-50 mg of at least one compound, or pharmaceutically acceptable salt thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt thereof, described herein.

A labeled form of a compound, or pharmaceutically acceptable salt thereof, described herein can be used as a diagnostic for identifying and/or obtaining compounds that have the function of modulating an activity of HDAC as described herein. The compound, or pharmaceutically acceptable salt thereof, described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

The present disclosure includes all isotopes of atoms occurring in the compounds and pharmaceutically acceptable salts thereof described herein. Isotopes include those atoms having the same atomic number but different mass numbers. The present disclosure also includes every combination of one or more atoms in the compounds and pharmaceutically acceptable salts thereof described herein that is replaced with an atom having the same atomic number but a different mass number. One such example is the replacement of an atom that is the most naturally abundant isotope, such as $^1$H or $^{12}$C, found in one of the compounds and pharmaceutically acceptable salts thereof described herein, with a different atom that is not the most naturally abundant isotope, such as $^2$H or $^3$H (replacing $^1$H), or $^{11}$C, $^{13}$C, or $^{12}$C (replacing $^{12}$C). A compound wherein such a replacement has taken place is commonly referred to as being isotopically-labeled. Isotopic-labeling of the compounds and pharmaceutically acceptable salts thereof described herein can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$O. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I. Also provided are pharmaceutical compositions comprising a compound or a pharmaceutically acceptable salt thereof described herein, wherein the naturally occurring distribution of the isotopes in the pharmaceutical composition is perturbed. Also provided are pharmaceutical compositions comprising a compound or a pharmaceutically acceptable salt thereof described herein enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or gas chromatography (GC). Certain isotopically-labeled compounds and pharmaceutically acceptable salts thereof described herein are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds and pharmaceutically acceptable salts thereof described herein can generally be prepared by following procedures analogous to those disclosed in the Examples infra, by substituting an isotopically labeled reagent for a non-isotopically labeled reagent. Moreover, it should be understood that all of the atoms represented in the compounds and pharmaceutically acceptable salts thereof described herein can be either the most commonly occurring isotope of such atoms or a scarcer radio-isotope or nonradioactive isotope.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, or pharmaceutically acceptable salts thereof, compositions, and methods described herein are further illustrated by the following non-limiting examples.

As used herein, the following abbreviations have the following meanings. If an abbreviation is not defined, it has its generally accepted meaning.

Abbreviations

AcOH Acetic acid
Bn: Benzyl
BOC or Boc: tert-butyloxycarbonyl
cPr: cyclopropyl

DCM: Dichloromethane
DIPE: Diisopropylether
DIPEA: Diisopropylethylamine
DMAP: Dimethylaminopyridine
DMF: Dimethylformamide
DMSO: Dimethylsulfoxide
EDC: 1-Ethyl-3-(3-dimethylaminopropyl)carbodiimide
eqs: equivalents
ES+: Electrospray Positive Ionisation
Et$_2$O: Diethyl ether
EtOAc: Ethyl acetate
EtOH: Ethanol
FBS Fetal bovine serum
h: Hour
HATU: (1-[Bis(dimethylamino)methylene]-1H-1,2,3-triazolo[4,5-b]pyridinium 3-oxid hexafluorophosphate)
HBTU: N,N,N',N'-Tetramethyl-O-(1H-benzotriazol-1-yl)uronium hexafluorophosphate
HOPO: 2-Hydroxypyridine-N-oxide
HPLC: High Performance Liquid Chromatography
i-hex: iso-Hexane
IPA: iso-Propyl alcohol
LCMS: Liquid Chromatography Mass Spectrometry
M: Mass
Me: Methyl
MeCN: Acetonitrile
MeOH: Methanol
min: minute(s)
Ms: Mesyl
NMR: Nuclear Magnetic Resonance
Pd/C: Palladium on carbon
Ph: Phenyl
RT: Retention time
r.t.: Room temperature
SFC: Supercritical Fluid Chromatography
SCX: Strong Cation Exchange
TFA: Trifluoroacetic acid
TFAA: Trifluoroacetic anhydride
THF: Tetrahydrofuran
v/v or V/V: volume to volume Compounds were named with the aid of the Cambridgesoft Chemistry Cartridge (v. 9.0.0.182) software.

All reactions involving air- or moisture-sensitive reagents were performed under a nitrogen atmosphere using dried solvents and glassware.

Analytical Conditions

| Analytical Method # | Description |
|---|---|
| Analytical method 1 | Solvents: Acetonitrile (far UV grade) with 0.1% (v/v) formic acid. Water (high purity via PureLab Option unit) with 0.1% formic acid<br>Column: Phenomenex Luna 5 μm C18 (2), 100 × 4.6 mm (Plus guard cartridge)<br>Flow Rate: 2 mL/min<br>gradient: A: Water/formic acid<br>B: MeCN/formic acid |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

Typical Injections 2-7 μL (concentration ~0.2-1.0 mg/mL)

| Analytical Method # | Description |
|---|---|
| Analytical method 2 | Solvents: - Acetonitrile (Far UV grade)<br>Water (High purity via PureLab Option unit) with 10 mM ammonium bicarbonate (ammonium hydrogen carbonate)<br>Column: - Waters Xterra MS 5μ C18, 100 × 4.6 mm (Plus guard cartridge)<br>Flow Rate: - 2 mL/min<br>Gradient: - A: Water/Bicarb B: MeCN |

| Time | A % | B % |
|---|---|---|
| 0.00 | 95 | 5 |
| 0.50 | 95 | 5 |
| 4.00 | 5 | 95 |
| 5.50 | 5 | 95 |
| 5.60 | 95 | 5 |
| 6.50 | 95 | 5 |

Typical Injections 2-7 μL (concentration ~0.2-1 mg/mL)

| Analytical Method # | Description |
|---|---|
| Analytical method 3 | Solvents: Acetonitrile (Far UV grade) with 0.1% (V/V) formic acid Water (High purity via PureLab Ultra unit) with 0.1% formic acid<br>Column: Hichrom ACE 3 C18-AR mixed mode column 100 × 4.6 mm<br>Flow Rate: 1 mL/min<br>gradient: A: Water/formic<br>B: MeCN/formic |

| Time | A % | B % |
|---|---|---|
| 0.00 | 98 | 2 |
| 3.00 | 98 | 2 |
| 12.00 | 0 | 100 |
| 15.4 | 0 | 100 |
| 15.5 | 98 | 2 |
| 17 | 98 | 2 |

Typical Injections 0.2-10 μL (concentration ~0.2-1.0 mg/mL)

| Analytical Method # | Description |
|---|---|
| Analytical method 4 | Solvents: - Acetonitrile (Far UV grade) with 0.1% (V/V) formic acid<br>Water (High purity via PureLab Ultra unit) with 0.1% formic acid<br>Column: Supelco, Ascentis ® Express C18 or Hichrom Halo C18, 2.7 μm C18, 150 × 4.6 mm. Both latest technology fused core columns<br>Flow Rate: 1 ml/min<br>Gradient: A: Water/formic<br>B: MeCN/formic |

| Time | A % | B % |
|---|---|---|
| 0.00 | 96 | 4 |
| 3.00 | 96 | 4 |
| 9.00 | 0 | 100 |
| 13.6 | 0 | 100 |
| 13.7 | 96 | 4 |
| 15 | 96 | 4 |

Typical Injections 0.2-10 μL (concentration ~0.2-1.0 mg/mL)

General Synthetic Methods

Scheme 1-Amide coupling route

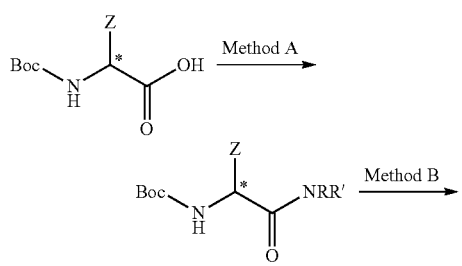

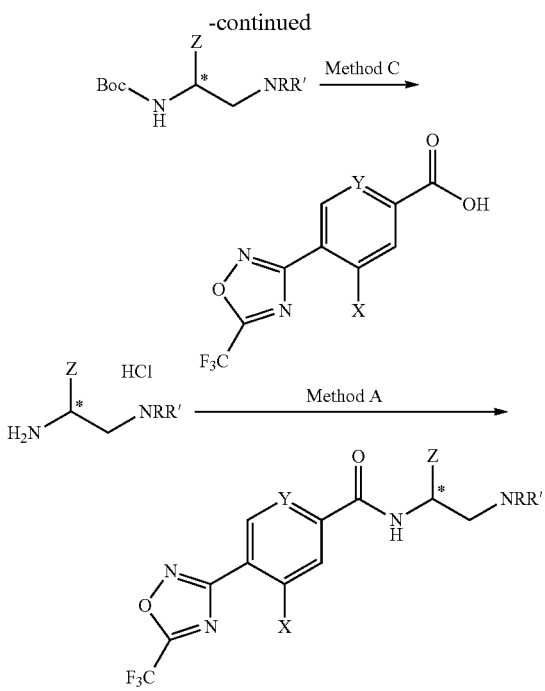

X = H, alkyl (e.g. Me) or halo (e.g. F)
Y = CH or N
Z = H, Me or cPr

Method a (Amide Coupling)

To a solution of carboxylic acid (1.50 mmol) in DCM (10 mL) at r.t. were added EDC (351 mg, 1.83 mmol) and HOPO (203 mg, 1.83 mmol). The mixture was stirred for 30 min to give a complete solution then amine (free base or hydrochloride salt) (1.65 mmol) and DIPEA (1.3 mL, 7.5 mmol) were added and the mixture stirred at r.t. for 18 h. The mixture was washed with water, passed through a phase separation cartridge and concentrated.

Method B (Amide Reduction)

To a solution of amide (1.30 mmol) in diethyl ether (50 mL) at −15 OC under nitrogen was added dropwise lithium aluminum hydride (1.30 mL, 2.6 mmol, 2.0 M in THF) over 20 min. The reaction was maintained at −10° C. for 1.5 h then quenched with water (1.5 mL), 2 N NaOH (1 mL) and further water (2 mL). The reaction was warmed to r.t. and stirred for 30 min, then MgSO₄ was added and the reaction was filtered through Celite, washing well with EtOAc. The filtrate was concentrated and the residue purified by passage through an SCX cartridge (5 g), eluting with 0-10% 7 M methanolic ammonia in DCM.

Method C (Boc Removal)

To a solution of Boc-protected amine (0.76 mmol) in DCM (5 mL) at 0° C. under nitrogen was added dropwise 4 N HCl in dioxane (0.8 mL, 3.0 mmol). The solution was warmed to r.t. and stirred for 1 h, then concentrated.

Scheme 2-Mesylate displacement route

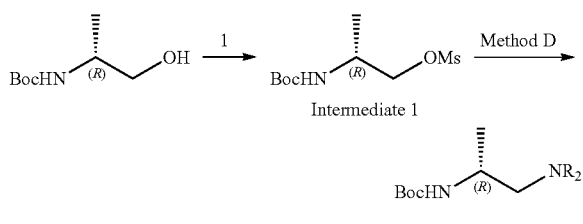

Step 1: (R)-2-((tert-butoxycarbonyl)amino)propyl methanesulfonate (Intermediate 1)

A solution of methanesulfonyl chloride (7.29 mL, 94.2 mmol) in dry DCM (140 mL) was added dropwise, over a period of 1.5 h, to a solution of (R)-tert-butyl (1-hydroxypropan-2-yl)carbamate (15 g, 85.6 mmol) and triethylamine (17.9 mL, 128.4 mmol) in DCM (300 mL) at 0° C. The reaction was stirred at 0° C. for 30 min, then 1 h at r.t, before washing with water (300 mL), NaHCO₃ (300 mL) and brine (200 mL). The organics were passed through a phase separator, and concentrated under reduced pressure to give the title compound as a salmon pink solid (21.5 g, 99%).

Method D

Amine (7.12 mmol) was added to intermediate 1 (900 mg, 3.56 mmol) and cesium carbonate (3.48 g, 10.7 mmol) in DMF (8 mL) and the mixture stirred at 65° C. for 24 h. The reaction mixture was cooled to r.t. and filtered through celite, washing with MeOH. The filtrate was concentrated and the residue purified by passage through an SCX cartridge (5 g), eluting with 0-10% 7 M methanolic ammonia in DCM.

(R)-1-((S)-2-Methylpyrrolidin-1-yl)propan-2-amine dihydrochloride (Intermediate 2)

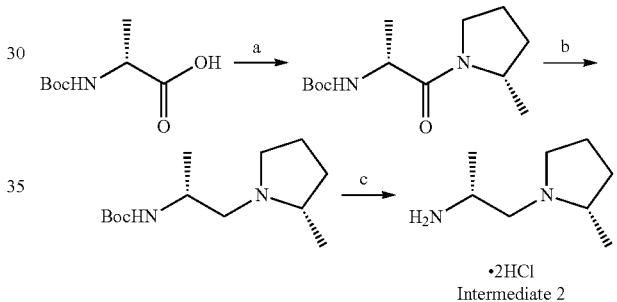

Step 1: tert-Butyl ((R)-1-((S)-2-methylpyrrolidin-1-yl)-1-oxopropan-2-yl)carbamate Following method A from (R)-2-((tert-butoxycarbonyl)amino)propanoic acid (1.14 g, 6.04 mmol) and (S)-2-methylpyrrolidine (565 mg, 6.65 mmol) gave the title compound as a yellow oil which was progressed to the next step as crude.

Step 2: tert-Butyl ((R)-1-((S)-2-methylpyrrolidin-1-yl)propan-2-yl)carbamate

Following method B from tert-butyl ((R)-1-((S)-2-methylpyrrolidin-1-yl)-1-oxopropan-2-yl)carbamate (1.55 g, 6.04 mmol) gave the title compound as a colorless oil (1.43 g, 97%).

Step 3: (R)-1-((S)-2-Methylpyrrolidin-1-yl)propan-2-amine dihydrochloride (Intermediate 2)

Following method C from tert-butyl ((R)-1-((S)-2-methylpyrrolidin-1-yl)propan-2-yl)carbamate (1.43 g, 5.88 mmol) gave the title compound as a colorless oil (850 mg, 81%).

Example 1: (2S)-2-Methyl-1-((R)-2-(3-methyl-4-(5-(trifluoromethyl)-1,2,4-oxadiazol-3-yl)benzamido)propyl)pyrrolidin-1-ium formate

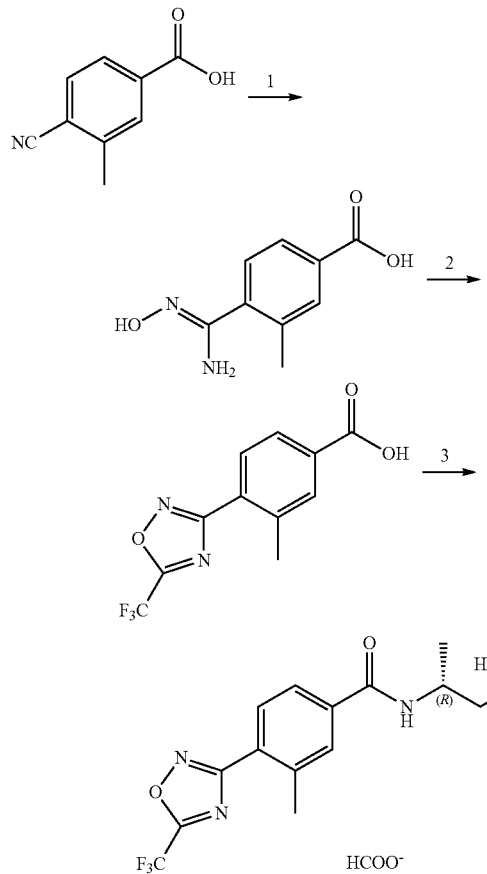

Step 1: (Z)-4-(N-Hydroxycarbamimidoyl)-3-methylbenzoic acid

To a stirred solution of 4-cyano-3-methylbenzoic acid (1.00 g, 6.21 mmol) in EtOH (30 mL) was added NH$_2$OH.HCl (604 mg, 8.70 mmol) and KOH (1.04 g, 18.6 mmol). The mixture was stirred at r.t. for 17 h, then neutralized with 1 M HCl$_{(aq)}$ and extracted into EtOAc (3×25 mL). The combined organics were dried (MgSO$_4$) and concentrated to give the title compound as a yellow solid (1.3 g, 108%).

Step 2: 3-Methyl-4-(5-(trifluoromethyl)-1,2,4-oxadiazol-3-yl)benzoic acid

To a stirred solution of (Z)-4-(N'-hydroxycarbamimidoyl)-3-methylbenzoic acid (1.2 g, 6.21 mmol) in THF (30 mL) was added TFAA (1.29 mL, 9.32 mmol). The mixture was stirred for 3 h, after which time an additional 5 eqs of TFAA were added. After a further 2 h stirring, LCMS indicated the reaction was complete. The mixture was poured onto ice-water and acidified to pH 4 with 1 M HCl$_{(aq)}$, before extracting into EtOAc (3×30 mL). The combined organics were dried (MgSO$_4$) and concentrated. Purification by flash column chromatography (gradient elution i-hex [+3% AcOH] to 4:1 i-hex:EtOAc [+3% AcOH]) gave the title compound as an off-white solid. LCMS (ES+) consistent with target (M+H)$^+$.

Step 3: (2S)-2-Methyl-1-((R)-2-(3-methyl-4-(5-(trifluoromethyl)-1,2,4-oxadiazol-3-yl)benzamido)propyl)pyrrolidin-1-ium formate

Following method A from 3-methyl-4-(5-(trifluoromethyl)-1,2,4-oxadiazol-3-yl)benzoic acid (490 mg, 1.80 mmol) and intermediate 2(386 mg, 2.70 mmol). Purification by reverse phase chromatography gave the title compound as an orange gum (65 mg, 9%). LCMS (ES+) 397 (M+H)$^+$, RT 2.85 min (Analytical method 1). $^1$H NMR δ (ppm) (400 MHz, DMSO-d$_6$) 8.40 (1H, d, J=8.3 Hz), 8.17 (1H, s), 8.04 (1H, d, J=8.2 Hz), 7.92 (1H, s), 7.88-7.85 (1H, m), 4.19-4.10 (1H, m), 3.16-3.10 (1H, m), 2.78-2.67 (1H, m), 2.65 (3H, s), 2.42-2.33 (1H, m), 2.29-2.15 (2H, m), 1.93-1.83 (1H, m), 1.72-1.62 (2H, m), 1.36-1.25 (1H, m), 1.19 (3H, d, J=6.7 Hz), 1.05 (3H, d, J=6.0 Hz). NH$^+$ not observed.

Example 2: N-(2-(3-Azabicyclo[3.2.1]octan-3-yl)ethyl)-4-(5-(trifluoromethyl)-1,2,4-oxadiazol-3-yl)benzamide

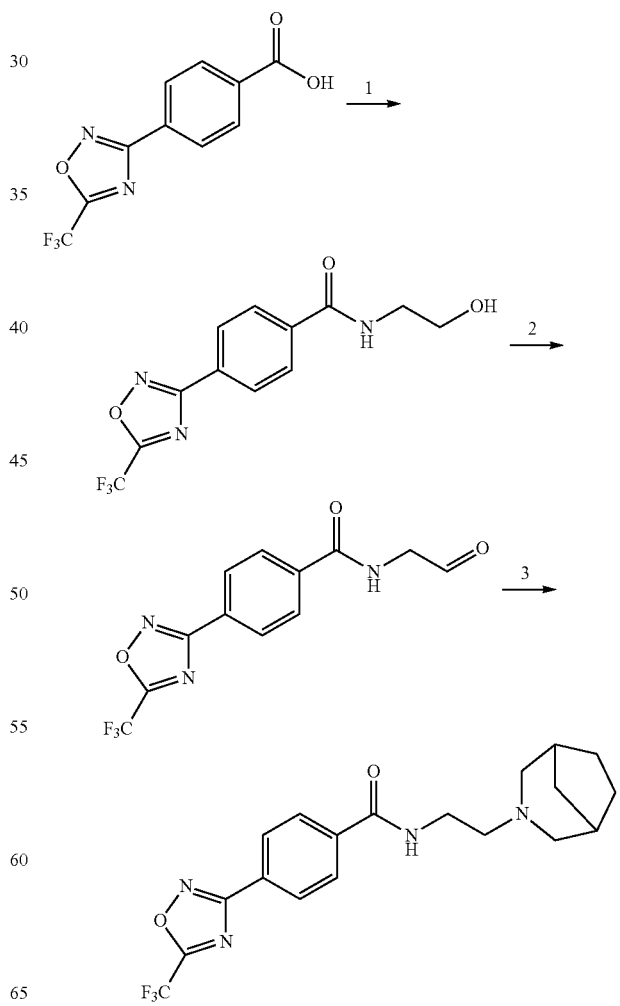

Step 1: N-(2-Hydroxyethyl)-4-(5-(trifluoromethyl)-1,2,4-oxadiazol-3-yl)benzamide Following method A from 4-(5-(trifluoromethyl)-1,2,4-oxadiazol-3-yl)benzoic acid (1.5 g, 5.8 mmol) and 2-aminoethanol (420 µL, 6.96 mmol) gave the title compound as a white solid (938 mg, 54%). LCMS (ES+) consistent with target (M+H)+.

Step 2: N-(2-Oxoethyl)-4-(5-(trifluoromethyl)-1,2,4-oxadiazol-3-yl)benzamide To a suspension of N-(2-hydroxyethyl)-4-(5-(trifluoromethyl)-1,2,4-oxadiazol-3-yl)benzamide (938 mg, 3.11 mmol) in DCM (50 mL) was added Dess-Martin periodinane (1.98 g, 4.67 mmol). The reaction mixture was stirred at r.t. for 66 h and then quenched with MeOH (15 mL). The mixture was stirred for 15 min and then concentrated onto silica. Purification by column chromatography (i-hex to EtOAc/i-hex (1:1)) gave the title compound (450 mg, 48%).

Step 3: N-(2-((1R,5S)-3-Azabicyclo[3.2.1]octan-3-yl)ethyl)-4-(5-(trifluoromethyl)-1,2,4-oxadiazol-3-yl)benzamide To a stirred solution of N-(2-oxoethyl)-4-(5-(trifluoromethyl)-1,2,4-oxadiazol-3-yl)benzamide (87 mg, 0.4 mmol) in DCM:AcOH (10:1, 4 mL) was added 3-azabicyclo[3.2.1]octane (70 mg, 0.48 mmol) and PS-triethylammonium cyanoborohydride (200 mg, 0.8 mmol). The reaction was shaken for 4 h before filtering and concentrating under reduced pressure. Purification by preparative-HPLC gave the title compound. LCMS (ES+) 395 (M+H)+, RT 2.75 min (Analytical Method 1); 1H NMR δ (ppm) (400 MHz, DMSO-$d_6$) 8.55-8.50 (1H, m,), 8.17 (2H, d, J=8.5 Hz), 8.04 (2H, d, J=8.5 Hz), 3.40-3.35 (2H, m), 2.72-2.66 (2H, m), 2.46 (2H, dd, J=6.8, 6.8 Hz), 2.09-2.03 (4H, m), 1.60-1.51 (2H, m), 1.50-1.38 (3H, m), 1.31 (1H, d, J=10.7 Hz).

Example 3: (R)—N-(1-(Isoindolin-2-yl)propan-2-yl)-4-(5-(trifluoromethyl)-1,2,4-oxadiazol-3-yl)benzamide

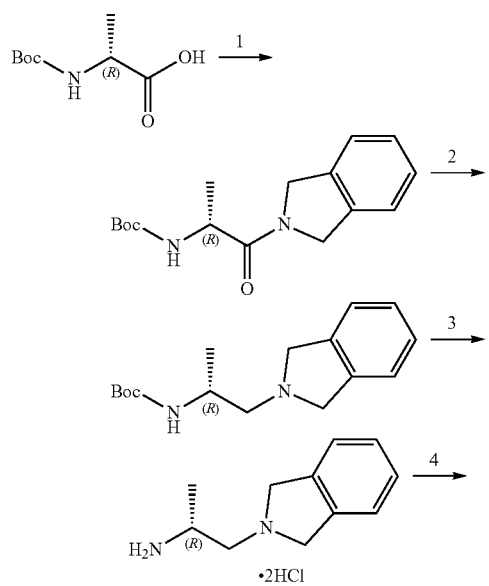

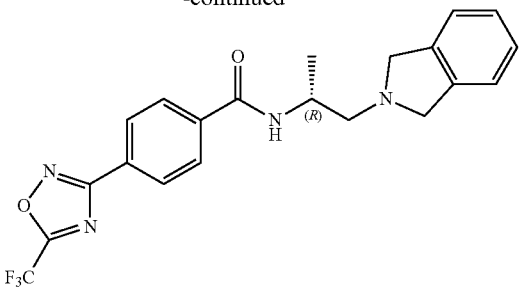

Step 1: (R)-tert-Butyl (1-(isoindolin-2-yl)-1-oxopropan-2-yl)carbamate

Following method A from (R)-2-((tert-butoxycarbonyl)amino)propanoic acid (3.78 mmol) and isoindoline (4.16 mmol). Purification by column chromatography (gradient elution, 0-100% EtOAc in i-hex) gave the title compound as a pale yellow gum (1.01 g, 87%, 60% pure) which was used without further purification.

Step 2: (R)-tert-Butyl (1-(isoindolin-2-yl)propan-2-yl)carbamate

Following method B from (R)-tert-butyl (1-(isoindolin-2-yl)-1-oxopropan-2-yl)carbamate (3.78 mmol). The title compound was obtained as a yellow gum (0.84 g, 80%).

Step 3: (R)-1-(Isoindolin-2-yl)propan-2-amine dihydrochloride

Following method C from (R)-tert-butyl (1-(isoindolin-2-yl)propan-2-yl)carbamate (3.04 mmol). The title compound was obtained as a dark green foam (655 mg, 86%).

Step 4: (R)—N-(1-(Isoindolin-2-yl)propan-2-yl)-4-(5-(trifluoromethyl)-1,2,4-oxadiazol-3-yl)benzamide Following method A from (R)-1-(isoindolin-2-yl)propan-2-amine dihydrochloride (2.53 mmol) and 4-(5-(trifluoromethyl)-1,2,4-oxadiazol-3-yl)benzoic acid (2.78 mmol). Purification by preparative HPLC gave the title compound as a pale brown solid (60 mg, 6%). LCMS (ES+) 417 (M+H)+, RT 9.72 min (Analytical Method 3); 1H NMR δ (ppm) (400 MHz, DMSO-$d_6$) 8.50 (1H, d, J=8.2 Hz), 8.17 (2H, d, J=8.5 Hz), 8.08 (2H, d, J=8.5 Hz), 7.25-7.16 (4H, m), 4.33-4.24 (1H, m), 3.98-3.88 (4H, m), 2.89 (1H, dd, J=7.8, 11.9 Hz), 2.73 (1H, dd, J=6.4, 11.9 Hz), 1.23 (3H, d, J=6.7 Hz).

Example 4: N-((2R)-1-(3-Azabicyclo[3.1.0]hexan-3-yl)propan-2-yl)-4-(5-(trifluoromethyl)-1,2,4-oxadiazol-3-yl)benzamide

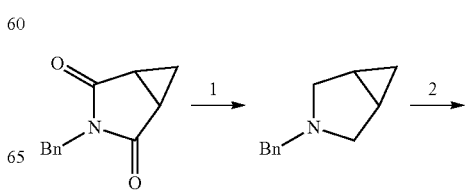

43

-continued

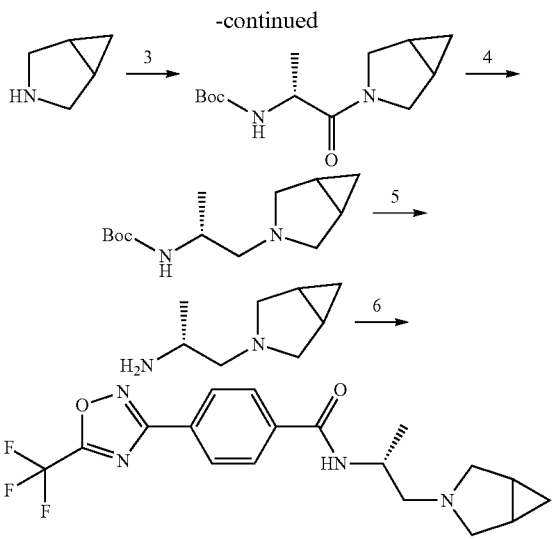

Step 1: 3-Benzyl-3-azabicyclo[3.1.0]hexane

3-Benzyl-3-azabicyclo[3.1.0]hexane-2,4-dione (1.95 g, 9.69 mmol, CAS No. 73799-63-0) was suspended in THF (11 mL) and cooled to 0° C. under a nitrogen atmosphere. LiAlH$_4$ (2 M in THF, 19.5 mL, 39.0 mmol) was added over several minutes with stirring. The reaction was heated to reflux and left to stir for 18 h. The reaction was then quenched with the slow addition of water (3 mL), 2 N NaOH (4 mL) and more water (8 mL). MgSO$_4$ was added and the mixture stirred for 30 min before being filtered through Celite and washed with EtOAc. The solvents were removed under reduced pressure to afford the title compound as an oily yellow solid (1.38 g, 82%). The compound was used in the next step without further purification.

Step 2: 3-Azabicyclo[3.1.0]hexane hydrochloride

3-Benzyl-3-azabicyclo[3.1.0]hexane (1.1 g, 6.35 mmol) was dissolved in methanol (40 mL) and 10% Pd/C (300 mg, 0.282 mmol) was added. The mixture was shaken under a hydrogen gas atmosphere (2 bar) for 18 h at r.t. The reaction mixture was then filtered through Celite, acidified with 4 N HCl in dioxane (2.38 mL, 9.53 mmol) and concentrated to yield the title compound a brown solid (680 mg, 90%) which was used in the next step without further purification.

Step 3: tert-Butyl ((2R)-1-(3-azabicyclo[3.1.0] hexan-3-yl)-1-oxopropan-2-yl)carbamate 3-Azabicyclo[3.1.0]hexane hydrochloride (670 mg, 5.6 mmol) was dissolved in DMF (15 mL) and HATU (2.55 g, 6.70 mmol) and Boc-D-Alanine (1.06 g, 5.60 mmol) added and the mixture stirred at r.t. for 10 minutes. DIPEA (2.92 mL, 16.8 mmol) was then added and the mixture left to stir at r.t. for 18 h before being diluted with EtOAc (20 mL), washed with 1 M HCl (15 mL), saturated NaHCO$_3$ (15 mL) and brine (15 mL). The organic layer was dried over MgSO$_4$, filtered and the filtrate concentrated to yield a yellow oil Purification by column chromatography (gradient elution, i-hex to 60% EtOAc in i-hex) to yield the title compound as a clear oil (380 mg, 27%).

44

Step 4: tert-Butyl ((2R)-1-(3-azabicyclo[3.1.0] hexan-3-yl)propan-2-yl)carbamate Following method B from tert-butyl ((2R)-1-(3-azabicyclo[3.1.0]hexan-3-yl)-1-oxopropan-2-yl)carbamate (380 mg, 1.50 mmol) afforded the title compound as a yellow oil (290 mg, 80%). The compound was used in the next step without further purification.

Step 5: (2R)-1-(3-Azabicyclo[3.1.0]hexan-3-yl)propan-2-amine

Following method C from tert-butyl ((2R)-1-(3-azabicyclo[3.1.0]hexan-3-yl)propan-2-yl)carbamate (290 mg, 1.20 mmol). The reaction mixture was then concentrated to yield a brown oil which was purified by SCX cartridge, eluting with MeOH/DCM (1:1) and then 0.5 N NH$_3$ in MeOH to yield the title compound as a yellow oil (110 mg, 65%) which was used in the next step without further purification.

Step 6: N-((2R)-1-(3-Azabicyclo[3.1.0]hexan-3-yl) propan-2-yl)-4-(5-(trifluoromethyl)-1,2,4-oxadiazol-3-yl)benzamide Following method A from (2R)-1-(3-azabicyclo[3.1.0] hexan-3-yl)propan-2-amine (83 mg, 0.59 mmol) and 4-(5-(trifluoromethyl)-1,2,4-oxadiazol-3-yl)benzoic acid (153 mg, 0.59 mmol). Purification by preparative-HPLC gave the title compound as an off white solid. LCMS (ES+) 381 (M+H)$^+$, RT 2.61 min (Analytical Method 1); $^1$H NMR δ (ppm) (400 MHz, CDCl$_3$) 8.19 (2H, td, J=1.8, 8.4 Hz), 7.92 (2H, td, J=1.8, 8.5 Hz), 6.97 (1H, br s), 4.08 (1H, br s), 3.10 (1H, d, J=8.8 Hz), 3.03 (1H, d, J=8.8 Hz), 2.74 (1H, t, J=10.3 Hz), 2.58 (1H, d, J=8.4 Hz), 2.52 (1H, dd, J=5.2, 12.3 Hz), 2.41 (1H, d, J=8.1 Hz), 1.42-1.39 (2H, m), 1.31 (3H, d, J=6.4 Hz), 0.65 (1H, dd, J=3.9, 8.0 Hz), 0.40 (1H, dt, J=4.3, 7.7 Hz).

Example 5: (S)—N-(1-Cyclopropyl-2-(pyrrolidin-1-yl)ethyl)-4-(5-(trifluoromethyl)-1,2,4-oxadiazol-3-yl)benzamide

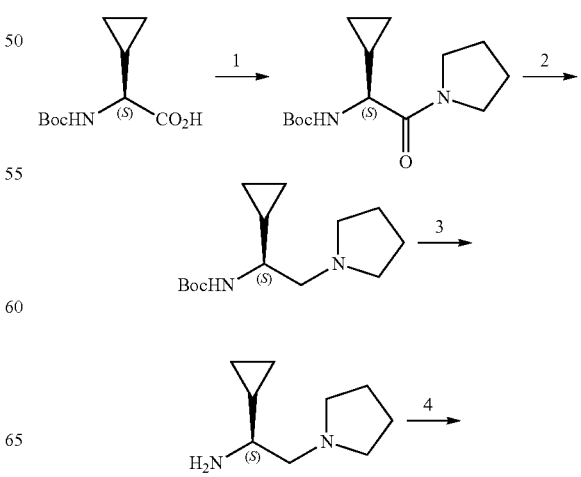

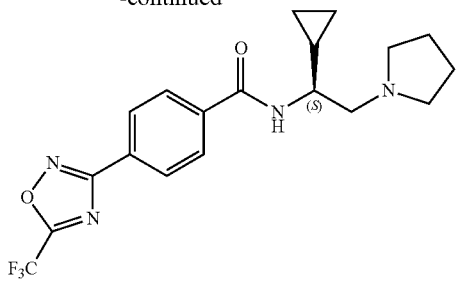

Step 1: (S)-tert-Butyl (1-cyclopropyl-2-oxo-2-(pyrrolidin-1-yl)ethyl)carbamate

Following method A from (S)-2-((tert-butoxycarbonyl)amino)-2-cyclopropylacetic acid (1.0 g, 4.65 mmol) and pyrrolidine (0.58 mL, 6.98 mmol) gave the title compound as a colorless oil which was progressed to the next step without further purification.

Step 2: (S)-tert-Butyl (1-cyclopropyl-2-(pyrrolidin-1-yl)ethyl)carbamate

Following method B from (S)-tert-butyl (1-cyclopropyl-2-oxo-2-(pyrrolidin-1-yl)ethyl)carbamate (1.53 g, 5.7 mmol) gave the title compound which was used without further purification.

Step 3: (S)-1-Cyclopropyl-2-(pyrrolidin-1-yl)ethanamine

Following method C from (S)-tert-butyl (1-cyclopropyl-2-(pyrrolidin-1-yl)ethyl)carbamate (920 mg, 3.62 mmol). The free amine was isolated by dissolving the residue obtained after aqueous work-up in DCM/MeOH (1:1, 5 mL) and passing it through an SCX cartridge (elution with DCM:MeOH:7M $NH_3$ in MeOH (1:1:0.05). The title compound was obtained as an orange oil (390 mg, 70%).

Step 4: (S)—N-(1-Cyclopropyl-2-(pyrrolidin-1-yl)ethyl)-4-(5-(trifluoromethyl)-1,2,4-oxadiazol-3-yl)benzamide Following method A from (S)-1-cyclopropyl-2-(pyrrolidin-1-yl)ethanamine (134 mg, 0.87 mmol) and 4-(5-(trifluoromethyl)-1,2,4-oxadiazol-3-yl)benzoic acid (150 mg, 0.58 mmol). LCMS (ES+) 395 (M+H)+, RT 2.67 min (Analytical method 1). $^1$H NMR δ (ppm) (400 MHz, DMSO-$d_6$) 8.42 (1H, d, J=8.7 Hz), 8.15 (2H, d, J=8.4 Hz), 8.05 (2H, d, J=8.5 Hz), 3.71-3.63 (1H, m), 2.80 (1H, dd, J=9.1, 12.1 Hz), 2.52-2.49 (3H, m), 2.48-2.40 (2H, m), 1.62 (4H, s), 1.02-0.93 (1H, m), 0.50-0.43 (1H, m), 0.36-0.29 (2H, m), 0.24-0.17 (1H, m).

Example 6: (R)—N-(1-Cyclopropyl-2-(pyrrolidin-1-yl)ethyl)-4-(5-(trifluoromethyl)-1,2,4-oxadiazol-3-yl)benzamide

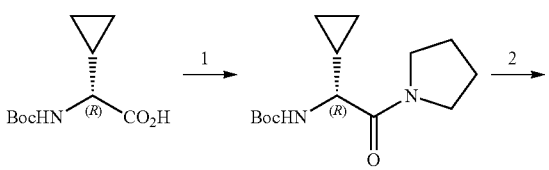

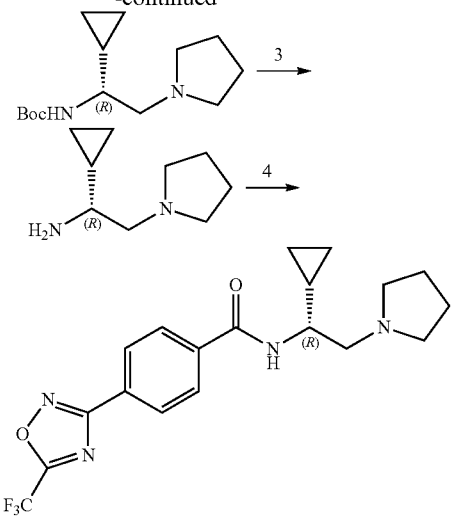

Step 1: (R)-tert-Butyl (1-cyclopropyl-2-oxo-2-(pyrrolidin-1-yl)ethyl)carbamate

Following method A from (R)-2-((tert-butoxycarbonyl)amino)-2-cyclopropylacetic acid (1.64 g, 7.62 mmol) and pyrrolidine (0.95 mL, 11.4 mmol) gave the title compound as a colorless oil which was progressed to the next step without further purification.

Step 2: (R)-tert-Butyl (1-cyclopropyl-2-(pyrrolidin-1-yl)ethyl)carbamate

Following method B from (R)-tert-butyl (1-cyclopropyl-2-oxo-2-(pyrrolidin-1-yl)ethyl)carbamate (1.02 g, 3.81 mmol) gave the title compound which was used without further purification.

Step 3: (R)-1-Cyclopropyl-2-(pyrrolidin-1-yl)ethanamine

Following method C from (R)-tert-butyl (1-cyclopropyl-2-(pyrrolidin-1-yl)ethyl)carbamate (860 mg, 3.39 mmol). The free amine was isolated by dissolving the residue obtained after aqueous work-up in DCM/MeOH (1:1, 5 mL) and passing it through an SCX cartridge (elution with DCM:MeOH:7M $NH_3$ in MeOH (1:1:0.05). The title compound was obtained as an orange oil (190 mg, 36%).

Step 4: (R)—N-(1-Cyclopropyl-2-(pyrrolidin-1-yl)ethyl)-4-(5-(trifluoromethyl)-1,2,4-oxadiazol-3-yl)benzamide Following method A from (R)-1-cyclopropyl-2-(pyrrolidin-1-yl)ethanamine (190 mg, 1.23 mmol) and 4-(5-(trifluoromethyl)-1,2,4-oxadiazol-3-yl)benzoic acid (212 mg, 0.82 mmol). LCMS (ES+) 395 (M+H)+, RT 2.69 min (Analytical method 1). $^1$H NMR δ (ppm) (400 MHz, DMSO-$d_6$) 8.42 (1H, d, J=8.7 Hz), 8.15 (2H, d, J=8.4 Hz), 8.05 (2H, d, J=8.5 Hz), 3.71-3.63 (1H, m), 2.80 (1H, dd, J=9.1, 12.1 Hz), 2.52-2.49 (3H, m), 2.48-2.40 (2H, m), 1.62 (4H, s), 1.02-0.93 (1H, m), 0.50-0.43 (1H, m), 0.36-0.29 (2H, m), 0.24-0.17 (1H, m).

Example 7: (R)—N-(1-(3,4-Dihydroisoquinolin-2 (1H)-yl)propan-2-yl)-4-(5-(trifluoromethyl)-1,2,4-oxadiazol-3-yl)benzamide

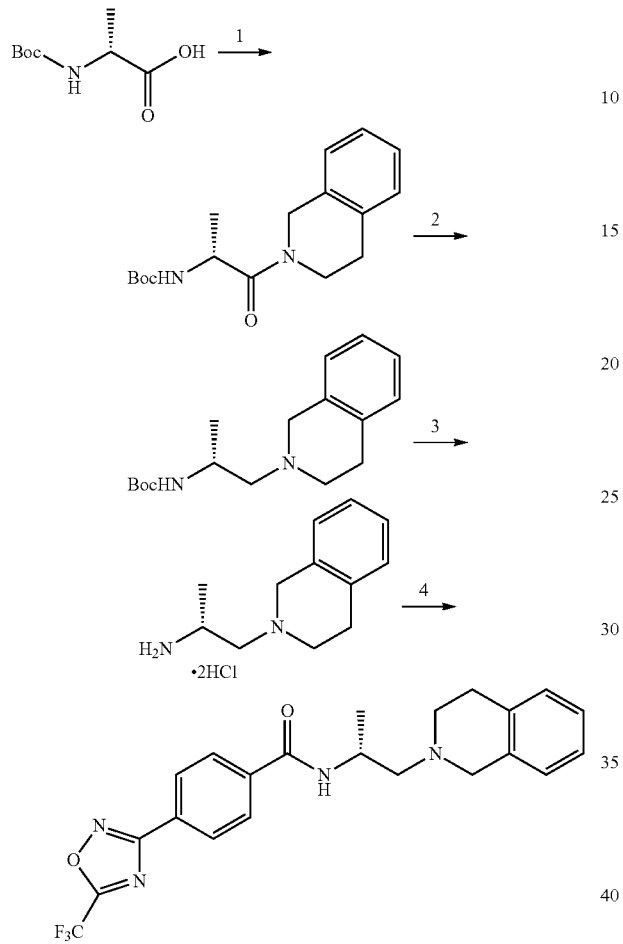

Step 1: (R)-tert-Butyl (1-(3,4-dihydroisoquinolin-2 (1H)-yl)-1-oxopropan-2-yl)carbamate Following method A from (R)-2-((tert-butoxycarbonyl) amino)propanoic acid (720 mg, 3.78 mmol) and 1,2,3,4-tetrahydroisoquinoline (0.52 mL, 4.016 mmol). Purification by column chromatography (gradient elution, 0 to 100% EtOAc in i-hex) gave the title compound as a pale yellow gum (1.01 g, 87%).

Step 2: (R)-tert-Butyl (1-(3,4-dihydroisoquinolin-2 (1H)-yl)propan-2-yl)carbamate Following method B from (1-(3,4-dihydroisoquinolin-2 (1H)-yl)-1-oxopropan-2-yl)carbamate (1.01 g, 3.31 mmol) gave the title compound as a pale yellow gum (0.86 mg, 89%).

Step 3: (R)-1-(3,4-Dihydroisoquinolin-2(1H)-yl) propan-2-amine dihydrochloride Following method C from (R)-tert-butyl (1-(3,4-dihydroisoquinolin-2(1H)-yl)propan-2-yl)carbamate (860 mg, 2.96 mmol) gave the title compound as a pale orange glass (788 mg, >99%). This was used in the next step without further purification.

Step 4: (R)—N-(1-(3,4-Dihydroisoquinolin-2(1H)-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (636 mg, 2.46 mmol) and (R)-1-(3,4-dihydroisoquinolin-2(1H)-yl)propan-2-amine dihydrochloride (778 mg, 2.96 mmol) and DIPEA (2.2 mL, 12.3 mmol) were added and the mixture stirred for 18 h. The mixture was washed with water, passed through a phase separation cartridge and concentrated to yield the crude product. This residue was purified by preparative-HPLC and then further purified by chiral SFC to give the title compound as a white solid. LCMS (ES+) 431 (M+H)+, RT 2.80 min (Analytical Method 1); $^1$H NMR δ (ppm) (400 MHz, DMSO-$d_6$) 8.47 (1H, d, J=8.2 Hz), 8.16 (2H, d, J=8.5 Hz), 8.06 (2H, d, J=8.7 Hz), 7.12-7.04 (4H, m), 4.40-4.32 (1H, m), 3.63 (2H, s), 2.82-2.62 (6H, m), 1.22 (3H, d, J=6.5 Hz).

Example 8: (R)—N-(1-(3-Phenylazetidin-1-yl)propan-2-yl)-4-(5-(trifluoromethyl)-1,2,4-oxadiazol-3-yl)benzamide

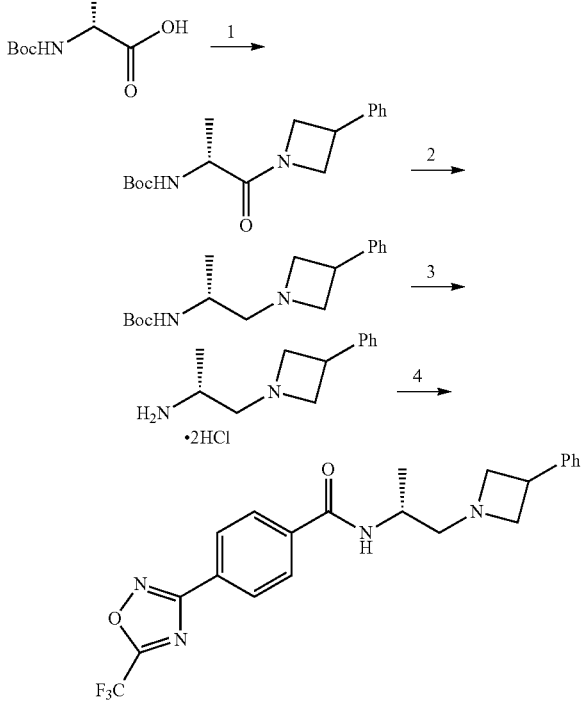

Step 1: (R)-tert-Butyl (1-oxo-1-(3-phenylazetidin-1-yl)propan-2-yl)carbamate Following method A from (R)-2-((tert-butoxycarbonyl) amino)propanoic acid (649 mg, 3.41 mmol) 3-phenylazetidine (0.5 g, 3.75 mmol). Purification by column chromatography (gradient elution, 0 to 100% EtOAc/i-hex) gave the title compound as a colorless gum (0.87 g, 83%).

Step 2: (R)-tert-Butyl (1-(3-phenylazetidin-1-yl)propan-2-yl)carbamate

Following method B from (R)-tert-butyl (1-oxo-1-(3-phenylazetidin-1-yl)propan-2-yl)carbamate (0.87 g, 2.86 mmol). Purification by column chromatography (gradient elution, 0 to 100% EtOAc/i-hex) gave the title compound as a colorless oil (370 mg, 44%).

Step 3: (R)-1-(3-Phenylazetidin-1-yl)propan-2-amine dihydrochloride

Following method C from (R)-tert-butyl (1-(3-phenylazetidin-1-yl)propan-2-yl)carbamate (370 mg, 1.27 mmol gave the title compound as an off white solid (337 mg, >99%). The material was progressed to the next step without further purification.

Step 4: (R)—N-(1-(3-Phenylazetidin-1-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (252 mg, 0.98 mmol) and (R)-1-(3-phenylazetidin-1-yl)propan-2-amine dihydrochloride (348 mg, 1.07 mmol). After work up the crude material was recrystallized from diisopropyl ether three times to give the title compound as a white solid (71 mg, 16%). LCMS (ES+) 431 (M+H)$^+$, RT 2.83 min (Analytical Method 1); $^1$H NMR δ (ppm) (400 MHz, DMSO-d$_6$) 8.42 (1H, d, J=8.0 Hz), 8.17 (2H, d, J=8.4 Hz), 8.07 (2H, d, J=8.5 Hz), 7.35-7.28 (4H, m), 7.23-7.18 (1H, m), 4.11-4.00 (1H, m), 3.75-3.57 (3H, m), 3.20-3.07 (2H, m), 2.68-2.57 (1H, m), 1.18 (3H, d, J=6.8 Hz). One proton obscured by DMSO peak.

Example 9 and Example 10: D1: N—((R)-1-((abs)-3-(Difluoromethoxy)piperidin-1-yl)propan-2-yl)-4-(5-(trifluoromethyl)-1,2,4-oxadiazol-3-yl)benzamide; and D2: N—((R)-1-((abs)-3-(difluoromethoxy)piperidin-1-yl)propan-2-yl)-4-(5-(trifluoromethyl)-1,2,4-oxadiazol-3-yl)benzamide

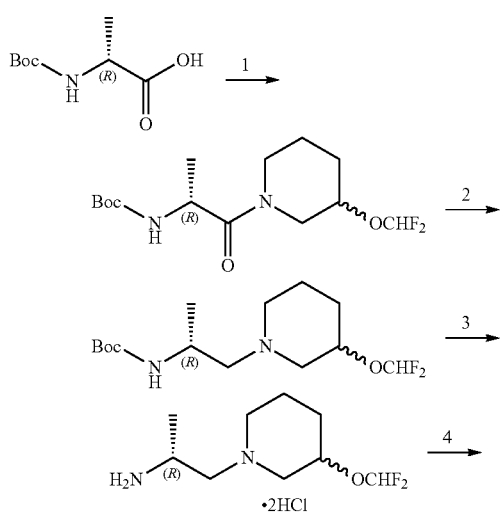

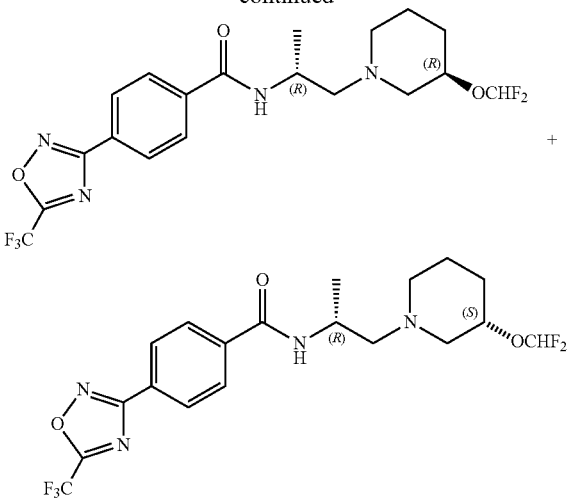

Step 1: tert-Butyl ((2R)-1-(3-(difluoromethoxy)piperidin-1-yl)-1-oxopropan-2-yl)carbamate Following Method A from (R)-2-((tert-butoxycarbonyl)amino)propanoic acid (284 mg, 1.50 mmol) and (±)-3-(difluoromethoxy)piperidine (250 mg, 1.65 mmol). The title compound was obtained as a yellow gum (424 mg, 87%) and used in the next step without further purification.

Step 2: tert-Butyl ((2R)-1-(3-(difluoromethoxy)piperidin-1-yl)propan-2-yl)carbamate Following method B from tert-butyl ((2R)-1-(3-(difluoromethoxy)piperidin-1-yl)-1-oxopropan-2-yl)carbamate (420 mg, 1.30 mmol). The title compound was obtained as a pale yellow gum (234 mg, 58%).

Step 3: (2R)-1-(3-(Difluoromethoxy)piperidin-1-yl)propan-2-amine dihydrochloride Following method C from tert-butyl ((2R)-1-(3-(difluoromethoxy)piperidin-1-yl)propan-2-yl)carbamate (234 mg, 0.76 mmol). The title compound was obtained as a pale yellow foam (210 mg, 98%).

Step 4: D1: N—((R)-1-((abs)-3-(Difluoromethoxy)piperidin-1-yl)propan-2-yl)-4-(5-(trifluoromethyl)-1,2,4-oxadiazol-3-yl)benzamide; and D2: N—((R)-1-((abs)-3-(difluoromethoxy)piperidin-1-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (178 mg, 0.69 mmol) and (2R)-1-(3-(difluoromethoxy)piperidin-1-yl)propan-2-amine dihydrochloride (210 mg, 0.76 mmol). The crude material was purified by preparative HPLC and chiral preparative SFC (LUX Cellulose-4, 5/95 IPA/CO$_2$, 5.0 ml/min, 120 bar, 40° C. to give the title compounds as white solids. D1: N—((R)-1-((abs)-3-(difluoromethoxy)piperidin-1-yl)propan-2-yl)-4-(5-(trifluoromethyl)-1,2,4-oxadiazol-3-yl)benzamide (50 mg, 16%): LCMS (ES+) 449 (M+H)$^+$, RT 2.74 min (Analytical Method 1); SFC RT 4.48 min; $^1$H NMR δ (ppm) (400 MHz, DMSO-d$_6$) 8.40 (1H, d, J=8.3 Hz), 8.17 (2H, d, J=8.5 Hz), 8.05 (2H, d, J=8.5 Hz), 6.72 (1H, t, J=76.3 Hz), 4.27-4.16 (1H, m), 4.10-4.01 (1H, m), 2.91 (1H, dd, J=3.0, 10.4 Hz), 2.68-2.60 (1H, m), 2.35 (1H, dd, J=7.0, 12.4 Hz), 2.19-2.05 (2H, m), 1.91-1.82 (1H, m), 1.71-1.63 (1H, m), 1.47-1.27 (2H, m), 1.16 (3H, d, J=6.5 Hz). 1 proton obscured by DMSO peak. D2: N—((R)-1-((abs)-3-(difluoromethoxy)piperidin-1-yl)propan-2-yl)-4-(5-(trifluoromethyl)-1,2,4-oxadiazol-3-yl)benzamide (53 g, 17%): LCMS (ES+)449 (M+H)$^+$, RT 2.72 min (Analytical Method 1); SFC RT 7.49 min; $^1$H NMR δ (ppm) (400 MHz, DMSO-d$_6$) 8.40 (1H, d, J=8.2 Hz), 8.17 (2H, d, J=8.5 Hz), 8.05 (2H, d, J=8.5 Hz), 6.73 (1H, t, J=76.4 Hz), 4.27-4.16 (1H, m), 4.11-4.02 (1H, m), 2.92 (1H, dd, J=3.3, 10.6 Hz), 2.72-2.67 (1H, m), 2.35 (1H, dd, J=6.7, 12.5 Hz), 2.15-2.02 (2H, m), 1.92-1.83 (1H, m), 1.70-1.62 (1H, m), 1.46-1.25 (2H, m), 1.16 (3H, d, J=6.7 Hz). 1 proton obscured by DMSO peak.

Example 11: (R)—N-(1-(5-Azaspiro[2.5]octan-5-yl)propan-2-yl)-4-(5-(trifluoromethyl)-1,2,4-oxadiazol-3-yl)benzamide

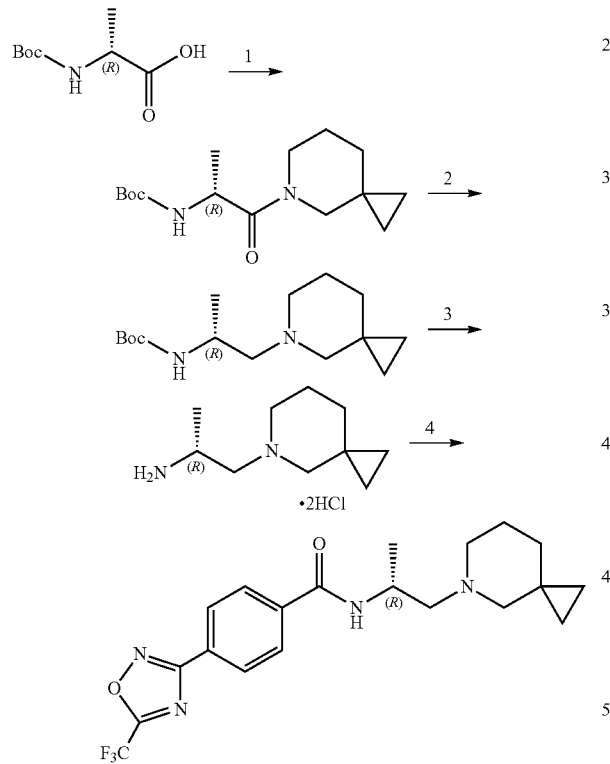

Step 1: (R)-tert-Butyl (1-oxo-1-(5-azaspiro[2.5]octan-5-yl)propan-2-yl)carbamate To a stirred solution of (R)-2-((tert-butoxycarbonyl)amino)propanoic acid (648 mg, 3.43 mmol) in DMF (10 mL) was added HBTU (1.43 g, 3.73 mmol), 5-azaspiro[2.5]octane hydrochloride (500 mg, 3.43 mmol) and DIPEA (3.16 mL, 17.1 mmol). The mixture was stirred at r.t. overnight. The mixture was washed with water, passed through a phase separation cartridge and concentrated to give the title compound (1.01 g) which was used in the next step without further purification.

Step 2: (R)-tert-Butyl (1-(5-azaspiro[2.5]octan-5-yl)propan-2-yl)carbamate

Following method B from (R)-tert-butyl (1-oxo-1-(5-azaspiro[2.5]octan-5-yl)propan-2-yl)carbamate (1.01 g, 3.58 mmol) gave the title compound which was used in the next step without further purification.

Step 3: (R)-1-(5-Azaspiro[2.5]octan-5-yl)propan-2-amine dihydrochloride

Following method C from (R)-tert-butyl (1-(5-azaspiro[2.5]octan-5-yl)propan-2-yl)carbamate (866 mg, 2.29 mmol) gave the title compound which was used in the next step without further purification.

Step 4: (R)—N-(1-(5-Azaspiro[2.5]octan-5-yl)propan-2-yl)-4-(5-(trifluoromethyl)-1,2,4-oxadiazol-3-yl)benzamide Using the same method as in step 1 from 4-(5-(trifluoromethyl)-1,2,4-oxadiazol-3-yl)benzoic acid (590 mg, 2.29 mmol) and (R)-1-(5-azaspiro[2.5]octan-5-yl)propan-2-amine dihydrochloride (770 mg, 2.29 mmol). The title compound was obtained as a white solid. LCMS (ES+) 409 (M+H)$^+$, RT 3.58 min (Analytical Method 2); $^1$H NMR δ (ppm) (400 MHz, DMSO-d$_6$) 8.38 (1H, d, J=8.2 Hz), 8.19 (2H, d, J=8.5 Hz), 8.07 (2H, d, J=8.5 Hz), 4.24-4.16 (1H, m), 2.49-2.41 (2H, m), 2.29 (1H, dd, J=7.2, 12.2 Hz), 2.18 (2H, dd, J=11.8, 17.5 Hz), 1.63-1.57 (2H, m), 1.32-1.22 (3H, m), 1.17 (3H, d, J=6.5 Hz), 0.31-0.22 (4H, m).

Example 12: (R)—N-(1-(6-Azaspiro[2.5]octan-6-yl)propan-2-yl)-4-(5-(trifluoromethyl)-1,2,4-oxadiazol-3-yl)benzamide

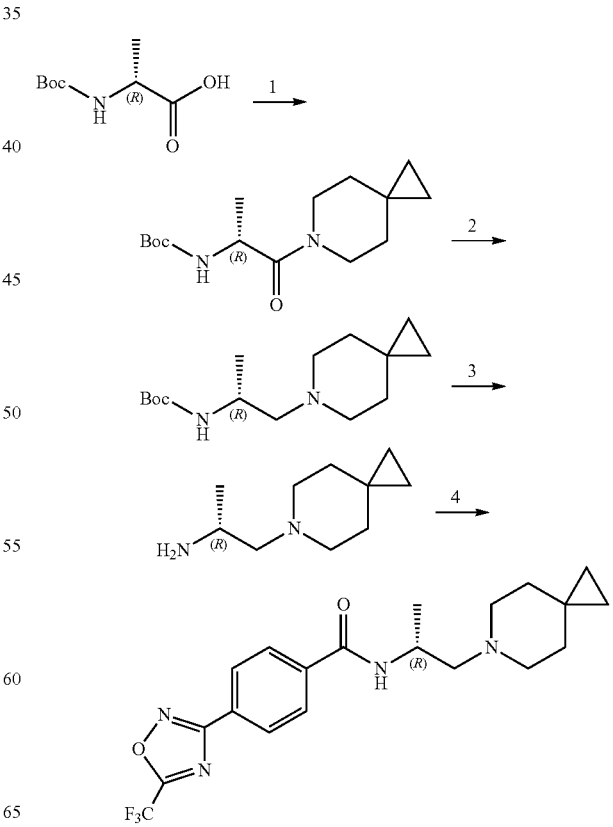

Step 1: (R)-tert-Butyl (1-oxo-1-(6-azaspiro[2.5]octan-6-yl)propan-2-yl)carbamate A flask was charged with (R)-2-((tert-butoxycarbonyl)amino)propanoic acid (250 mg, 1.32 mmol), 6-azaspiro[2.5]octane (150 mg, 1.32 mmol), HATU (602 mg, 1.60 mmol) and anhydrous DMF (5 mL). The reaction mixture was stirred until a pale yellow solution formed and then DIPEA (350 µL, 2.0 mmol) was added and the mixture stirred overnight. The reaction mixture was diluted with EtOAc (25 mL), washed with 1 M HCl (15 mL), sat. NaHCO$_3$ (15 mL) then brine (15 mL). The organics were dried (MgSO$_4$), filtered and concentrated. Purification by column chromatography (gradient elution, 0 to 66% EtOAc in i-hex) gave the title compound as a colorless oil (339 mg, 91%) which solidifies on standing.

Step 2: (R)-tert-Butyl (1-(6-azaspiro[2.5]octan-6-yl)propan-2-yl)carbamate

Following method B (using THF instead of Et$_2$O) from (R)-tert-butyl (1-oxo-1-(6-azaspiro[2.5]octan-6-yl)propan-2-yl)carbamate (320 mg, 1.13 mmol) gave the title compound as a pale yellow oil (260 mg, 86%).

Step 3: (R)-1-(6-Azaspiro[2.5]octan-6-yl)propan-2-amine

To a solution of (R)-tert-butyl (1-(6-azaspiro[2.5]octan-6-yl)propan-2-yl)carbamate (220 mg, 0.82 mmol) in anhydrous DCM (10 mL) was added TFA (1.5 mL). The reaction mixture was stirred at r.t. for 48 h. The mixture was concentrated under reduced pressure and passed through an SCX cartridge (elution with MeOH:7 M NH$_3$ in MeOH (4:1)). The basic fractions were concentrated to give the title compound as a brown oil (120 mg, 85%).

Step 4: (R)—N-(1-(6-Azaspiro[2.5]octan-6-yl)propan-2-yl)-4-(5-(trifluoromethyl)-1,2,4-oxadiazol-3-yl)benzamide Following the same method as for step 1 from 4-(5-(trifluoromethyl)-1,2,4-oxadiazol-3-yl)benzoic acid (124 mg, 0.48 mmol) and (R)-1-(6-azaspiro[2.5]octan-6-yl)propan-2-amine (80 mg, 0.48 mmol). Purification by preparative HPLC gave the title compound as an colorless solid. LCMS (ES+) 409 (M+H)$^+$, RT 2.77 min (Analytical Method 1); $^1$H NMR δ (ppm) (400 MHz, DMSO-d$_6$) 8.16 (1H, d, J=8.1 Hz), 7.96-7.90 (2H, m), 7.82 (2H, d, J=8.3 Hz), 4.00 (1H, t, J=7.2 Hz), 3.10 (4H, br s), 2.2.30-2.20 (5H, s), 2.14-2.08 (1H, m), 1.08 (4H, s), 0.93 (3H, t, J=6.6 Hz).

Example 13: (R)—N-(1-(Azepan-1-yl)propan-2-yl)-4-(5-(trifluoromethyl)-1,2,4-oxadiazol-3-yl)benzamide

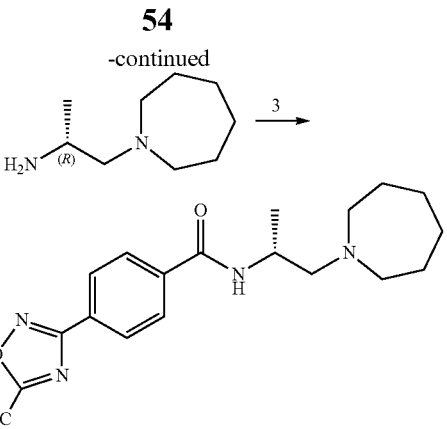

Step 1: (R)-tert-Butyl (1-(azepan-1-yl)propan-2-yl)carbamate

Following method D from intermediate 1 (1.0 g, 3.95 mmol) and azepane (890 µL, 7.91 mmol) gave the title compound as a yellow oil (489 mg, 48%).

Step 2: (R)-1-(Azepan-1-yl)propan-2-amine

To a solution of (R)-tert-butyl (1-(azepan-1-yl)propan-2-yl)carbamate (489 mg, 1.91 mmol) in anhydrous DCM (40 mL) was added TFA (0.8 mL). The reaction mixture was stirred at r.t. for 2 h. The mixture was concentrated under reduced pressure and passed through an SCX cartridge (elution with MeOH:7 M NH$_3$ in MeOH (4:1)). The basic fractions were concentrated to give the title compound as a yellow oil (310 mg, >99%).

Step 3: (R)—N-(1-(Azepan-1-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (427 mg, 1.65 mmol) and (R)-1-(azepan-1-yl)propan-2-amine (310 mg, 1.91 mmol). Purification by preparative-HPLC and SFC gave the title compound as a white solid (45 mg). LCMS (ES+) 397 (M+H)$^+$, RT 2.70 min (Analytical Method 1); $^1$H NMR δ (ppm) (400 MHz, DMSO-d$_6$) 8.35 (1H, d, J=8.2 Hz), 8.17 (2H, d, J=8.7 Hz), 8.05 (2H, d, J=8.5 Hz), 4.17-4.09 (1H, m), 2.68-2.59 (5H, m), 2.45 (1H, dd, J=7.0, 12.4 Hz), 1.58-1.51 (8H, m), 1.16 (3H, d, J=6.7 Hz).

Example 14: (R)—N-(1-(1-Azaspiro[3.3]heptan-1-yl)propan-2-yl)-4-(5-(trifluoromethyl)-1,2,4-oxadiazol-3-yl)benzamide

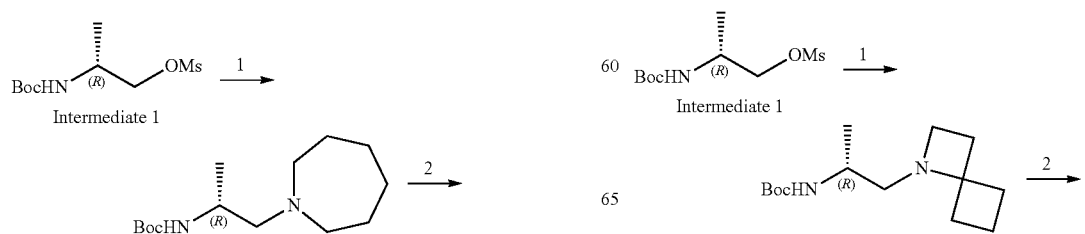

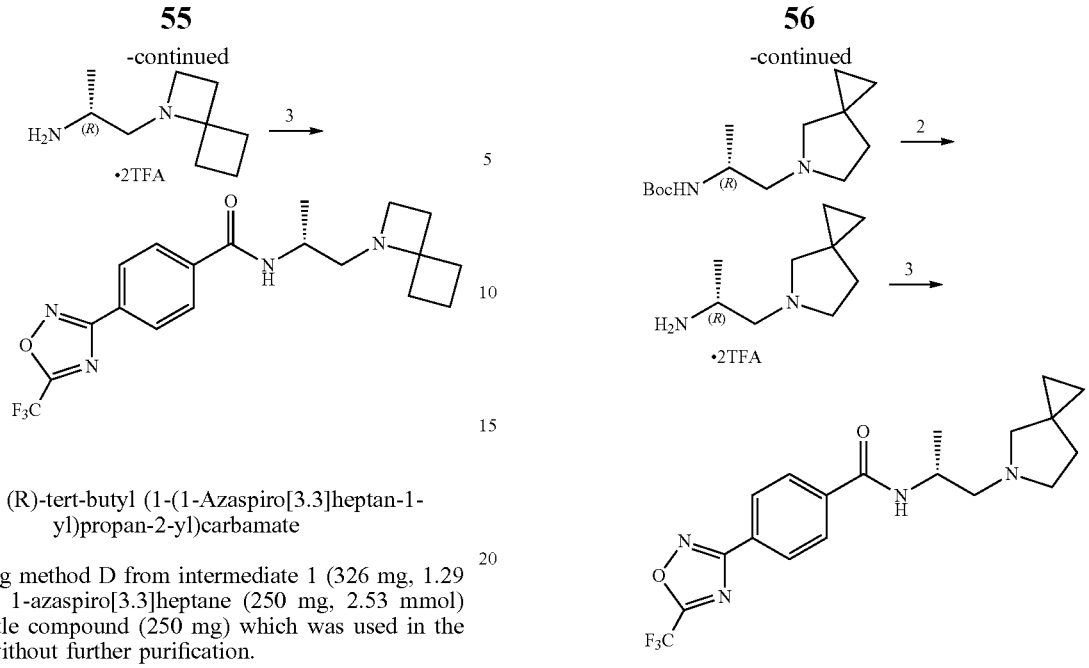

Step 1: (R)-tert-butyl (1-(1-Azaspiro[3.3]heptan-1-yl)propan-2-yl)carbamate

Following method D from intermediate 1 (326 mg, 1.29 mmol) and 1-azaspiro[3.3]heptane (250 mg, 2.53 mmol) gave the title compound (250 mg) which was used in the next step without further purification.

Step 2: 1-((R)-2-Aminopropyl)-1-azaspiro[3.3]heptan-1-ium 2,2,2-trifluoroacetate To a solution of (R)-tert-butyl (1-(1-azaspiro[3.3]heptan-1-yl)propan-2-yl)carbamate (0.25 mg, 1.00 mmol) in anhydrous DCM (2 mL) was added TFA (1 mL). The reaction mixture was stirred at r.t. for 3 h. The mixture was concentrated under reduced pressure to give the title compound (268 mg) which was used in the next step without further purification.

Step 3: (R)—N-(1-(1-Azaspiro[3.3]heptan-1-yl)propan-2-yl)-4-(5-(trifluoromethyl)-1,2,4-oxadiazol-3-yl)benzamide A flask was charged with (R)-2-((tert-butoxycarbonyl)amino)propanoic acid (260 mg, 1.00 mmol), 1-((R)-2-aminopropyl)-1-azaspiro[3.3]heptan-1-ium 2,2,2-trifluoroacetate (268 mg, 1.00 mmol), HATU (690 mg, 1.5 mmol), DMAP (30 mg) and anhydrous DMF (5 mL). The reaction mixture was stirred until a pale yellow solution formed and then DIPEA (1.5 mL, 72.0 mmol) was added and the mixture stirred overnight. The reaction mixture was diluted with DCM, washed with water passed through a phase separator, filtered and concentrated. Purification by preparative-HPLC and SFC gave the title compound as a white solid (12 mg). LCMS (ES+) 395 (M+H)+, RT 2.65 min (Analytical Method 1); $^1$H NMR δ (ppm) (400 MHz, DMSO-$d_6$) 8.42 (1H, d, J=8.1 Hz), 8.21 (2H, d, J=8.6 Hz), 8.11 (2H, d, J=8.6 Hz), 4.11-4.02 (1H, m), 3.15-3.08 (2H, m), 2.63 (1H, dd, J=6.4, 11.7 Hz), 2.49 (1H, dd, J=7.1, 11.9 Hz), 2.27-2.09 (4H, m), 1.90 (2H, m), 1.64-1.56 (2H, m), 1.21 (3H, d, J=6.8 Hz).

Example 15: (R)—N-(1-(5-Azaspiro[2.4]heptan-5-yl)propan-2-yl)-4-(5-(trifluoromethyl)-1,2,4-oxadiazol-3-yl)benzamide Step 1: (R)-tert-butyl (1-(5-Azaspiro[2.4]heptan-5-yl)propan-2-yl)carbamate Following method D from intermediate 1 (237 mg, 0.90 mmol) and 5-azaspiro[2.4]heptan-5-ium chloride (250 mg, 1.80 mmol) gave the title compound (100 mg) which was used in the next step without further purification.

Step 2: 5-((R)-2-Aminopropyl)-5-azaspiro[2.4]heptan-5-ium 2,2,2-trifluoroacetate To a solution of (R)-tert-butyl (1-(1-azaspiro[3.3]heptan-1-yl)propan-2-yl)carbamate (0.25 mg, 1.00 mmol) in anhydrous DCM (2 mL) was added TFA (1 mL). The reaction mixture was stirred at r.t. for 3 h. The mixture was concentrated under reduced pressure to give the title compound (268 mg) which was used in the next step without further purification.

Step 3: (R)—N-(1-(1-Azaspiro[3.3]heptan-1-yl)propan-2-yl)-4-(5-(trifluoromethyl)-1,2,4-oxadiazol-3-yl)benzamide A flask was charged with (R)-2-((tert-butoxycarbonyl)amino)propanoic acid (260 mg, 1.00 mmol), (R)-1-(1-azaspiro[3.3]heptan-1-yl)propan-2-amine (268 mg, 1.00 mmol), HATU (690 mg, 1.5 mmol), DMAP (30 mg) and anhydrous DMF (5 mL). The reaction mixture was stirred until a pale yellow solution formed and then DIPEA (1.5 mL, 72.0 mmol) was added and the mixture stirred overnight. The reaction mixture was diluted with DCM, washed with water passed through a phase separator, filtered and concentrated. Purification by preparative-HPLC and SFC gave the title compound as a white solid (12 mg). LCMS (ES+) 395 (M+H)+, RT 2.65 min (Analytical Method 1); $^1$H NMR δ (ppm) (400 MHz, DMSO-$d_6$) 8.48 (1H, d, J=8.1 Hz), 8.22 (2H, d, J=8.6 Hz), 8.12 (2H, d, J=8.3 Hz), 4.24-4.16 (1H, m), 2.73 (2H, dd, J=6.9, 6.9 Hz), 2.62 (2H, dd, J=7.3, 11.6 Hz), 2.52-2.48 (2H, m), 1.79-1.74 (2H, m), 1.23 (3H, d, J=6.6 Hz), 0.54 (4H, dd, J=7.6, 18.9 Hz).

Example 16: N-((2R)-1-(3-Azabicyclo[3.2.1]octan-3-yl)propan-2-yl)-4-(5-(trifluoromethyl)-1,2,4-oxadiazol-3-yl)benzamide

Example 17: 2-((R)-2-(4-(5-(Trifluoromethyl)-1,2,4-oxadiazol-3-yl)benzamido)propyl)octahydrocyclopenta[c]pyrrol-2-ium formate

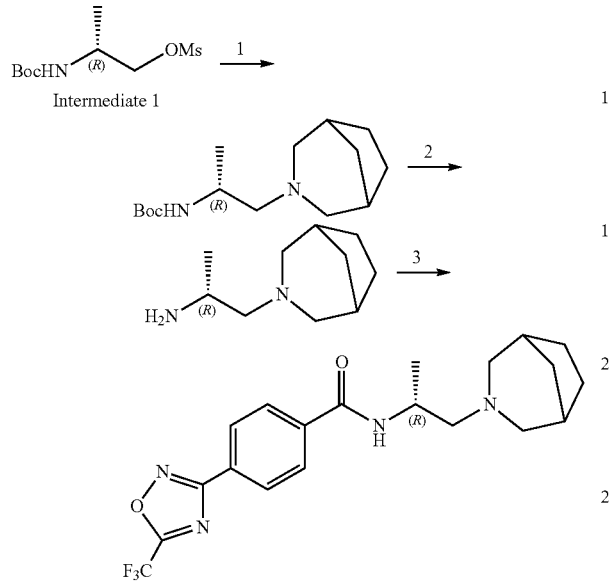

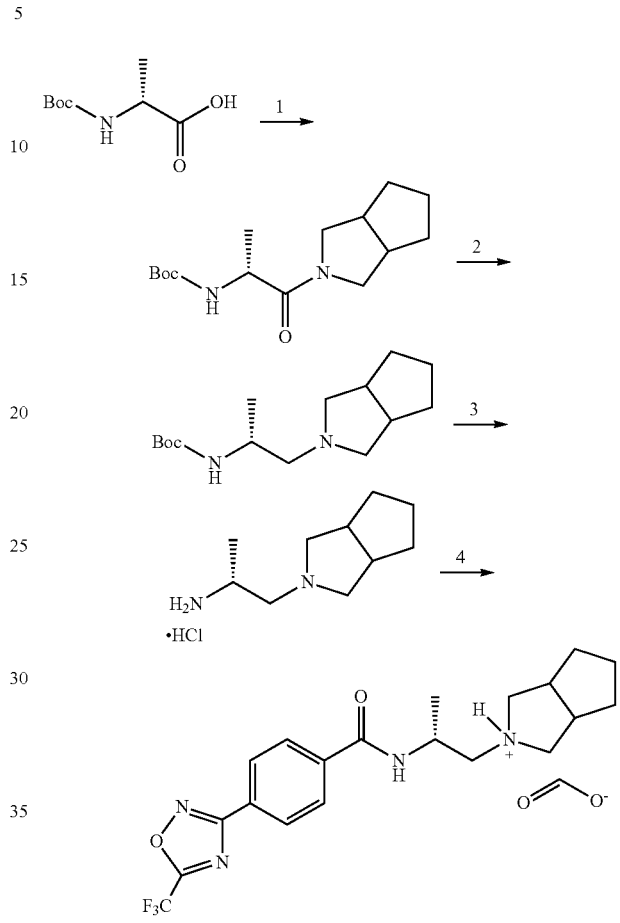

Step 1: tert-Butyl ((R)-1-((1R,5S)-3-azabicyclo[3.2.1]octan-3-yl)propan-2-yl)carbamate Following method D from intermediate 1 (736 mg, 2.90 mmol) and (1R,5S)-3-azabicyclo[3.2.1]octane (730 mg, 4.94 mmol) gave the title compound (186 mg, 21%) which was used in the next step without further purification.

Step 2: (R)-1-((1R,5S)-3-Azabicyclo[3.2.1]octan-3-yl)propan-2-amine

To a solution of tert-butyl ((R)-1-((1R,5S)-3-azabicyclo[3.2.1]octan-3-yl)propan-2-yl)carbamate (186 mg, 0.62 mmol) in anhydrous DCM (2.5 mL) was added TFA (0.5 mL). The reaction mixture was stirred at r.t. for 3 h. The mixture was concentrated under reduced pressure and passed through an SCX cartridge (elution with MeOH:7 M $NH_3$ in MeOH (4:1)). The basic fractions were concentrated to give the title compound (80 mg) which was used in the next step without further purification.

Step 3: N—((R)-1-((1R,5S)-3-Azabicyclo[3.2.1]octan-3-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (122 mg, 0.47 mmol) and (R)-1-(3-azabicyclo[3.2.1]octan-3-yl)propan-2-amine (80 mg, 0.47 mmol).

Purification by preparative-HPLC and SFC gave the title compound as a white solid (33 mg). LCMS (ES+) 409 $(M+H)^+$, RT 2.81 min (Analytical Method 1); $^1H$ NMR δ (ppm) (400 MHz, DMSO-$d_6$) 8.31 (1H, d, J=8.3 Hz), 8.17 (2H, d, J=8.7 Hz), 8.05 (2H, d, J=8.5 Hz), 4.24-4.16 (1H, m), 2.73-2.61 (2H, m), 2.41 (1H, dd, J=8.3, 12.2 Hz), 2.26 (1H, dd, J=6.7, 12.2 Hz), 2.11-1.99 (4H, m), 1.55-1.36 (5H, m), 1.29 (1H, d, J=10.4 Hz), 1.15 (3H, d, J=6.5 Hz).

Step 1: tert-Butyl ((2R)-1-(hexahydrocyclopenta[c]pyrrol-2(1H)-yl)-1-oxopropan-2-yl)carbamate Following method A from (R)-2-((tert-butoxycarbonyl)amino)propanoic acid (0.77 g, 4.09 mmol) and octahydrocyclopenta[c]pyrrole (0.50 g, 4.5 mmol) gave the title compound as a yellow gum (1.08 g, 93%). The compound was impure but used in the next step without further purification.

Step 2: tert-Butyl ((2R)-1-(hexahydrocyclopenta[c]pyrrol-2(1H)-yl)-1-oxopropan-2-yl)carbamate Following method B from tert-butyl ((2R)-1-(hexahydrocyclopenta[c]pyrrol-2(1H)-yl)-1-oxopropan-2-yl)carbamate (1.08 g, 3.82 mmol) gave the title compound as a pale yellow gum (0.61 g, 59%). The compound was impure but used in the next step without further purification.

Step 3: (2R)-1-(Hexahydrocyclopenta[c]pyrrol-2(1H)-yl)propan-2-amine hydrochloride Following method C from tert-butyl ((2R)-1-(hexahydrocyclopenta[c]pyrrol-2(1H)-yl)-1-oxopropan-2-yl)carbamate (0.61 g, 2.27 mmol) gave the title compound as a pale yellow foam (274 mg, >100%). This was used in the next step without further purification.

Step 4: 2-((R)-2-(4-(5-(Trifluoromethyl)-1,2,4-oxadiazol-3-yl)benzamido)propyl)octahydrocyclopenta[c]pyrrol-2-ium formate Following method A from 4-(5-(trifluoromethyl)-1,2,4-oxadiazol-3-yl)benzoic acid (0.48 g, 1.89 mmol). Purification by column chromatography using gradient elution 0-20% methanol in DCM gave a pale orange solid (700 mg). This was purified further by preparative HPLC to give the title compound as a pale orange glass (142 mg). LCMS (ES+) 409 (M+H)$^+$, RT 2.74 min (Analytical Method 1); $^1$H NMR δ (ppm) (400 MHz, DMSO-$d_6$) 8.40 (1H, d, J=8.2 Hz), 8.19-8.15 (3H, m), 8.05 (2H, d, J=8.5 Hz), 4.23-4.11 (1H, m), 2.60 (2H, q, J=7.5 Hz), 2.49-2.43 (3H, m), 2.43-2.38 (1H, m), 2.25 (2H, ddd, J=3.9, 8.4, 12.0 Hz), 1.59-1.52 (3H, m), 1.41-1.29 (3H, m), 1.17 (3H, d, J=6.7 Hz).

Example 18: (R)—N-(1-(3,4-dihydro-2,7-naphthyridin-2(1H)-yl)propan-2-yl)-4-(5-(trifluoromethyl)-1,2,4-oxadiazol-3-yl)benzamide

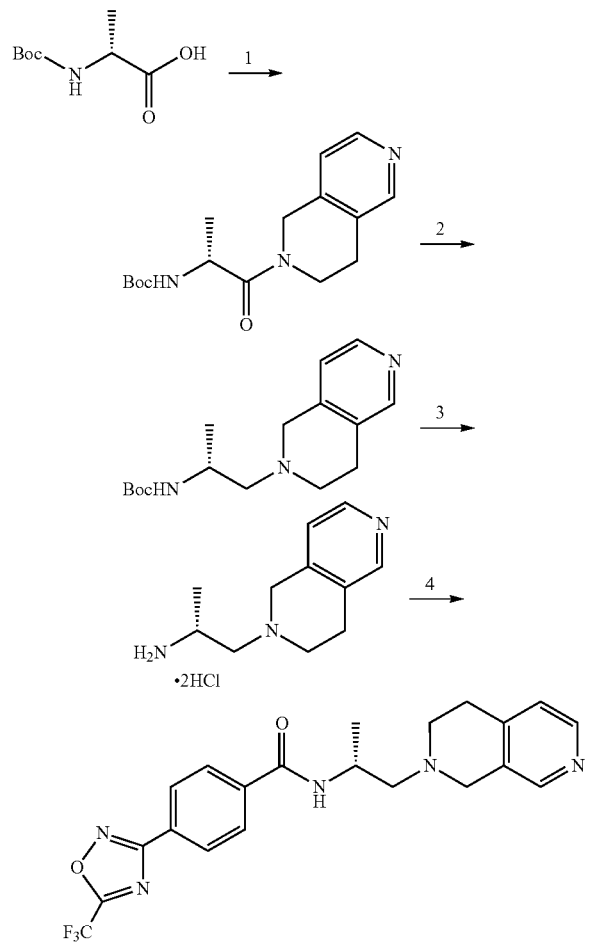

Step 1: (R)-tert-Butyl (1-(3,4-dihydro-2,6-naphthyridin-2(1H)-yl)-1-oxopropan-2-yl)carbamate Following method A from (R)-2-((tert-butoxycarbonyl)amino)propanoic acid (1.28 g, 6.78 mmol) and 1,2,3,4-tetrahydro-2,6-naphthyridine (1.0 g, 7.45 mmol). The title compound was obtained as a pale yellow gum (2.43 g, >100%). This was used crude in the next step.

Step 2: (R)-tert-Butyl (1-(3,4-dihydro-2,6-naphthyridin-2(1H)-yl)propan-2-yl)carbamate Following method B from (R)-tert-butyl (1-(3,4-dihydro-2,6-naphthyridin-2(1H)-yl)-1-oxopropan-2-yl)carbamate (2.43 g, 7.96 mmol). The mixture was purified by passing through an SCX cartridge (elution with MeOH:7 M NH$_3$ in MeOH (9:1)). This gave the title compound as a pale yellow gum (810 mg, 34%). The product was used in the next step without further purification.

Step 3: (R)-1-(3,4-Dihydro-2,6-naphthyridin-2(1H)-yl)propan-2-amine trihydrochloride Following method C from (R)-tert-butyl (1-(3,4-dihydro-2,6-naphthyridin-2(1H)-yl)propan-2-yl)carbamate (810 mg, 2.78 mmol) gave the title compound as a pale orange glass (0.98 mg, >100%). This was used in the next step without further purification.

Step 4: (R)—N-(1-(3,4-Dihydro-2,7-naphthyridin-2(1H)-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (650 mg, 2.5 mmol) and (R)-1-(3,4-dihydro-2,6-naphthyridin-2(1H)-yl)propan-2-amine trihydrochloride (980 mg, 2.78 mmol) and DIPEA (2.2 mL, 12.5 mmol) were added and the mixture stirred for 18 h. The mixture was washed with water, passed through a phase separation cartridge and concentrated to yield the crude product. Purification by preparative-HPLC gave the title compound as an off white solid (162 mg). LCMS (ES+) 432 (M+H)$^+$, RT 2.41 min (Analytical Method 1); $^1$H NMR δ (ppm) (400 MHz, DMSO-$d_6$) 8.48 (1H, d, J=8.2 Hz), 8.29 (1H, s), 8.26 (1H, d, J=5.0 Hz), 8.16 (3H, d, J=7.8 Hz), 8.06 (2H, d, J=8.5 Hz), 7.11 (1H, d, J=5.1 Hz), 4.42-4.30 (1H, m), 3.66 (2H, s), 2.81-2.64 (6H, m), 1.22 (3H, d, J=6.5 Hz).

Example 19: N-((2R)-1-(3-Azabicyclo[3.2.0]heptan-3-yl)propan-2-yl)-4-(5-(trifluoromethyl)-1,2,4-oxadiazol-3-yl)benzamide

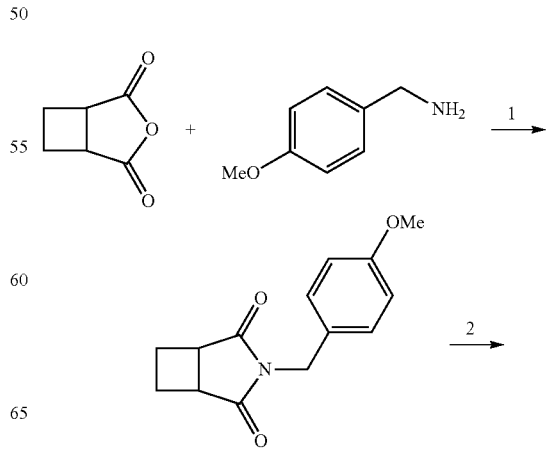

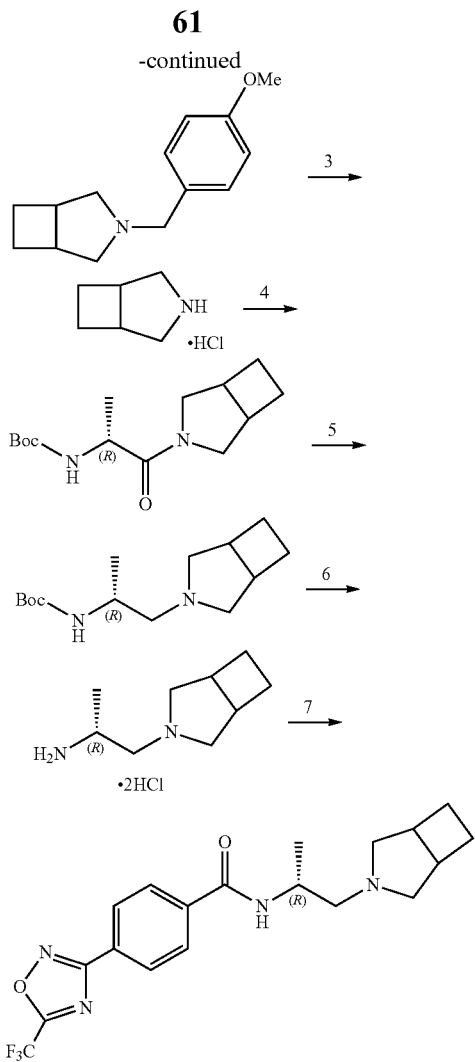

Step 1: 3-(4-Methoxybenzyl)-3-azabicyclo[3.2.0]heptane-2,4-dione

4-Methoxy benzylamine (1.04 mL, 7.93 mmol) was added dropwise at 0° C. to a solution of 3-oxabicyclo[3.2.0]heptane-2,4-dione (1.0 g, 7.93 mmol) in THF (3 mL). The semi solid mixture was warmed to 90° C. to remove the THF and the solid slowly melted as the mixture was warmed to 180° C. for 2 h. The solution was cooled to 60° C. and poured into iced DIPE to afford the title compound as a white solid (1.77 g, 91%), which was collected by filtration.

Step 2: 3-(4-Methoxybenzyl)-3-azabicyclo[3.2.0]heptane

Following method B from 3-(4-methoxybenzyl)-3-azabicyclo[3.2.0]heptane-2,4-dione (1.0 g, 4.1 mmol). The reaction was refluxed for 2 h before work-up. This gave the title compound as a pale yellow gum (1.0 g). The product was used in the next step without further purification.

Step 3: 3-Azabicyclo[3.2.0]heptane hydrochloride 3-(4-Methoxybenzyl)-3-azabicyclo[3.2.0]heptane (870 mg, 4.0 mmol) was dissolved in MeOH (100 mL) and 10% Pd/C (870 mg) was added. The mixture was shaken under a hydrogen gas atmosphere (2 bar) for 18 h at r.t. The reaction mixture was then filtered through Celite, acidified with 4 N HCl in dioxane (5 mL) and concentrated to yield the title compound as an off-white glass (590 mg) which was used in the next step without further purification.

Step 4: tert-Butyl ((2R)-1-(3-azabicyclo[3.2.0]heptan-3-yl)-1-oxopropan-2-yl)carbamate Following method A from (R)-2-((tert-butoxycarbonyl)amino)propanoic acid (630 mg, 3.33 mmol) and 3-azabicyclo[3.2.0]heptane hydrochloride (590 mg, 4.0 mmol). The title compound was obtained as a pale yellow gum (490 mg, 55%). This was used crude in the next step.

Step 5: tert-Butyl ((2R)-1-(3-azabicyclo[3.2.0]heptan-3-yl)propan-2-yl)carbamate Following method B from tert-butyl ((2R)-1-(3-azabicyclo[3.2.0]heptan-3-yl)-1-oxopropan-2-yl)carbamate (0.49 g, 1.80 mmol). The mixture was purified by passing through an SCX cartridge (elution with MeOH:7 M $NH_3$ in MeOH (9:1)). This gave the title compound as a pale yellow gum (229 mg, 49%).

Step 6: (2R)-1-(3-Azabicyclo[3.2.0]heptan-3-yl)propan-2-amine hydrochloride

Following method C from tert-butyl ((2R)-1-(3-azabicyclo[3.2.0]heptan-3-yl)propan-2-yl)carbamate (490 mg, 0.90 mmol) gave the title compound as a pale yellow solid (254 mg, >100%). This was used in the next step without further purification.

Step 7: N-((2R)-1-(3-Azabicyclo[3.2.0]heptan-3-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (211 mg, 0.82 mmol) and (2R)-1-(3-azabicyclo[3.2.0]heptan-3-yl)propan-2-amine hydrochloride (254 mg, 0.90 mmol) and DIPEA (0.73 mL, 4.09 mmol) were added and the mixture stirred for 18 h. The mixture was washed with water, passed through a phase separation cartridge and concentrated to yield the crude product. This residue was purified by preparative-HPLC and then further purified by chiral SFC to give the title compound as a white solid (65 mg). LCMS (ES+) 395 (M+H)+, RT 2.71 min (Analytical Method 1); $^1$H NMR δ (ppm) (400 MHz, DMSO-$d_6$) 8.44 (1H, d, J=8.3 Hz), 8.17 (2H, d, J=8.5 Hz), 8.06 (2H, d, J=8.7 Hz), 4.31-4.22 (1H, m), 2.83 (2H, dd, J=9.0, 29.3 Hz), 2.75-2.66 (2H, m), 2.61 (1H, dd, J=7.7, 11.6 Hz), 2.53-2.50 (1H, m, obscured by DMSO), 2.06-1.98 (4H, m), 1.61-1.56 (2H, m), 1.25 (3H, d, J=6.5 Hz).

Example 20 and 21: D1: N—((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide; and D2: N—((R)-1-((abs-1,5-cis)-6-azabicyclo[3.2.0]heptan-6-yl)propan-2-yl)-4-(5-(trifluoromethyl)-1,2,4-oxadiazol-3-yl)benzamide

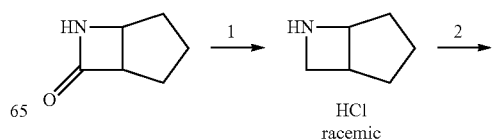

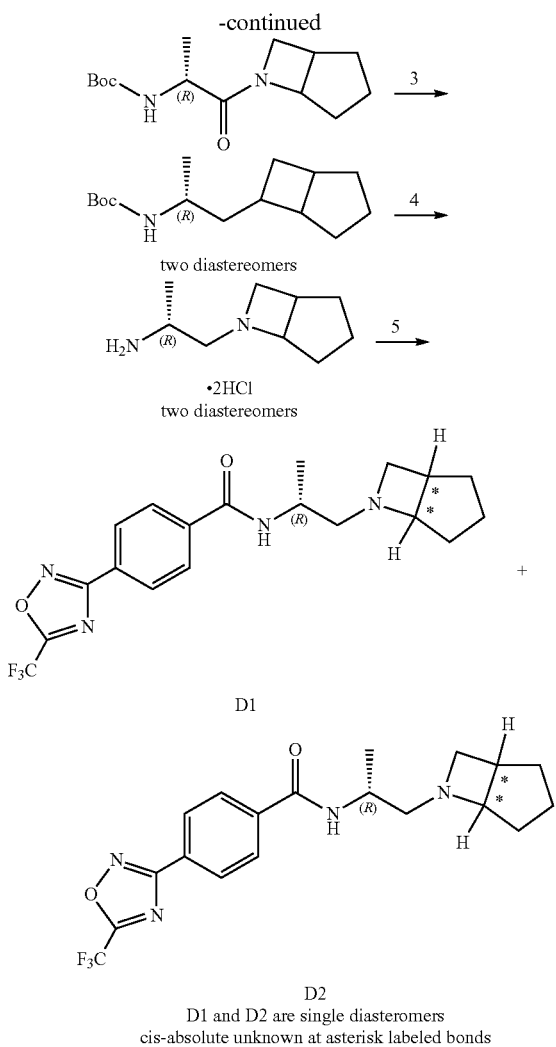

Step 1: 6-Azabicyclo[3.2.0]heptane hydrochloride

A solution of the azabicyclo[3.2.0]heptan-7-one (500 mg, 4.49 mmol) in diethyl ether (9 mL) was added dropwise over 0.5 h to a refluxing solution of LiAlH₄ (5.6 mL, 11.2 mmol) in diethyl ether (36 mL). The reaction mixture was refluxed for 24 h, cooled to 0° C., then water (3 mL), 2 N NaOH solution (4 mL) and water (8 mL) were added sequentially. The reaction was warmed to r.t. and stirred for 30 min, then MgSO₄ was added and the reaction was filtered through Celite, washing well with EtOAc. The filtrate was acidified with 4 N HCl in dioxane (5 mL) and concentrated to give the title compound as an opaque gum (270 mg, 45%). The crude material was taken on to the next step without further purification.

Step 2: tert-Butyl ((2R)-1-(6-azabicyclo[3.2.0]heptan-6-yl)-1-oxopropan-2-yl)carbamate Following method A from (R)-2-((tert-butoxycarbonyl)amino)propanoic acid (1.28 mg, 6.78 mmol) and 6-azabicyclo[3.2.0]heptane hydrochloride (270 mg, 2.78 mmol). The title compound was obtained as a pale yellow gum (0.61 mg, 89%). This was used crude in the next step.

Step 3: tert-Butyl ((2R)-1-(bicyclo[3.2.0]heptan-6-yl)propan-2-yl)carbamate (two diastereomers)

Following method B from tert-butyl ((2R)-1-(6-azabicyclo[3.2.0]heptan-6-yl)-1-oxopropan-2-yl)carbamate (0.61 g, 2.27 mmol). The mixture was purified by passing through an SCX cartridge (elution with MeOH:7 M NH₃ in MeOH (9:1)). This gave a mixture of two diastereomers of the title compound as a pale yellow gum (250 mg, 43%).

Step 4: (2R)-1-(6-Azabicyclo[3.2.0]heptan-6-yl)propan-2-amine dihydrochloride (two diastereomers)

Following method C from tert-butyl ((2R)-1-(bicyclo[3.2.0]heptan-6-yl)propan-2-yl)carbamate (250 mg, 0.97 mmol) gave a mixture of two diastereomers of the title compound as a pale yellow solid (257 mg). This was used in the next step without further purification.

Step 5: D1: N—((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide; and D2: N—((R)-1-((abs-1,5-cis)-6-azabicyclo[3.2.0]heptan-6-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (228 mg, 0.88 mmol) and (2R)-1-(6-azabicyclo[3.2.0]heptan-6-yl)propan-2-amine dihydrochloride (257 mg, 0.98 mmol) and DIPEA (0.79 mL, 4.43 mmol) were added and the mixture stirred for 18 h. The mixture was washed with water, passed through a phase separation cartridge and concentrated to yield the crude product. This residue was purified by preparative-HPLC and then further purified by chiral preparative SFC (LUX CELLUOSE-4 10/90 MeOH (0.1% DEA)/CO₂, 5.0 ml/min, 120 bar, 40° C.) to give the title compounds as white solids. D1: N—((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide (8 mg). LCMS (ES+) 395 (M+H)⁺, RT 3.67 min (Analytical Method 2); ¹H NMR δ (ppm) (400 MHz, DMSO-d₆) 8.34 (1H, br s), 8.17 (2H, d, J=8.3 Hz), 8.05 (2H, d, J=8.4 Hz), 3.93 (1H, br s), 3.73 (1H, br s), 3.14 (1H, br s), 2.98 (1H, br s), 2.76 (1H, br s), 2.63 (1H, br s), 2.47 (1H, br s), 2.02-1.90 (1H, m), 1.78-1.60 (3H, m), 1.46-1.35 (1H, m), 1.13 (4H, d, J=6.5 Hz). D2: N—((R)-1-((abs-1,5-cis)-6-azabicyclo[3.2.0]heptan-6-yl)propan-2-yl)-4-(5-(trifluoromethyl)-1,2,4-oxadiazol-3-yl)benzamide (4 mg). LCMS (ES+) 395 (M+H)⁺, RT 3.67 min (Analytical Method 2); ¹H NMR (400 MHz, DMSO) 8.31 (1H, d, J=8.2 Hz), 8.17 (2H, d, J=8.5 Hz), 8.04 (2H, d, J=8.5 Hz), 3.94-3.86 (1H, m), 3.65 (1H, dd, J=4.7, 6.0 Hz), 3.18 (1H, dd, J=7.9, 7.9 Hz), 2.93 (1H, dd, J=3.3, 7.5 Hz), 2.78-2.72 (1H, m), 2.61 (1H, dd, J=8.1, 11.3 Hz), 2.46 (1H, dd, J=5.9, 11.9 Hz), 1.99-1.90 (1H, m), 1.73-1.56 (3H, m), 1.45-1.34 (1H, m), 1.17-1.13 (1H, m), 1.10 (3H, d, J=6.7 Hz).

Example 22: N-((2R)-1-(6,6-Dimethyl-3-azabicyclo[3.1.0]hexan-3-yl)propan-2-yl)-4-(5-(trifluoromethyl)-1,2,4-oxadiazol-3-yl)benzamide

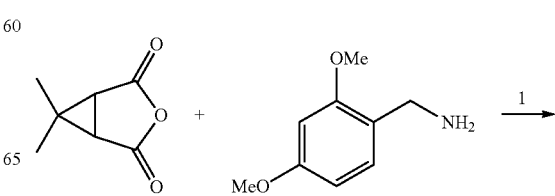

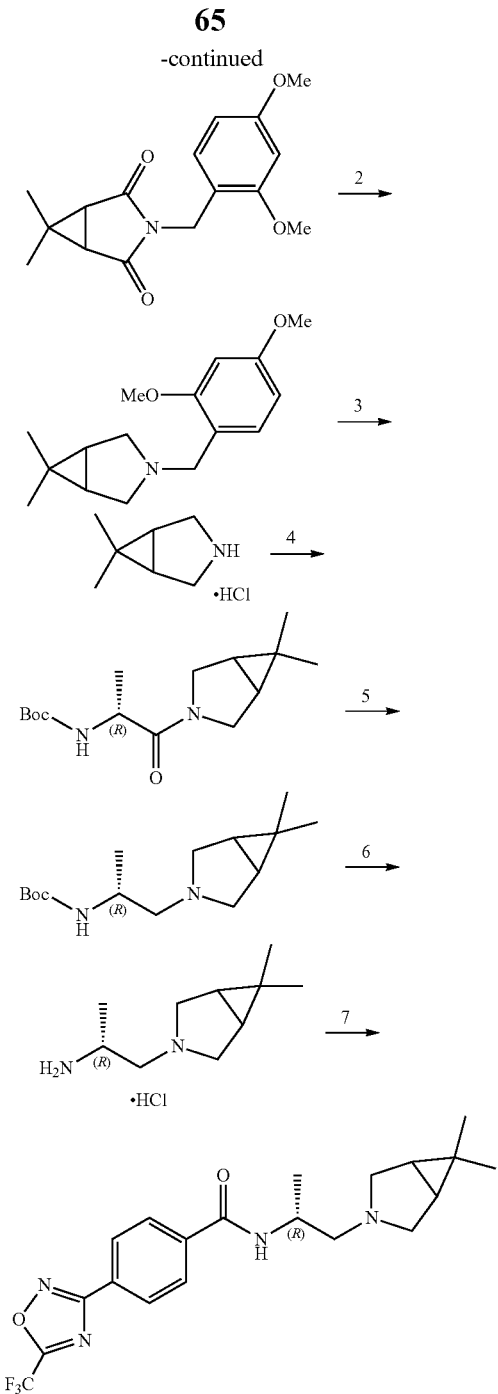

Step 2: 3-(2,4-Dimethoxybenzyl)-6,6-dimethyl-3-azabicyclo[3.1.0]hexane

Following method B from 3-(2,4-dimethoxybenzyl)-3-azabicyclo[3.1.0]hexane-2,4-dione (1.49 g, 5.15 mmol). The reaction was refluxed for 2 h and worked up in the usual way. This gave the title compound as a pale yellow gum (1.31 g). The product was used in the next step without further purification.

Step 3: 6,6-Dimethyl-3-azabicyclo[3.1.0]hexane hydrochloride 3-(2,4-dimethoxybenzyl)-6,6-dimethyl-3-azabicyclo[3.1.0]hexane (1.0 g, 3.83 mmol) was dissolved in methanol (50 mL) and acetic acid (5 mL) then 10% Pd/C (1.0 g) was added. The mixture was shaken under a hydrogen gas atmosphere (5 bar) for 18 h at r.t. The reaction mixture was then filtered through Celite, acidified with 4 N HCl in dioxane (5 mL) and concentrated to yield the title compound as a pale pink solid (1.0 g) which was used in the next step without further purification.

Step 4: tert-Butyl ((2R)-1-(6,6-dimethyl-3-azabicyclo[3.1.0]hexan-3-yl)-1-oxopropan-2-yl)carbamate Following method A from (R)-2-((tert-butoxycarbonyl)amino)propanoic acid (659 mg, 3.48 mmol) and 6,6-dimethyl-3-azabicyclo[3.1.0]hexane hydrochloride (1.0 g, 3.83 mmol). The title compound was obtained as a pale yellow gum (837 mg, 84%). The product was used in the next step without further purification.

Step 5: tert-Butyl ((2R)-1-(6,6-dimethyl-3-azabicyclo[3.1.0]hexan-3-yl)propan-2-yl)carbamate Following method B from tert-butyl ((2R)-1-(6,6-dimethyl-3-azabicyclo[3.1.0]hexan-3-yl)-1-oxopropan-2-yl)carbamate (837 mg, 2.96 mmol). The mixture was purified by passing through an SCX cartridge (elution with MeOH:7 M $NH_3$ in MeOH (9:1)). This gave the title compound as a pale yellow gum (525 mg, 66%).

Step 6: (2R)-1-(6,6-Dimethyl-3-azabicyclo[3.1.0]hexan-3-yl)propan-2-amine hydrochloride Following method C from tert-butyl ((2R)-1-(6,6-dimethyl-3-azabicyclo[3.1.0]hexan-3-yl)propan-2-yl)carbamate (525 mg, 1.96 mmol) gave the title compound as an orange solid (900 mg, >100%). This was used in the next step without further purification.

Step 7: N-((2R)-1-(6,6-Dimethyl-3-azabicyclo[3.1.0]hexan-3-yl)propan-2-yl)-4-(5-(trifluoromethyl)-1,2,4-oxadiazol-3-yl)benzamide Following method A from 4-(5-(trifluoromethyl)-1,2,4-oxadiazol-3-yl)benzoic acid (459 mg, 1.78 mmol) and (2R)-1-(6,6-dimethyl-3-azabicyclo[3.1.0]hexan-3-yl)propan-2-amine hydrochloride (900 mg, 1.95 mmol) and DIPEA (1.6 mL, 8.91 mmol) were added and the mixture stirred for 18 h. The mixture was washed with water, passed through a phase separation cartridge and concentrated to yield the crude product. This residue was purified by preparative-HPLC to afford title compound as an off white solid (138 mg). LCMS (ES+) 409 (M+H)+, RT 4.53 min (Analytical Method 1); $^1$H NMR δ (ppm) (400 MHz, DMSO-$d_6$) 8.33

Step 1: 3-(2,4-Dimethoxybenzyl)-6,6-dimethyl-3-azabicyclo[3.1.0]hexane-2,4-dione 2,4-Dimethoxy benzylamine (1.45 g, 8.67 mmol) was added dropwise at 0° C. to a solution of 6,6-dimethyl-3-oxabicyclo[3.1.0]hexane-2,4-dione (1.21 g, 8.67 mmol) in THF (5 mL). The semi solid mixture was warmed to 90° C. to remove the THF and the solid slowly melted as the mixture was warmed to 180° C. for 2 h. The solution was cooled to 60° C. and poured onto iced DIPE resulting in formation of a gum. This was separated and evaporated to afford the title compound as an orange gum (1.49 g, 59%).

(1H, d, J=8.3 Hz), 8.15 (2H, d, J=8.7 Hz), 8.03 (2H, d, J=8.7 Hz), 4.13-4.04 (1H, m), 2.88 (2H, dd, J=9.2, 24.6 Hz), 2.63-2.54 (3H, m), 2.40 (1H, dd, J=7.0, 11.7 Hz), 1.14-1.10 (8H, m), 0.92 (3H, s).

Example 23: (2S)-1-((R)-2-(3-Fluoro-4-(5-(trifluoromethyl)-1,2,4-oxadiazol-3-yl)benzamido)propyl)-2-methylpyrrolidin-1-ium formate

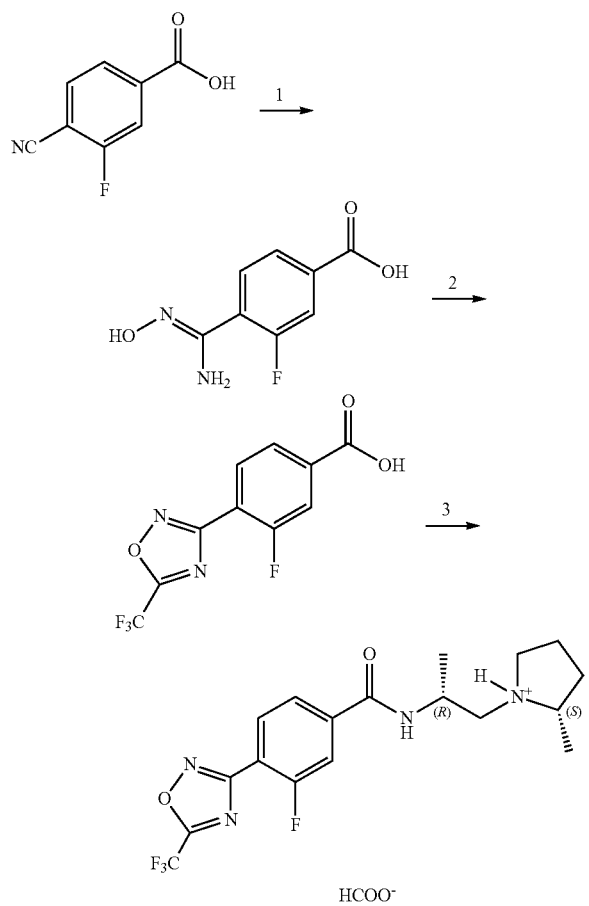

Step 1: (Z)-3-Fluoro-4-(N-hydroxycarbamimidoyl)benzoic acid

To a stirred solution of 4-cyano-3-fluorobenzoic acid (2.00 g, 12.1 mmol) in EtOH (30 mL) was added $NH_2OH \cdot HCl$ (1.18 g, 17.0 mmol) and KOH (2.03 g, 36.3 mmol). The mixture was stirred at r.t. for 17 h, then neutralized with 1 M $HCl_{(aq)}$ and extracted into EtOAc (3×25 mL). The combined organics were dried ($MgSO_4$) and concentrated to give the title compound as a yellow oil which was progressed without further purification.

Step 2: 3-Fluoro-4-(5-(trifluoromethyl)-1,2,4-oxadiazol-3-yl)benzoic acid

To a stirred solution of (Z)-3-fluoro-4-(N-hydroxycarbamimidoyl)benzoic acid (12.1 mmol) in THF (30 mL) was added TFAA (2.50 mL, 18.2 mmol). The mixture was stirred for 3 h and then poured onto ice-water and acidified to pH 4 with 1 M $HCl_{(aq)}$, before extracting into EtOAc (3×30 mL). The combined organics were dried ($MgSO_4$) and concentrated. Purification by flash column chromatography (gradient elution i-hex [+3% AcOH] to 4:1 i-hex:EtOAc [+3% AcOH]) gave the title compound as an off-white solid (150 mg, 4% (2 steps)). LCMS (ES+) 277 (M+H)+.

Step 3: (2S)-1-((R)-2-(3-Fluoro-4-(5-(trifluoromethyl)-1,2,4-oxadiazol-3-yl)benzamido)propyl)-2-methylpyrrolidin-1-ium formate Following method A from 3-fluoro-4-(5-(trifluoromethyl)-1,2,4-oxadiazol-3-yl)benzoic acid (75 mg, 0.27 mmol) and intermediate 2(59 mg, 0.41 mmol). Purification by preparative-HPLC gave the title compound as yellow solid (39 mg, 32%). LCMS (ES+) 447 (M+H)+, RT 2.74 min (Analytical method 1). $^1$H NMR δ (ppm) (400 MHz, DMSO-$d_6$) 8.55 (1H, d, J=8.2 Hz), 8.21-8.17 (2H, m), 7.95-7.91 (2H, m), 4.19-4.09 (1H, m), 3.13 (1H, ddd, J=4.1, 7.2, 8.9 Hz), 2.74 (1H, dd, J=9.3, 11.7 Hz), 2.42-2.34 (1H, m), 2.28 (1H, dd, J=5.7, 11.3 Hz), 2.20 (1H, q, J=8.7 Hz), 1.93-1.83 (1H, m), 1.73-1.63 (2H, m), 1.39-1.25 (1H, m), 1.19 (3H, d, J=6.7 Hz), 1.05 (3H, d, J=6.0 Hz).

Example 24: N—((R)-1-((S)-2-Methylpyrrolidin-1-yl)propan-2-yl)-5-(5-(trifluoromethyl)-1,2,4-oxadiazol-3-yl)picolinamide

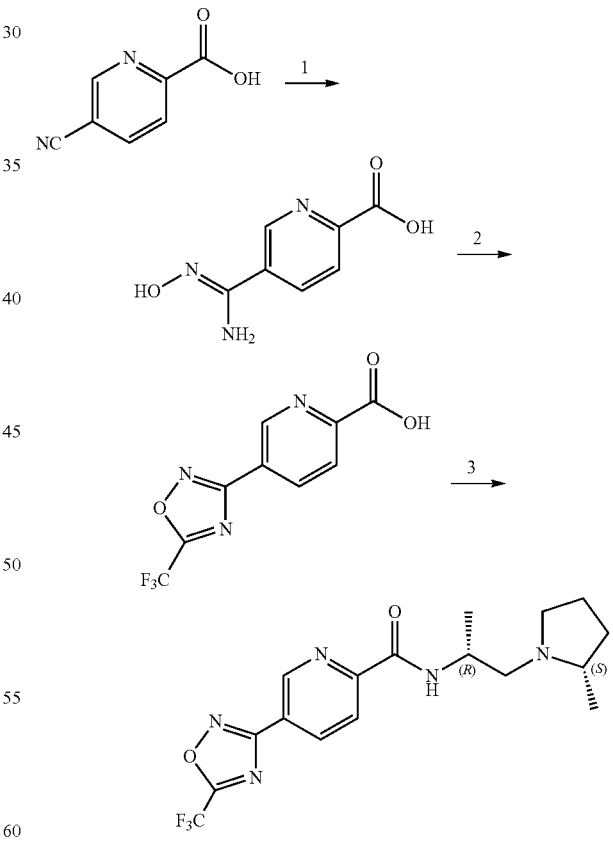

Step 1: (Z)-5-(N-Hydroxycarbamimidoyl)picolinic acid

To a stirred solution of 5-cyanopicolinic acid (1.51 g, 10.2 mmol) in EtOH (30 mL) was added $NH_2OH \cdot HCl$ (999 mg, 14.3 mmol) and KOH (1.71 g, 30.6 mmol). The mixture was stirred at r.t. for 72 h, then neutralized with 1 M HCl$_{(aq)}$. The resulting precipitate was collected by vacuum filtration, washed with H$_2$O and EtOH and dried under vacuum to give the title compound as a white solid (1.21 g, 63%).

Step 2: 5-(5-(Trifluoromethyl)-1,2,4-oxadiazol-3-yl)picolinic acid

To a stirred solution of (Z)-5-(N'-hydroxycarbamimidoyl)picolinic acid (1.21 g, 6.47 mmol) in THF (20 mL) was added TFAA (1.35 mL, 9.71 mmol). The mixture was stirred at r.t. for 17 h and then poured onto ice-water and acidified to pH 4 with 1 M HCl$_{(aq)}$, before extracting into EtOAc (3×30 mL). The combined organics were dried (MgSO$_4$) and concentrated. The residue was taken-up in DCM/MeOH (10 mL, 1:1) and the insoluble solid collected by vacuum filtration to give the title compound as an off-white solid (593 mg, 35%). LCMS (ES+) 260 (M+H)$^+$.

Step 3: N—((R)-1-((S)-2-Methylpyrrolidin-1-yl)propan-2-yl)-5-(5-(trifluoromethyl)-1,2,4-oxadiazol-3-yl)picolinamide Following method A from 5-(5-(trifluoromethyl)-1,2,4-oxadiazol-3-yl)picolinic acid (200 mg, 0.77 mmol) and intermediate 2 (166 mg, 1.16 mmol). Purification by reverse phase chromatography (gradient elution, 5-95% MeCN in 0.1% formic acid) and then passage through SCX cartridge (elution with MeOH:7 M NH$_3$ in MeOH (9:1)) gave the title compound as a orange gum (72 mg, 24%). LCMS (ES+) 384 (M+H)$^+$, RT 3.92 min (Analytical method 2). $^1$H NMR δ (ppm) (400 MHz, DMSO-d$_6$) 9.25 (1H, d, J=1.8 Hz), 8.73 (1H, d, J=8.7 Hz), 8.64 (1H, dd, J=2.1, 8.2 Hz), 8.26 (1H, d, J=8.2 Hz), 4.19-4.09 (1H, m), 3.15-3.07 (1H, m), 2.82 (1H, dd, J=9.0, 11.8 Hz), 2.37-2.28 (1H, m), 2.23 (1H, dd, J=5.1, 10.9 Hz), 2.16 (1H, q, J=8.7 Hz), 1.91-1.80 (1H, m), 1.71-1.61 (2H, m), 1.34-1.23 (1H, m), 1.21 (3H, d, J=6.5 Hz), 1.02 (3H, d, J=6.0 Hz).

Table of examples

| Example | Structure | IUPAC Name |
|---|---|---|
| 1 | 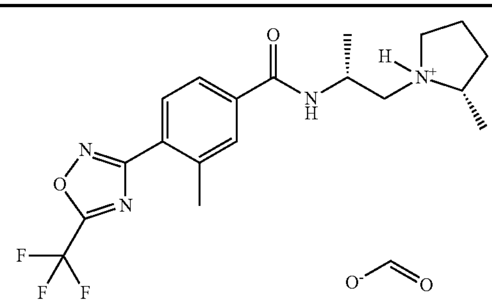 | (2S)-2-Methyl-1-((R)-2-(3-methyl-4-(5-(trifluoromethyl)-1,2,4-oxadiazol-3-yl)benzamido)propyl)pyrrolidin-1-ium formate |
| 2 | 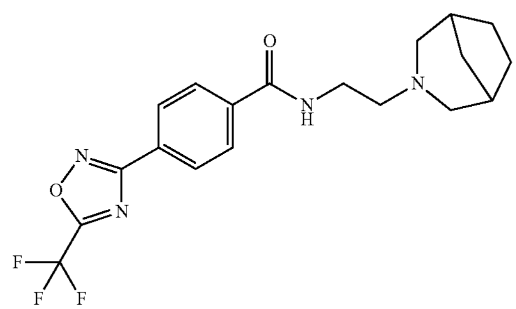 [SMILES: O=C(NCCN1CC2CCC(C2)C1)c1ccc(-c2noc(C(F)(F)F)n2)cc1] | N-(2-(3-Azabicyclo[3.2.1]octan-3-yl)ethyl)-4-(5-(trifluoromethyl)-1,2,4-oxadiazol-3-yl)benzamide |
| 3 | 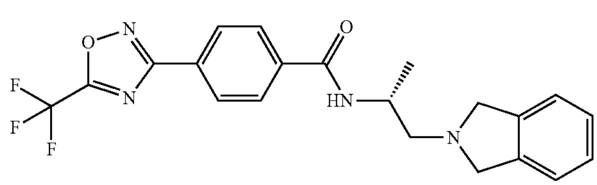 [SMILES: C[C@H](CN1Cc2ccccc2C1)NC(=O)c1ccc(-c2noc(C(F)(F)F)n2)cc1] | (R)-N-(1-(Isoindolin-2-yl)propan-2-yl)-4-(5-(trifluoromethyl)-1,2,4-oxadiazol-3-yl)benzamide |
| 4 | 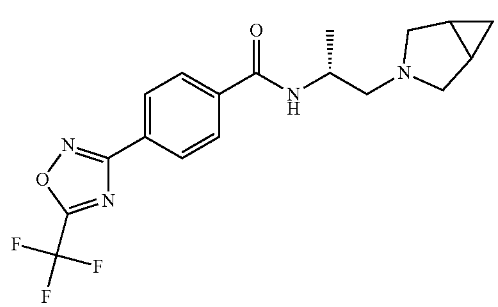 [SMILES: C[C@H](CN1CC2CC2C1)NC(=O)c1ccc(-c2noc(C(F)(F)F)n2)cc1] | N-((2R)-1-(3-Azabicyclo[3.1.0]hexan-3-yl)propan-2-yl)-4-(5-(trifluoromethyl)-1,2,4-oxadiazol-3-yl)benzamide |

Table of examples

| Example | Structure | IUPAC Name |
|---|---|---|
| 5 | 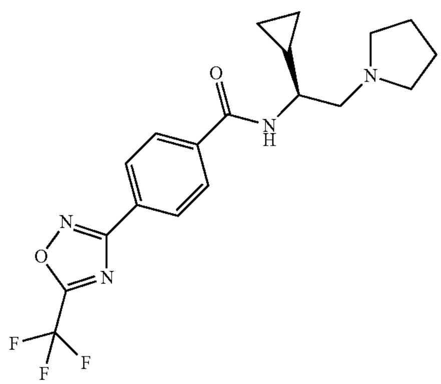 [SMILES: O=C(N[C@H](CN1CCCC1)C1CC1)c1ccc(-c2noc(C(F)(F)F)n2)cc1] | (S)-N-(1-Cyclopropyl-2-(pyrrolidin-1-yl)ethyl)-4-(5-(trifluoromethyl)-1,2,4-oxadiazol-3-yl)benzamide |
| 6 | 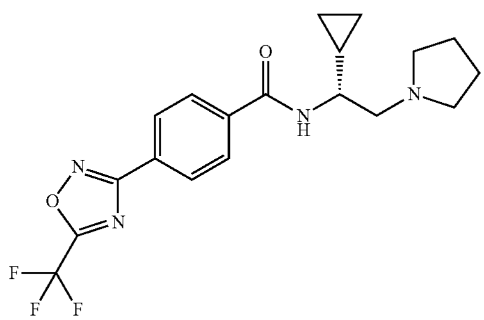 [SMILES: O=C(N[C@@H](CN1CCCC1)C1CC1)c1ccc(-c2noc(C(F)(F)F)n2)cc1] | (R)-N-(1-Cyclopropyl-2-(pyrrolidin-1-yl)ethyl)-4-(5-(trifluoromethyl)-1,2,4-oxadiazol-3-yl)benzamide |
| 7 | 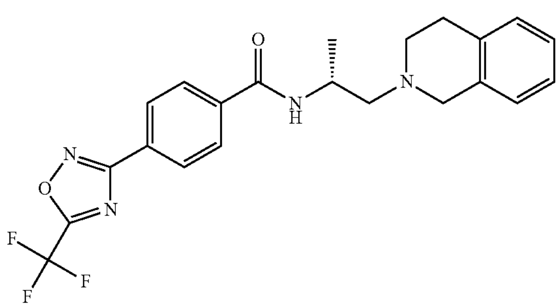 [SMILES: C[C@H](CN1CCc2ccccc2C1)NC(=O)c1ccc(-c2noc(C(F)(F)F)n2)cc1] | (R)-N-(1-(3,4-Dihydroisoquinolin-2(1H)-yl)propan-2-yl)-4-(5-(trifluoromethyl)-1,2,4-oxadiazol-3-yl)benzamide |
| 8 | 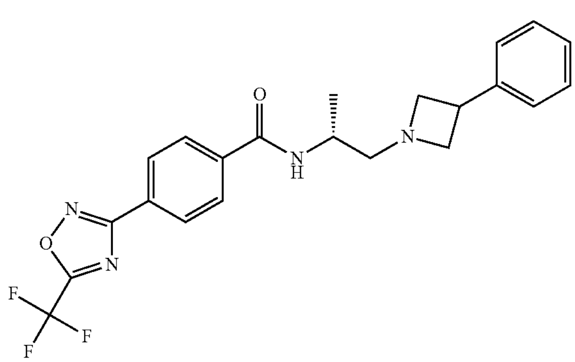 [SMILES: C[C@H](CN1CC(c2ccccc2)C1)NC(=O)c1ccc(-c2noc(C(F)(F)F)n2)cc1] | (R)-N-(1-(3-Phenylazetidin-1-yl)propan-2-yl)-4-(5-(trifluoromethyl)-1,2,4-oxadiazol-3-yl)benzamide |

-continued

Table of examples

| Example | Structure | IUPAC Name |
|---|---|---|
| 9 | 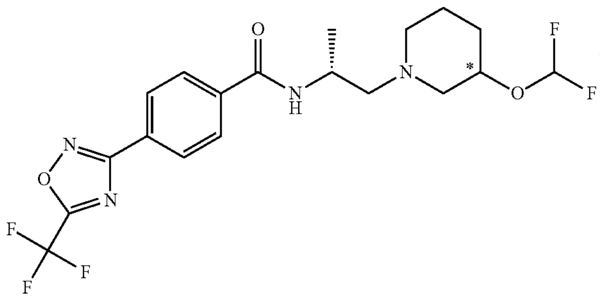 [SMILES: C[C@H](CN1CCCC(OC(F)F)C1)NC(=O)c1ccc(-c2noc(C(F)(F)F)n2)cc1] | D1: N-((R)-1-((abs)-3-(Difluoromethoxy)piperidin-1-yl)propan-2-yl)-4-(5-(trifluoromethyl)-1,2,4-oxadiazol-3-yl)benzamide |
| 10 | 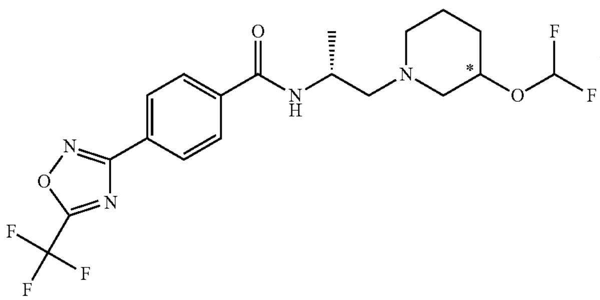 [SMILES: C[C@H](CN1CCCC(OC(F)F)C1)NC(=O)c1ccc(-c2noc(C(F)(F)F)n2)cc1] | D2: N-((R)-1-((abs)-3-(Difluoromethoxy)piperidin-1-yl)propan-2-yl)-4-(5-(trifluoromethyl)-1,2,4-oxadiazol-3-yl)benzamide |
| 11 | 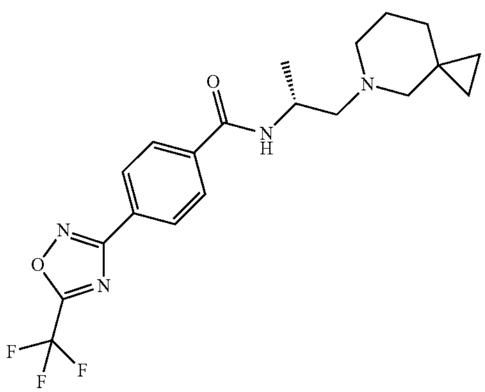 [SMILES: C[C@H](CN1CCCC2(CC2)C1)NC(=O)c1ccc(-c2noc(C(F)(F)F)n2)cc1] | (R)-N-(1-(5-Azaspiro[2.5]octan-5-yl)propan-2-yl)-4-(5-(trifluoromethyl)-1,2,4-oxadiazol-3-yl)benzamide |
| 12 | 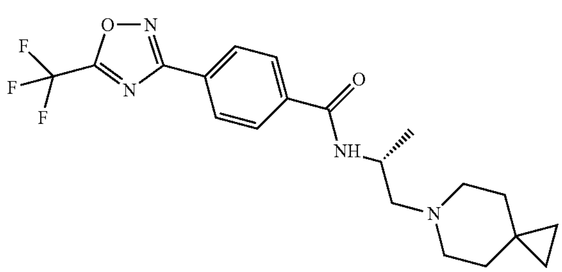 [SMILES: C[C@H](CN1CCC2(CC1)CC2)NC(=O)c1ccc(-c2noc(C(F)(F)F)n2)cc1] | (R)-N-(1-(6-Azaspiro[2.5]octan-6-yl)propan-2-yl)-4-(5-(trifluoromethyl)-1,2,4-oxadiazol-3-yl)benzamide |
| 13 | 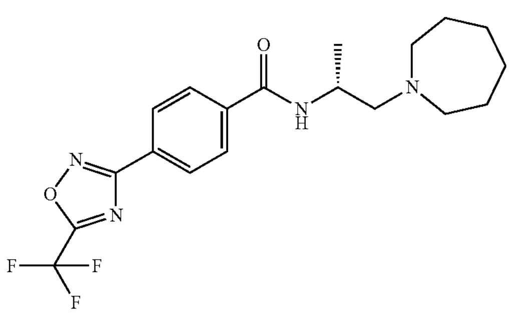 [SMILES: C[C@H](CN1CCCCCC1)NC(=O)c1ccc(-c2noc(C(F)(F)F)n2)cc1] | (R)-N-(1-(Azepan-1-yl)propan-2-yl)-4-(5-(trifluoromethyl)-1,2,4-oxadiazol-3-yl)benzamide |

Table of examples

| Example | Structure | IUPAC Name |
|---|---|---|
| 14 | 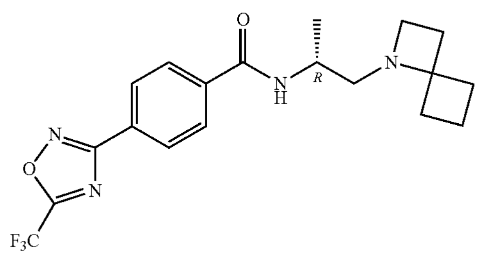 | (R)-N-(1-(1-Azaspiro[3.3]heptan-1-yl)propan-2-yl)-4-(5-(trifluoromethyl)-1,2,4-oxadiazol-3-yl)benzamide |
| 15 | 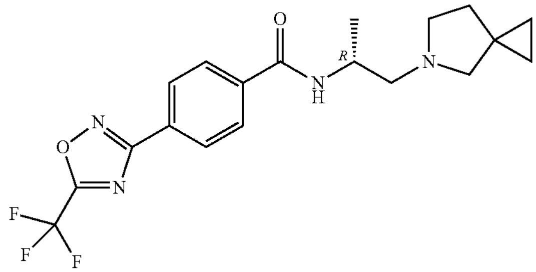 | (R)-N-(1-(5-Azaspiro[2.4]heptan-5-yl)propan-2-yl)-4-(5-(trifluoromethyl)-1,2,4-oxadiazol-3-yl)benzamide |
| 16 | 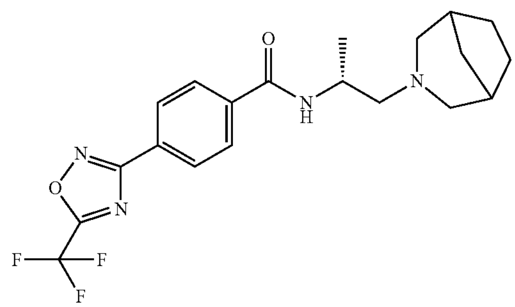 [SMILES: C[C@H](CN1CC2CCC(C2)C1)NC(=O)c1ccc(-c2noc(C(F)(F)F)n2)cc1] | N-((R)-1-(3-Azabicyclo[3.2.1]octan-3-yl)propan-2-yl)-4-(5-(trifluoromethyl)-1,2,4-oxadiazol-3-yl)benzamide |
| 17 | 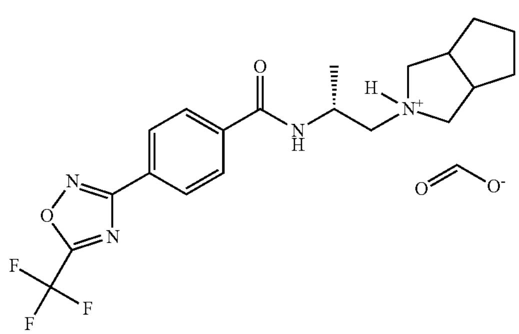 | 2-((R)-2-(4-(5-(Trifluoromethyl)-1,2,4-oxadiazol-3-yl)benzamido)propyl)octahydrocyclopenta[c]pyrrol-2-ium formate |
| 18 | 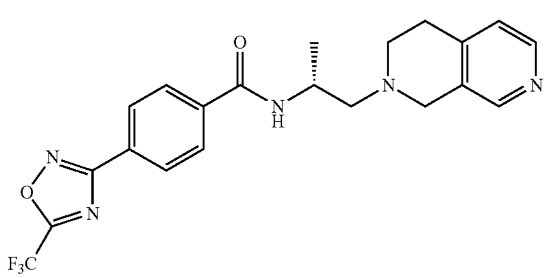 [SMILES: C[C@H](CN1CCc2ccncc2C1)NC(=O)c1ccc(-c2noc(C(F)(F)F)n2)cc1] | (R)-N-(1-(3,4-dihydro-2,7-naphthyridin-2(1H)-yl)propan-2-yl)-4-(5-(trifluoromethyl)-1,2,4-oxadiazol-3-yl)benzamide |

-continued

| Example | Structure | IUPAC Name |
|---|---|---|
| 19 | 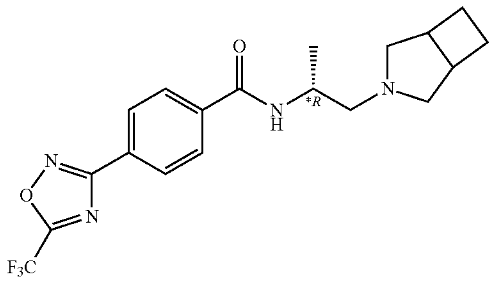 [SMILES: C[C@H](CN1CC2CCC2C1)NC(=O)c1ccc(-c2noc(C(F)(F)F)n2)cc1] | N-((2R)-1-(3-Azabicyclo[3.2.0]heptan-3-yl)propan-2-yl)-4-(5-(trifluoromethyl)-1,2,4-oxadiazol-3-yl)benzamide |
| 20 | 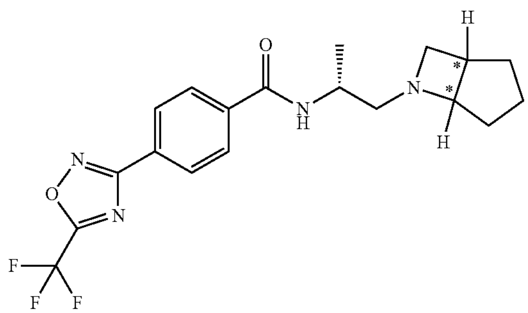 [SMILES: C[C@H](CN1CC2CCCC21)NC(=O)c1ccc(-c2noc(C(F)(F)F)n2)cc1] | D1: N-((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide |
| 21 | 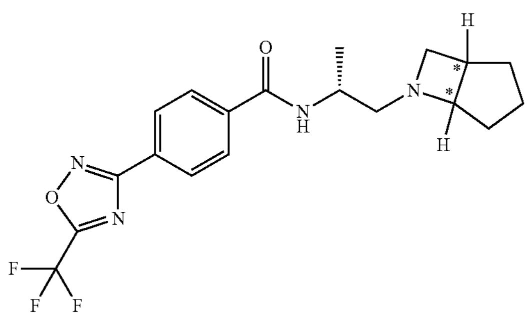 [SMILES: C[C@H](CN1CC2CCCC21)NC(=O)c1ccc(-c2noc(C(F)(F)F)n2)cc1] | D2: N-((R)-1-((abs-1,5-cis)-6-Azabicyclo[3.2.0]heptan-6-yl)propan-2-yl)-4-(5-(trifluoromethyl)-1,2,4-oxadiazol-3-yl)benzamide |
| 22 | 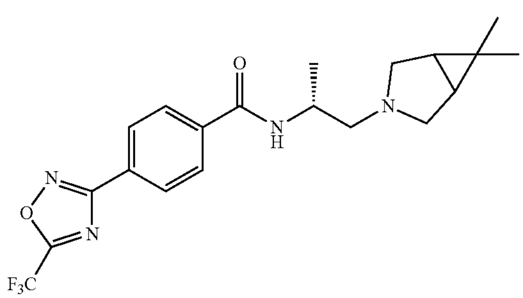 [SMILES: C[C@H](CN1CC2C(C1)C2(C)C)NC(=O)c1ccc(-c2noc(C(F)(F)F)n2)cc1] | N-((2R)-1-(6,6-Dimethyl-3-azabicyclo[3.1.0]hexan-3-yl)propan-2-yl)-4-(5-(trifluoromethyl)-1,2,4-oxadiazol-3-yl)benzamide |
| 23 | 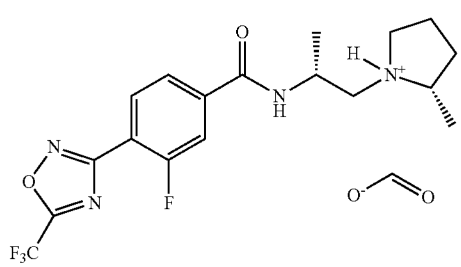 | (2S)-1-((R)-2-(3-Fluoro-4-(5-(trifluoromethyl)-1,2,4-oxadiazol-3-yl)benzamido)propyl)-2-methylpyrrolidin-1-ium formate |

Table of examples

| Example | Structure | IUPAC Name |
|---|---|---|
| 24 | 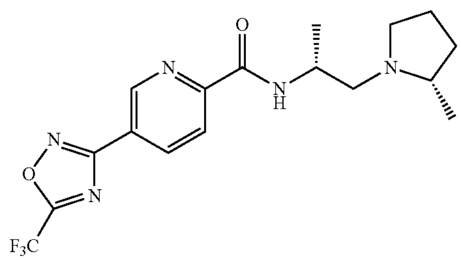 [SMILES: C[C@H](CN1CCC[C@@H]1C)NC(=O)c1ccc(-c2noc(C(F)(F)F)n2)cn1] | N-((R)-1-((S)-2-Methylpyrrolidin-1-yl)propan-2-yl)-5-(5-(trifluoromethyl)-1,2,4-oxadiazol-3-yl)picolinamide |
| 25 | 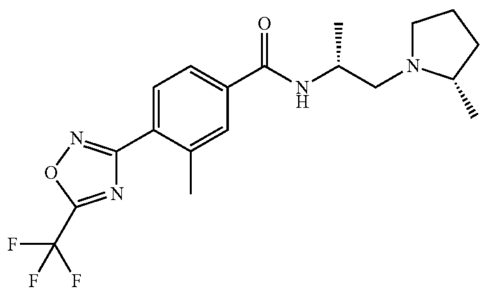 [SMILES: Cc1cc(C(=O)N[C@H](C)CN2CCC[C@@H]2C)ccc1-c1noc(C(F)(F)F)n1] | 3-methyl-N-((R)-1-((S)-2-methylpyrrolidin-1-yl)propan-2-yl)-4-(5-(trifluoromethyl)-1,2,4-oxadiazol-3-yl)benzamide |
| 26 | 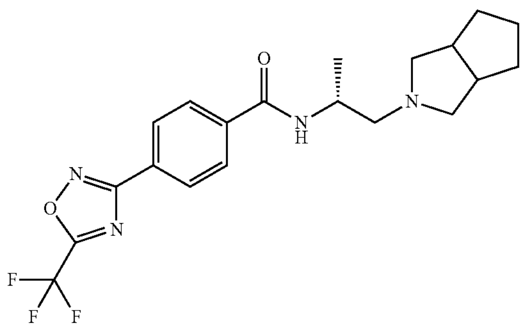 [SMILES: C[C@H](CN1CC2CCCC2C1)NC(=O)c1ccc(-c2noc(C(F)(F)F)n2)cc1] | N-((2R)-1-(hexahydrocyclopenta[c]pyrrol-2(1H)-yl)propan-2-yl)-4-(5-(trifluoromethyl)-1,2,4-oxadiazol-3-yl)benzamide |
| 27 | 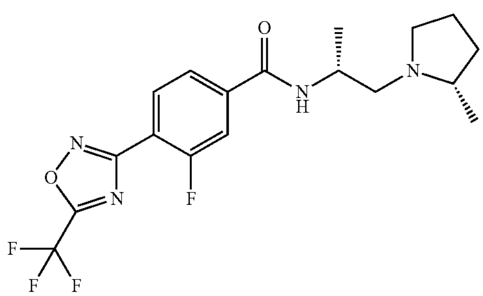 | 3-fluoro-N-((R)-1-((S)-2-methylpyrrolidin-1-yl)propan-2-yl)-4-(5-(trifluoromethyl)-1,2,4-oxadiazol-3-yl)benzamide |

Example 25: Analysis of Inhibition of HDAC4 with Class IIa Histone Deacetylase (HDAC) Inhibitors The potency of Class IIa Histone Deacetylase (HDAC) inhibitors was quantified by measuring the Histone Deacetylase 4 (HDAC4) catalytic domain enzymatic activity using the fluorogenic substrate, Boc-Lys(TFA)-AMC. The substrate was deacetylated to Boc-Lys-AMC by HDAC4. Cleavage by trypsin resulted in the release of the fluorophore AMC from the deacetylated substrate. The fluorescence of the sample was directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) were made by first resuspending the lyophilized compound to a final concentration of 10 mM in 100% dimethyl sulfoxide (DMSO). Stocks of 60 µL aliquots of the 10 mM compound in DMSO were prepared and stored at −20° C. From one stock aliquot of each tested compound and the reference compound, a 16-point serial dilution was prepared according to Table 1 using a 125 µL 16-channel Matrix multi-channel pipette (Matrix Technologies Ltd).

TABLE 1

Serial Dilution of Compounds

| Diluted Solutions | Well | Concentration (μM) | Dilution ratio | Volumes |
|---|---|---|---|---|
| Concentration 1 | A | 10000 | — | 60 μL 10 mM Test compound/reference control |
| Concentration 2 | B | 5000 | 1:2 | 30 μL A + 30 μL DMSO |
| Concentration 3 | C | 2500 | 1:2 | 30 μL B + 30 μL DMSO |
| Concentration 4 | D | 1000 | 1:2.5 | 30 μL C + 45 μL DMSO |
| Concentration 5 | E | 500 | 1:2 | 30 μL D + 30 μL DMSO |
| Concentration 6 | F | 250 | 1:2 | 30 μL E + 30 μL DMSO |
| Concentration 7 | G | 125 | 1:2 | 30 μL F + 30 μL DMSO |
| Concentration 8 | H | 62.5 | 1:2 | 30 μL G + 30 μL DMSO |
| Concentration 9 | I | 31.25 | 1:2 | 30 μL H + 30 μL DMSO |
| Concentration 10 | J | 15.63 | 1:2 | 30 μL I + 30 μL DMSO |
| Concentration 11 | K | 7.81 | 1:2 | 30 μL J + 30 μL DMSO |
| Concentration 12 | L | 3.91 | 1:2 | 30 μL K + 30 μL DMSO |
| Concentration 13 | M | 1.95 | 1:2 | 30 μL L + 30 μL DMSO |
| Concentration 14 | N | 0.98 | 1:2 | 30 μL M + 30 μL DMSO |
| Concentration 15 | O | 0.49 | 1:2 | 30 μL N + 30 μL DMSO |
| Concentration 16 | P | 0.24 | 1:2 | 30 μL O + 30 μL DMSO |

2 μL (200×) of each diluted solution and each control (full activity: 100% DMSO alone or full inhibition 1 mM) was stamped into V-bottomed polypropylene 384-well compound plates using either the Bravo (384-well head from Agilent) or 12.5 μL 16-channel Matrix multi-channel pipette (Matrix Technologies Ltd). Each well with the 200× compound solution was diluted 1:20 by the addition of 38 μL assay buffer+DMSO (10.5% DMSO, 45 mM Tris-HCl, 123 mM NaCl, 2.4 mM KCl, and 0.9 mM MgCl$_2$ at pH 8.0 and equilibrated to r.t.).

Prepare HDAC4 Catalytic Domain Enzyme (0.2 μg/mL).

The HDAC4 catalytic domain enzyme was human catalytic domain HDAC4 protein (amino acids 648-1032) with a C-terminal 6× histidine tag, produced by BioFocus. A working solution of enzyme was prepared from a 500 g/mL stock aliquot of HDAC4 catalytic domain (thawed on ice) diluted to 0.2 μg/mL with assay buffer (50 mM Tris-HCl, 137 mM NaCl, 2.7 mM KCl, and 1 mM MgCl$_2$ at pH 8 and equilibrated to r.t.) just prior to the addition of the enzyme to the assay.

Prepare 5× (50 μM) Boc-Lys(TFA)-AMC Substrate.

5× (50 μM) substrate was prepared just prior to the addition to the assay. A 1 mM substrate stock was made by diluting a 100 mM Boc-Lys(TFA)-AMC in DMSO solution 1:100 by adding it drop-wise to assay buffer (equilibrated to r.t.) while vortexing at slow speed to prevent precipitation. The 5× substrate was prepared by diluting the 1 mM substrate solution 1:20 by adding it drop-wise to assay buffer (equilibrated to r.t.) while vortexing at slow speed to prevent precipitation.

Prepare 3× (30 μM) Developer/Stop Solution.

3× (30 μM) Developer/Stop Solution was prepared just prior to addition to the plate by diluting a stock solution of 10 mM reference compound 1:333 in 25 mg/mL trypsin (PAA Laboratories Ltd.) equilibrated to r.t.

Assay.

5 μL of each solution of 1:20 diluted compound from above was transferred to a clear bottomed, black, 384-well assay plate using the Bravo or the Janus (384-well MDT head from Perkin Elmer). Using a 16-channel Matrix multi-channel pipette, 35 μL of the working solution of HDAC4 catalytic domain enzyme (0.2 μg/mL in assay buffer) was transferred to the assay plate. The assay was then started by adding 10 μL of 5× (50 μM) substrate to the assay plates using either the Bravo, Janus or 16-channel Matrix multi-channel pipette. The assay plate was then shaken for two minutes on an orbital shaker at 900 rpm (rotations per minute). Next the plate was incubated for 15 minutes at 37° C. The reaction was stopped by adding 25 μL of 3× (30 μM) developer/stop solution to the assay plates using either the Bravo, Janus or a 16-channel Matrix multi-channel pipette. Assay plates were then shaken for 5 minutes on an orbital shaker at 1200 rpm. Next, the assay plates were incubated at 37° C. for 1 hour in a tissue culture incubator. Finally, the fluorescence was measured (Excitation: 355 nm, Emission: 460 nm) using PerkinElmer EnVision in top read mode.

Example 26: Analysis of Inhibition of HDAC5 with Class IIa Histone Deacetylase (HDAC) Inhibitors The potency of Class IIa Histone Deacetylase (HDAC) inhibitors is quantified by measuring the Histone Deacetylase 5 (HDAC5) enzymatic activity using the fluorogenic substrate, Boc-Lys(TFA)-AMC. The substrate is deacetylated to Boc-Lys-AMC by HDAC5. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 μL aliquots of the 10 mM compound in DMSO are prepared and stored at −20° C. From one stock aliquot of each compound to be tested and the reference compound, a 16-point serial dilution is prepared according to Table 1 using a 125 μL 16-channel Matrix multi-channel pipette.

2 μL (200×) of each diluted solution and each control (full activity: 100% DMSO alone or full inhibition 1 mM) is stamped into V-bottom polypropylene 384-well compound plates using either Bravo, Janus, or a 12.5 μL 16-channel Matrix multi-channel pipette. Each well with the 2 μL of the 200× stamped compound solution is diluted 1:20 by the addition of 38 μL assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC5 Catalytic Domain Enzyme (0.57 μg/mL).

The HDAC5 catalytic domain enzyme is human HDAC5 catalytic domain (GenBank Accession No. NM_001015053), amino acids 657-1123 with a C-terminal His tag and can be obtained from BPS BioScience. The protein is 51 kDa and is expressed in a baculovirus expression system. A working solution of enzyme is prepared from a 1.65 mg/mL stock aliquot of HDAC5 catalytic domain (thawed on ice) diluted to 0.57 μg/mL with assay buffer (50 mM Tris-HCl, 137 mM NaCl, 2.7 mM KCl, and 1 mM MgCl$_2$ at pH 8 and equilibrated to 37° C.) just prior to the addition of the enzyme to the assay.

Prepare 5× (40 µM) Boc-Lys(TFA)-AMC Substrate.

5× (40 µM) substrate is prepared just prior to the addition to the assay. The 5× substrate is prepared by diluting the 100 mM Boc-Lys(TFA)-AMC in DMSO solution 1:2500 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin equilibrated to 37° C.

Assay.

5 µL of each solution of the 1:20 diluted inhibitor compounds and controls from above is transferred to a clear bottomed, black, 384-well assay plate using the Bravo or Janus. Using a 16-channel Matrix multi-channel pipette, 35 µL of the working solution of the HDAC5 catalytic domain enzyme (0.57 µg/mL in assay buffer) is transferred to the assay plate. The assay is then started by adding 10 µL of 5× (40 µM) substrate to the assay plates using either the Bravo, Janus or 16-channel Matrix multi-channel pipette. The assay plate is then shaken for one minute on an orbital shaker at 900 rpm. Next, the plates are incubated for 15 minutes at 37° C. The reaction is stopped by adding 25 µL of 3× (30 µM) developer/stop solution to the assay plates using either the Bravo, Janus or a 16-channel Matrix multi-channel pipette. Assay plates are then shaken for 2 minutes on an orbital shaker at 900 rpm. Next, the assay plates are incubated at 37° C. for 1 hour in a tissue culture incubator followed by shaking for 1 minute at the maximum rpm on an orbital shaker before reading on the EnVision. Finally, the fluorescence is measured (Excitation: 355 nm, Emission: 460 nm) using PerkinElmer EnVision in top read mode.

Example 27: Analysis of Inhibition of HDAC7 with Class IIa Histone Deacetylase (HDAC) Inhibitors The potency of Class IIa Histone Deacetylase (HDAC) inhibitors is quantified by measuring the Histone Deacetylase 7 (HDAC7) enzymatic activity using the fluorogenic substrate, Boc-Lys(TFA)-AMC. The substrate is deacetylated to Boc-Lys-AMC by HDAC7. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette.

2 µL (200×) of each diluted solution and each control (full activity: 100% DMSO alone or full inhibition 1 mM) is stamped into V-bottom polypropylene 384-well compound plates using either the Bravo, Janus, or a 12.5 µL 16-channel Matrix multi-channel pipette. Each well with the 200× compound solution is diluted 1:20 by the addition of 38 µL assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC7 Enzyme (71 ng/mL).

The HDAC7 enzyme is human HDAC7 (GenBank Accession No. AY302468) amino acids 518-end with a N-terminal Glutathione S-transferase (GST) tag and can be obtained from BPS BioScience. The protein is 78 kDa and is expressed in a baculovirus expression system. A working solution of enzyme is prepared from a 0.5 mg/mL stock aliquot of HDAC7 (thawed on ice) diluted to 71 ng/mL with assay buffer (50 mM Tris-HCl, 137 mM NaCl, 2.7 mM KCl, and 1 mM MgCl$_2$ at pH 8 and equilibrated to 37° C.) just prior to the addition of enzyme to the assay.

Prepare 5× (50 µM)Boc-Lys(TFA)-AMC Substrate.

5× (50 µM) substrate is prepared just prior to the addition to the assay. The 5× substrate is prepared by diluting a 100 mM Boc-Lys(TFA)-AMC in DMSO solution 1:2000 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin equilibrated to 37° C.

Assay.

5 µL of each solution of 1:20 diluted compound from above is transferred to a clear bottomed, black, 384-well assay plate using the Bravo or Janus. Using a 16-channel Matrix multi-channel pipette, 35 µL of the working solution of the HDAC7 enzyme (71 ng/mL in assay buffer) is transferred to the assay plate. The assay is then started by adding 10 µL of 5× (50 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is then stopped by adding 25 µL of 3× (30 µM) developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker. Finally, the fluorescence is measured (Excitation: 355 nm, Emission: 460 nm) using PerkinElmer EnVision in top read mode.

Example 28: Analysis of Inhibition of HDAC9 with Class IIa Histone Deacetylase (HDAC) Inhibitors The potency of Class IIa Histone Deacetylase (HDAC) inhibitors is quantified by measuring the Histone Deacetylase 9 (HDAC9) enzymatic activity using the fluorogenic substrate, Boc-Lys(TFA)-AMC. The substrate is deacetylated to Boc-Lys-AMC by HDAC9. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL aliquots of the 10 mM compound in DMSO are prepared and stored at −20° C.

From one stock aliquot of each compound to be tested and the reference compound, a 16-point serial dilution is prepared according to Table 1 using a 125 µL 16-channel Matrix multi-channel pipette.

2 µL (200×) of each diluted solution and each control (full activity: 100% DMSO alone or full inhibition 1 mM) is stamped into V-bottom polypropylene 384-well compound plates using either the Bravo, Janus, or 12.5 µL 16-channel Matrix multi-channel pipette. Each well with the stamped 200× compound solution is diluted 1:20 by the addition of 38 µL assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC9 Enzyme (0.57 µg/mL).

The HDAC9 enzyme is human HDAC9 (GenBank Accession No. NM_178423) amino acids 604-1066 with a C-terminal His tag and can be obtained from BPS BioScience. The protein is 50.7 kDa and is expressed in a baculovirus expression system. A working solution of enzyme is prepared from a 0.5 mg/mL stock aliquot of HDAC9 (thawed on ice) diluted to 0.57 µg/mL with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (125 µM) Boc-Lys(TFA)-AMC Substrate.

5× (125 µM) substrate is prepared just prior to the addition to the assay. The 5× substrate is prepared by diluting a 100 mM Boc-Lys(TFA)-AMC in DMSO solution 1:800 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin equilibrated to 37° C.

Assay.

5 µL of each solution of 1:20 diluted compound from above is transferred to a clear bottomed, black, 384-well assay plate using the Bravo or Janus. Using a 16-channel Matrix multi-channel pipette, 35 µL of the working solution of the HDAC9 enzyme (0.57 µg/mL in assay buffer) is transferred to the assay plate. The assay is then started by adding 10 µL of 5× (125 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is stopped by adding 25 µL of 3× developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker before reading on the enVision. Finally, the fluorescence is measured (Excitation: 355 nm, Emission: 460 nm) using PerkinElmer EnVision in top read mode.

Example 29: Analysis of Inhibition of Cellular Class IIa HDAC Activity with Class IIa Histone Deacetylase (HDAC) Inhibitors; Cell (Lys-TFA) Substrate The potency of Class IIa Histone Deacetylase (HDAC) inhibitors was quantified by measuring the cellular histone deacetylase enzymatic activity using the fluorogenic substrate, Boc-Lys(TFA)-AMC. After penetration in Jurkat E6-1 cells, the substrate was deacetylated to Boc-Lys-AMC. After cell lysis and cleavage by trypsin, the fluorophore AMC was released from the deacetylated substrate only. The fluorescence of the sample was directly related to the histone deacetylase activity in the sample.

Jurkat E6.1 Cell Culture and Plating.

Jurkat E6.1 cells were cultured according to standard cell culture protocols in Jurkat E6.1 Growth Media (RPMI without phenol red, 10% FBS, 10 mM HEPES, and 1 mM Sodium Pyruvate). Jurkat E6.1 cells were counted using a Coulter Counter and resuspended in Jurkat E6.1 growth media at a concentration of 75,000 cells/35 µL. 35 µL or 75,000 cells was seeded into Greiner microtitre assay plates. The plates were then incubated at 37° C. and 5% $CO_2$ while other assay components were being prepared.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) were made by first resuspending the lyophilized compound to a final concentration of 10 mM in 100% DMSO. Stocks of 70 µL aliquots of the 10 mM compound in DMSO were prepared and stored at −20° C. From one stock aliquot of each tested compound and the reference compound, a 16-point serial dilution was prepared according to Table 1 using a 125 µL 16-channel Matrix multi-channel pipette.

2 µL (200×) of each diluted solution and each control (full activity: 100% DMSO alone or full inhibition 1 mM) was stamped into V-bottom polypropylene 384-well compound plates using either the Bravo, Janus, or 12.5 µL 16-channel Matrix multi-channel pipette. Each well with the 200× compound solution was diluted 1:20 by the addition of 38 µL Jurkat assay buffer+DMSO (9.5% DMSO, RPMI without phenol red, 0.09% FBS, 9 mM Hepes, and 0.9 mM Sodium Pyruvate equilibrated to r.t.)

Prepare 5× (500 µM) Boc-Lys(TFA)-AMC Substrate.

5× (500 µM) substrate was prepared just prior to the addition to the assay. The 5× substrate was prepared by diluting a 100 mM Boc-Lys(TFA)-AMC in DMSO solution 1:200 by adding it drop-wise to Jurkat assay medium (RPMI without phenol red, 0.1% FBS, 10 mM Hepes, and 1 mM Sodium Pyruvate equilibrated to 37° C.) while vortexing at slow speed to prevent precipitation.

Prepare 3× Lysis Buffer.

10 mL of 3× lysis buffer was prepared with 8.8 mL of 3× stock lysis buffer (50 mM Tris-HCl, pH 8.0, 137 mM NaCl, 2.7 mM KCl, 1 mM $MgCl_2$, 1% Nonidet P40 Substitute equilibrated to r.t.) and 1.2 mL of 3 mg/mL Trypsin equilibrated to r.t.

Assay.

5 µL of each solution of 1:20 diluted compound from above was transferred to the Greiner microtitre assay plates with 75,000 cells/well using the Bravo. Cells were then incubated for 2 hours at 37° C. and 5% $CO_2$. The assay was then started by adding 10 µL of 5× (500 µM) substrate to the assay plate using either the Bravo or 16-channel Matrix multi-channel pipette. The cells were then incubated for 3 hours at 37° C. and 5% $CO_2$. Next, 25 µL of 3× lysis buffer was added to each well using either the 125 µL 16 channel pipette or the Bravo. The assay plate was then incubated overnight (15-16 hours) at 37° C. and 5% $CO_2$. The following day, the plates were shaken on an orbital shaker for 1 minute at 900 rpm. Finally the top read fluorescence (Excitation: 355 nm, Emission: 460 nm) was measured using PerkinElmer EnVision.

Example 30: Analysis of Inhibition of Cellular Class I HDAC Activity with Class IIa Histone Deacetylase (HDAC) Inhibitors; Cell (Lys-Ac) Substrate The Class I HDAC activity of Class IIa Histone Deacetylase (HDAC) inhibitors was quantified by measuring the cellular histone deacetylase enzymatic activity using the fluorogenic substrate, Boc-Lys(Ac)-AMC. This was performed according to the procedure in Example 29, using Boc-Lys(Ac)-AMC substrate in place of Boc-Lys(TFA)-AMC.

Using the synthetic methods similar to those described above and the assay protocols described above, the following compounds were synthesized and tested. Examples 1, 17, and 23 in the table below are shown as a formate salt, but it is contemplated that the free base would perform in an equivalent manner in the assays.

| Example | Structure | HDAC4 Biochemical IC$_{50}$ (μM) | Cell (Lys-TFA) IC$_{50}$ (μM) | Cell (Lys-Ac) IC$_{50}$ (μM) |
|---|---|---|---|---|
| 1 | 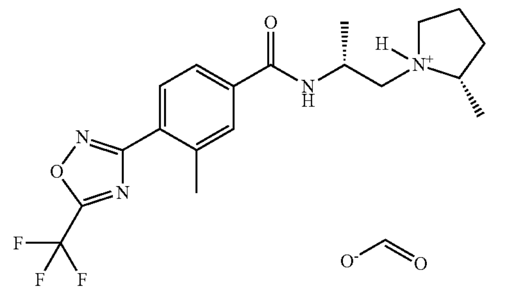 | 0.10 | 1.6 | >50 |
| 2 | 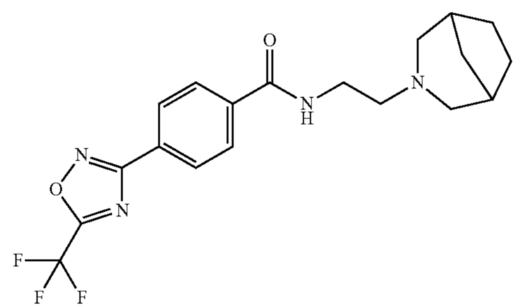 [SMILES: O=C(NCCN1CC2CCC(C2)C1)c1ccc(-c2noc(C(F)(F)F)n2)cc1] | 0.14 | 0.33 | 4.9 |
| 3 | 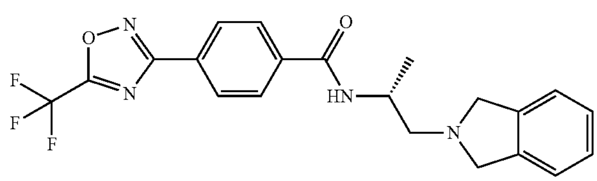 [SMILES: C[C@H](CN1Cc2ccccc2C1)NC(=O)c1ccc(-c2noc(C(F)(F)F)n2)cc1] | 0.039 | 0.14 | 4.9 |
| 4 | 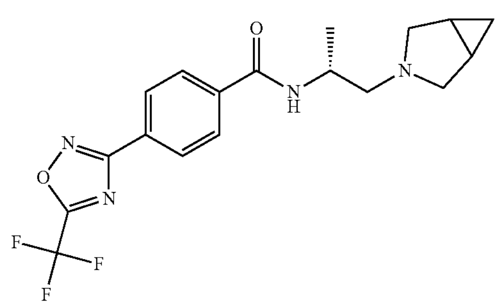 [SMILES: C[C@H](CN1CC2CC2C1)NC(=O)c1ccc(-c2noc(C(F)(F)F)n2)cc1] | 0.008 | 0.051 | 6.9 |

-continued

| Example | Structure | HDAC4 Biochemical IC$_{50}$ (μM) | Cell (Lys-TFA) IC$_{50}$ (μM) | Cell (Lys-Ac) IC$_{50}$ (μM) |
| --- | --- | --- | --- | --- |
| 5 | 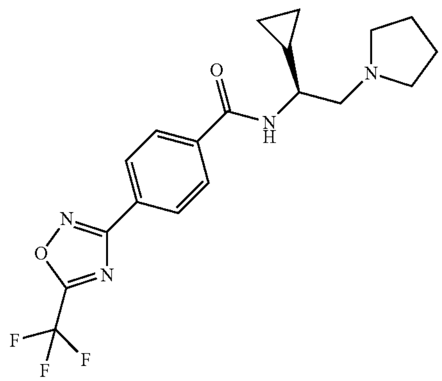 [SMILES: O=C(N[C@H](CN1CCCC1)C1CC1)c1ccc(-c2noc(C(F)(F)F)n2)cc1] | 0.048 | 0.71 | 25.7 |
| 6 | 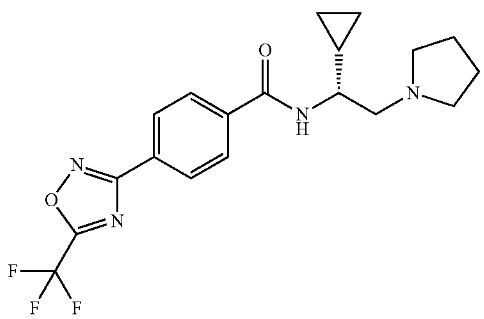 [SMILES: O=C(N[C@@H](CN1CCCC1)C1CC1)c1ccc(-c2noc(C(F)(F)F)n2)cc1] | 0.077 | 0.75 | >50 |
| 7 | 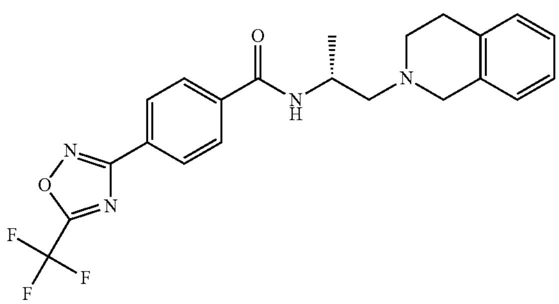 [SMILES: C[C@H](CN1CCc2ccccc2C1)NC(=O)c1ccc(-c2noc(C(F)(F)F)n2)cc1] | 0.009 | 0.018 | 2.4 |
| 8 | 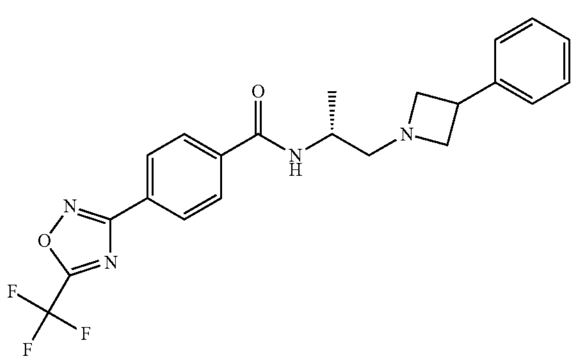 [SMILES: C[C@H](CN1CC(c2ccccc2)C1)NC(=O)c1ccc(-c2noc(C(F)(F)F)n2)cc1] | 0.014 | 0.039 | 0.71 |

| Example | Structure | HDAC4 Biochemical IC$_{50}$ (μM) | Cell (Lys-TFA) IC$_{50}$ (μM) | Cell (Lys-Ac) IC$_{50}$ (μM) |
|---|---|---|---|---|
| 9 | 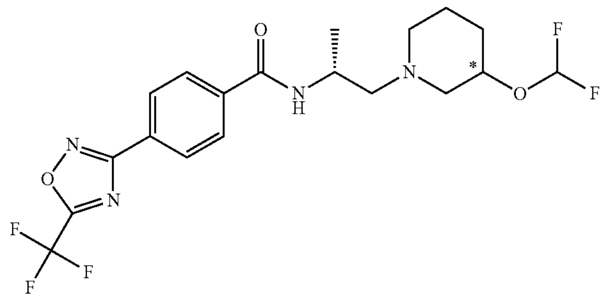 [SMILES: C[C@H](CN1CCCC(OC(F)F)C1)NC(=O)c1ccc(-c2noc(C(F)(F)F)n2)cc1] | 0.021 | 0.057 | 3.7 |
| 10 | 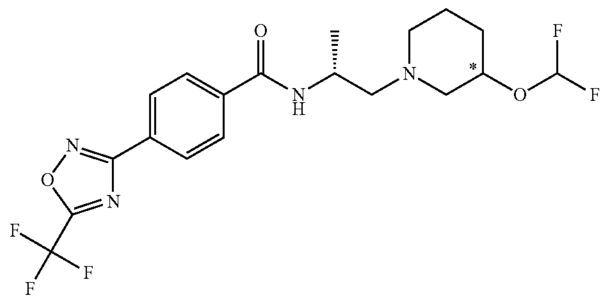 [SMILES: C[C@H](CN1CCCC(OC(F)F)C1)NC(=O)c1ccc(-c2noc(C(F)(F)F)n2)cc1] | 0.003 | 0.007 | 1.5 |
| 11 | 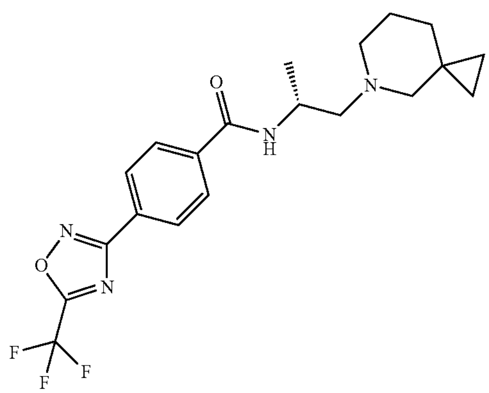 [SMILES: C[C@H](CN1CCCC2(CC2)C1)NC(=O)c1ccc(-c2noc(C(F)(F)F)n2)cc1] | 0.003 | 0.009 | 0.97 |
| 12 | 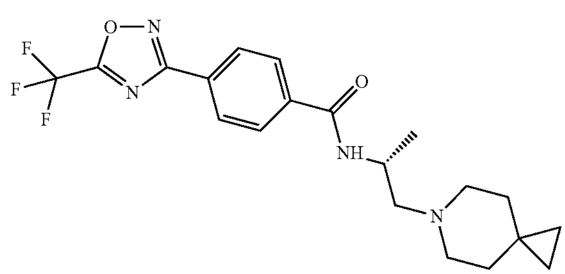 [SMILES: C[C@H](CN1CCC2(CC1)CC2)NC(=O)c1ccc(-c2noc(C(F)(F)F)n2)cc1] | 0.030 | 0.058 | 4.0 |
| 13 | 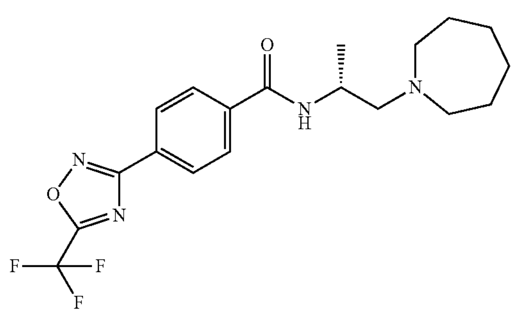 [SMILES: C[C@H](CN1CCCCCC1)NC(=O)c1ccc(-c2noc(C(F)(F)F)n2)cc1] | 0.011 | 0.030 | 1.7 |

-continued

| Example | Structure | HDAC4 Biochemical IC$_{50}$ (μM) | Cell (Lys-TFA) IC$_{50}$ (μM) | Cell (Lys-Ac) IC$_{50}$ (μM) |
| --- | --- | --- | --- | --- |
| 14 | 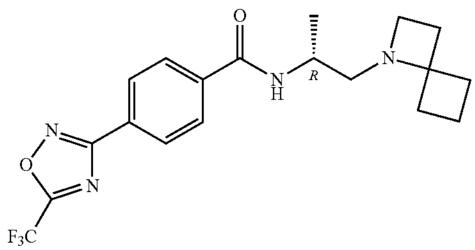 | 0.016 | 0.18 | 7.7 |
| 15 | 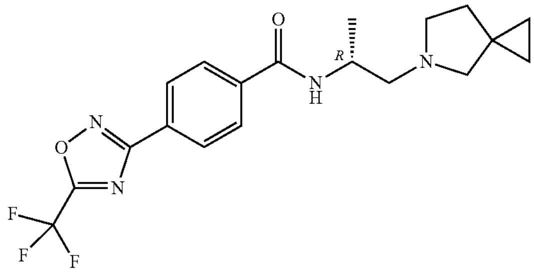 | 0.008 | 0.069 | 5.1 |
| 16 | 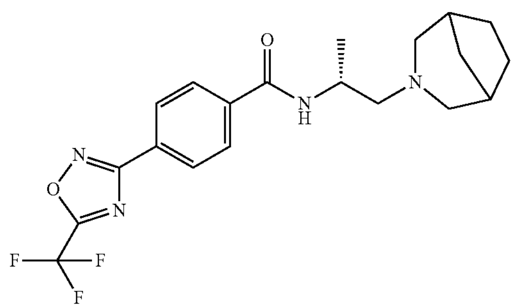 [SMILES: C[C@H](CN1CC2CCC(C2)C1)NC(=O)c1ccc(-c2noc(C(F)(F)F)n2)cc1] | 0.007 | 0.012 | 0.89 |
| 17 | 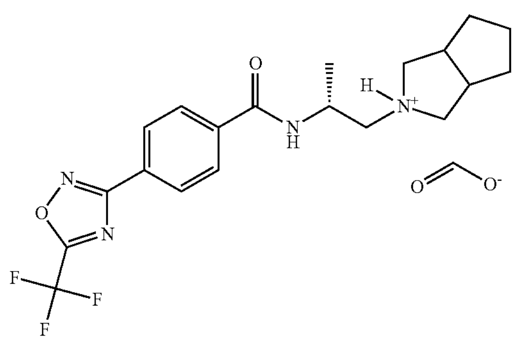 | 0.012 | 0.028 | 0.69 |
| 18 | 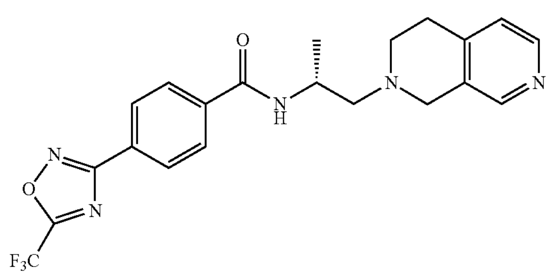 [SMILES: C[C@H](CN1CCc2ccncc2C1)NC(=O)c1ccc(-c2noc(C(F)(F)F)n2)cc1] | 0.006 | 0.19 | 12.7 |

-continued
| Example | Structure | HDAC4 Biochemical IC$_{50}$ (µM) | Cell (Lys-TFA) IC$_{50}$ (µM) | Cell (Lys-Ac) IC$_{50}$ (µM) |
|---|---|---|---|---|
| 19 | 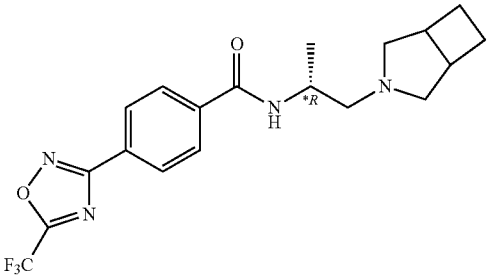 [SMILES: C[C@H](CN1CC2CCC2C1)NC(=O)c1ccc(-c2noc(C(F)(F)F)n2)cc1] | 0.004 | 0.009 | 1.1 |
| 20 | 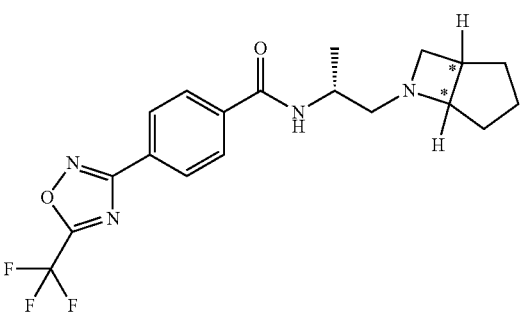 [SMILES: C[C@H](CN1CC2CCCC21)NC(=O)c1ccc(-c2noc(C(F)(F)F)n2)cc1] | 0.022 | 0.15 | 7.8 |
| 21 | 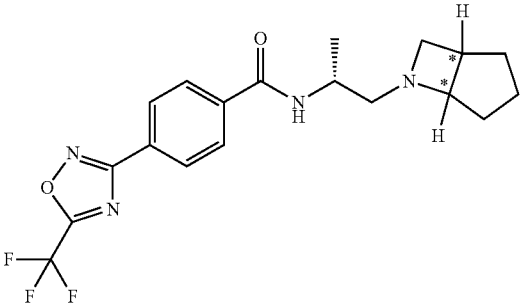 [SMILES: C[C@H](CN1CC2CCCC21)NC(=O)c1ccc(-c2noc(C(F)(F)F)n2)cc1] | 0.004 | 0.016 | 3.1 |
| 22 | 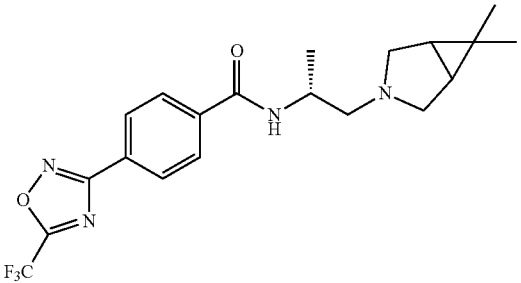 [SMILES: C[C@H](CN1CC2C(C1)C2(C)C)NC(=O)c1ccc(-c2noc(C(F)(F)F)n2)cc1] | 0.020 | 0.086 | 6.1 |
| 23 | 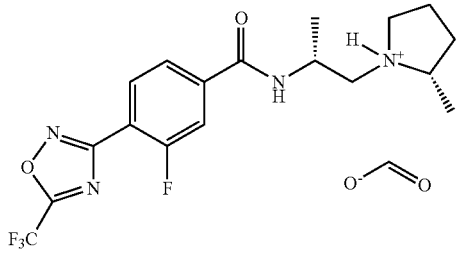 | 0.009 | 0.072 | 21.4 |

| Example | Structure | HDAC4 Biochemical IC$_{50}$ (µM) | Cell (Lys-TFA) IC$_{50}$ (µM) | Cell (Lys-Ac) IC$_{50}$ (µM) |
|---|---|---|---|---|
| 24 | 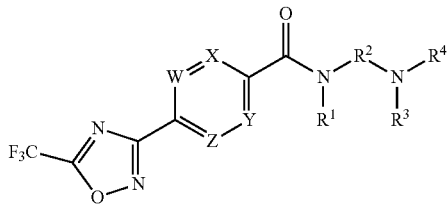 | 0.134 | 1.03 | 33.7 |

REFERENCES

1) Bioorganic & Medicinal Chemistry Letters 17 (2007) 6476-6480

While some embodiments have been shown and described, various modifications and substitutions may be made thereto without departing from the spirit and scope of the disclosure. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present disclosure has been described by way of illustration and not limitations on the scope of the claims.

What is claimed:

1. A compound of Formula I:

Formula I or a pharmaceutically acceptable salt, an optical isomer, or a mixture of optical isomers thereof;
wherein:
W is N or CR$^5$; X is N or CR$^6$; Y is N or CR$^7$; and Z is N or CR$^8$; provided not more than two of W, X, Y, and Z are N;
R$^1$ is selected from H and C$_1$-C$_3$ alkyl;
R$^2$ is C$_2$-C$_3$ alkylene optionally substituted with C$_1$-C$_2$ haloalkyl or 3 or 4-membered cycloalkyl;
R$^3$ and R$^4$, together with the nitrogen atom to which they are attached, form:
  a 4 or 7-membered heteromonocyclic group optionally substituted with one to five substituents independently selected from: C$_1$-C$_3$ alkoxy, C$_1$-C$_3$ alkyl, C$_1$-C$_3$ haloalkoxy, C$_1$-C$_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents independently selected from C$_1$-C$_3$ alkyl, C$_1$-C$_3$ haloalkyl, and halo; or
  a 5 or 6-membered heteromonocyclic group optionally substituted with one to five substituents independently selected from: C$_1$-C$_3$ alkoxy, C$_1$-C$_3$ alkyl, C$_1$-C$_3$ haloalkoxy, C$_1$-C$_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents each independently selected from C$_1$-C$_3$ alkyl, C$_1$-C$_3$ haloalkyl, and halo; or
  a 6, 7, 8, 9, or 10-membered heterobicyclic group, which is optionally substituted with one to five substituents independently selected from: C$_1$-C$_3$ alkoxy, C$_1$-C$_3$ alkyl, C$_1$-C$_3$ haloalkoxy, C$_1$-C$_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents independently selected from C$_1$-C$_3$ alkyl, C$_1$-C$_3$ haloalkyl, and halo;
R$^5$, R$^6$, R$^7$ and R$^8$ are each independently selected from H, C$_1$-C$_4$ alkyl, C$_1$-C$_4$ haloalkyl, and halo;
provided that if R$^3$ and R$^4$, together with the nitrogen atom to which they are attached, form a 5 or 6-membered heteromonocyclic group, then:
  R$^2$ is C$_2$-C$_3$ alkylene substituted with C$_1$-C$_2$ haloalkyl or 3 or 4-membered cycloalkyl.

2. A compound according to claim 1, or a pharmaceutically acceptable salt, an optical isomer, or a mixture of optical isomers thereof, wherein the compound is of Formula II:

Formula II

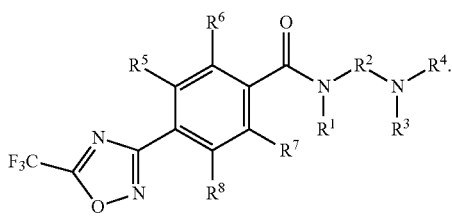

3. A compound according to claim 1, or a pharmaceutically acceptable salt, an optical isomer, or a mixture of optical isomers thereof, wherein $R^2$ is $C_2$-$C_3$ alkylene optionally substituted with 3 or 4-membered cycloalkyl.

4. A compound of Formula III:

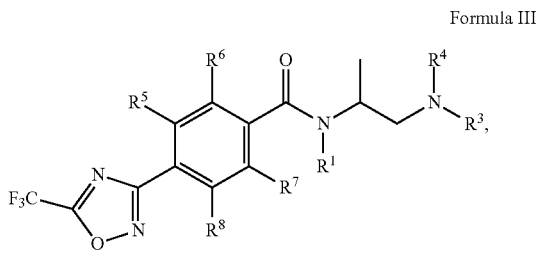

Formula III or a pharmaceutically acceptable salt, an optical isomer, or a mixture of optical isomers thereof, wherein:
$R^1$, $R^5$, $R^6$, $R^7$ and $R^8$ are each H; and
$R^3$ and $R^4$, together with the nitrogen atom to which they are attached, form a 5 or 6-membered heteromonocyclic group substituted with one to two substituents each independently selected from 3 or 4-membered cycloalkyl and heteroaryl.

5. A compound according to claim 1, or a pharmaceutically acceptable salt, an optical isomer, or a mixture of optical isomers thereof, wherein $R^6$ is H.

6. A compound according to claim 1, or a pharmaceutically acceptable salt, an optical isomer, or a mixture of optical isomers thereof, wherein the compound is of Formula V:

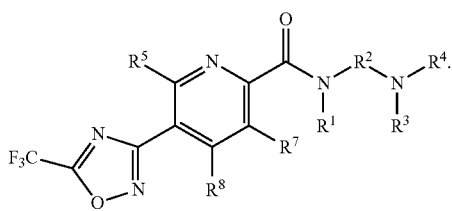

Formula V

7. A compound according to claim 6, or a pharmaceutically acceptable salt, an optical isomer, or a mixture of optical isomers thereof, wherein $R^2$ is $C_2$-$C_3$ alkylene optionally substituted with 3 or 4-membered cycloalkyl.

8. A compound according to claim 7, or a pharmaceutically acceptable salt, an optical isomer, or a mixture of optical isomers thereof, wherein the compound is of Formula VI:

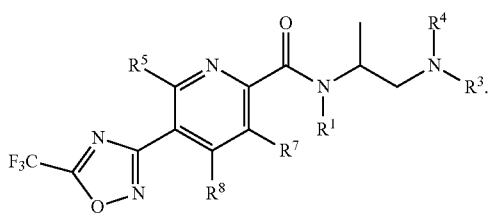

Formula VI

9. A compound according to claim 1, or a pharmaceutically acceptable salt, an optical isomer, or a mixture of optical isomers thereof, wherein $R^5$ is H.

10. A compound according to claim 1, or a pharmaceutically acceptable salt, an optical isomer, or a mixture of optical isomers thereof, wherein $R^7$ is H.

11. A compound according to claim 1, or a pharmaceutically acceptable salt, an optical isomer, or a mixture of optical isomers thereof, wherein $R^8$ is selected from H, halo, and methyl.

12. A compound according to claim 1, or a pharmaceutically acceptable salt, an optical isomer, or a mixture of optical isomers thereof, wherein $R^1$ is selected from H and methyl.

13. A compound according to claim 12, or a pharmaceutically acceptable salt, an optical isomer, or a mixture of optical isomers thereof, wherein $R^1$ is H.

14. A compound according to claim 1, or a pharmaceutically acceptable salt, an optical isomer, or a mixture of optical isomers thereof, wherein $R^3$ and $R^4$, together with the nitrogen atom to which they are attached, form a 4 or 7-membered heteromonocyclic group selected from 3-phenylazetidin-1-yl, and azepan-1-yl.

15. A compound according to claim 1, or a pharmaceutically acceptable salt, an optical isomer, or a mixture of optical isomers thereof, wherein $R^3$ and $R^4$, together with the nitrogen atom to which they are attached, form a 5 or 6-membered heteromonocyclic group optionally substituted with one to five substituents independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, aryl, and heteroaryl, wherein aryl and heteroaryl are optionally further substituted with one to five substituents independently selected from $C_1$-$C_3$ alkyl, $C_1$-$C_3$ haloalkyl, and halo.

16. A compound according to claim 1, or a pharmaceutically acceptable salt, an optical isomer, or a mixture of optical isomers thereof, wherein $R^3$ and $R^4$, together with the nitrogen atom to which they are attached, form a 5 or 6-membered heteromonocyclic group optionally substituted with one to five substituents independently selected from: $C_1$-$C_3$ alkyl, $C_1$-$C_3$ haloalkoxy, and aryl, wherein aryl is optionally further substituted with one to five substituents independently selected from $C_1$-$C_3$ alkyl, $C_1$-$C_3$ haloalkyl, and halo.

17. A compound according to claim 1, or a pharmaceutically acceptable salt, an optical isomer, or a mixture of optical isomers thereof, wherein $R^3$ and $R^4$, together with the nitrogen atom to which they are attached, form a 5 or 6-membered heteromonocyclic group optionally substituted with one to five substituents independently selected from: $C_1$-$C_3$ alkyl, $C_1$-$C_3$ haloalkoxy, and phenyl, wherein phenyl is optionally further substituted with one to five substituents independently selected from $C_1$-$C_3$ alkyl, $C_1$-$C_3$ haloalkyl, and halo.

18. A compound according to claim 1, or a pharmaceutically acceptable salt, an optical isomer, or a mixture of optical isomers thereof, wherein $R^3$ and $R^4$, together with the nitrogen atom to which they are attached, form a 5 or 6-membered heteromonocyclic group optionally substituted with one to five substituents independently selected from: methyl, difluoromethoxy, and phenyl.

19. A compound according to claim 1, or a pharmaceutically acceptable salt, an optical isomer, or a mixture of optical isomers thereof, wherein $R^3$ and $R^4$, together with the nitrogen atom to which they are attached, form a 5 or 6-membered heteromonocyclic group selected from pyrrolidin-1-yl, and piperidin-1-yl, each of which is optionally substituted with one substituent selected from: methyl, difluoromethoxy, and phenyl.

20. A compound according to claim 1, or a pharmaceutically acceptable salt, an optical isomer, or a mixture of optical isomers thereof, wherein $R^3$ and $R^4$, together with the nitrogen atom to which they are attached, form a 5 or 6-membered heteromonocyclic group selected from
pyrrolidin-1-yl,
2-methyl-pyrrolidin-1-yl, and
3-(difluoromethoxy)piperidin-1-yl.

21. A compound according to claim 4, or a pharmaceutically acceptable salt, an optical isomer, or a mixture of optical isomers therof, wherein $R^3$ and $R^4$, together with the nitrogen atom to which they are attached, form a 5-membered heteromonocyclic group substituted with one 3 or 4-membered cycloalkyl.

22. A compound according to claim 4, or a pharmaceutically acceptable salt, an optical isomer, or a mixture of optical isomers therof, wherein $R^3$ and $R^4$, together with the nitrogen atom to which they are attached, form a 5-membered heteromonocyclic group substituted with one heteroaryl.

23. A compound according to claim 1, or a pharmaceutically acceptable salt, an optical isomer, or a mixture of optical isomers thereof, wherein $R^5$ is $C_1$-$C_4$ alkyl or halo.

24. A compound according to claim 1, or a pharmaceutically acceptable salt, an optical isomer, or a mixture of optical isomers thereof, wherein $R^8$ is $C_1$-$C_4$ alkyl or halo.

25. A compound according to claim 1, or a pharmaceutically acceptable salt, an optical isomer, or a mixture of optical isomers thereof, wherein W is N.

26. A compound according to claim 1, or a pharmaceutically acceptable salt, an optical isomer, or a mixture of optical isomers thereof, wherein Z is N.

27. A compound according to claim 1, or a pharmaceutically acceptable salt, an optical isomer, or a mixture of optical isomers thereof, wherein $R^3$ and $R^4$, together with the nitrogen atom to which they are attached, form a 6, 7, or 8-membered heterobicyclic group, which is optionally substituted with one to five substituents independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents independently selected from $C_1$-$C_3$ alkyl, $C_1$-$C_3$ haloalkyl, and halo.

28. A compound according to claim 1, or a pharmaceutically acceptable salt, an optical isomer, or a mixture of optical isomers thereof, wherein $R^3$ and $R^4$, together with the nitrogen atom to which they are attached, form a 6, 7, 8, 9, or 10-membered heterobicyclic group selected from:
1-azaspiro[3.3]heptan-1-yl,
3-azabicyclo[3.1.0]hexan-3-yl,
3-azabicyclo[3.2.0]heptan-3-yl,
3-azabicyclo[3.2.1]heptan-3-yl,
3-azabicyclo[3.2.1]octan-3-yl,
3,4-dihydroisoquinolin-2(1H)-yl,
3,4-dihydro-2,7-naphthyridin-2(1H)-yl,
5-azaspiro[2.4]heptan-5-yl,
5-azaspiro[2.5]octan-5-yl,
6-azaspiro[2.5]octan-6-yl,
1-azaspiro[3.3]heptan-1-yl,
6-azabicyclo[3.2.0]heptan-6-yl,
isoindolin-2-yl, and
octahydrocyclopenta[c]pyrrol-2-yl,
each of which is optionally substituted with one to five substituents independently selected from: $C_1$-$C_3$ alkoxy, $C_1$-$C_3$ alkyl, $C_1$-$C_3$ haloalkoxy, $C_1$-$C_3$ haloalkyl, 3 or 4-membered cycloalkoxy, 3 or 4-membered cycloalkyl, 3 or 4-membered heterocycloalkyl, carboxy, aryl, cyano, halo, and heteroaryl, wherein aryl and heteroaryl are optionally further substituted with one to five substituents independently selected from $C_1$-$C_3$ alkyl, $C_1$-$C_3$ haloalkyl, and halo.

29. A compound according to claim 1, or a pharmaceutically acceptable salt, an optical isomer, or a mixture of optical isomers thereof, wherein $R^3$ and $R^4$, together with the nitrogen atom to which they are attached, form a 6, 7, 8, 9, or 10-membered heterobicyclic group selected from:
1-azaspiro[3.3]heptan-1-yl,
3-azabicyclo[3.1.0]hexan-3-yl,
3-azabicyclo[3.2.0]heptan-3-yl,
3-azabicyclo[3.2.1]heptan-3-yl,
3-azabicyclo[3.2.1]octan-3-yl,
3,4-dihydroisoquinolin-2(1H)-yl,
3,4-dihydro-2,7-naphthyridin-2(1H)-yl,
5-azaspiro[2.4]heptan-5-yl,
5-azaspiro[2.5]octan-5-yl,
6-azaspiro[2.5]octan-6-yl,
1-azaspiro[3.3]heptan-1-yl,
6-azabicyclo[3.2.0]heptan-6-yl,
isoindolin-2-yl, and
octahydrocyclopenta[c]pyrrol-2-yl,
each of which is optionally substituted with one or two substituents independently selected from: $C_1$-$C_3$ alkoxy, $C_1$-$C_3$ alkyl, $C_1$-$C_3$ haloalkoxy, $C_1$-$C_3$ haloalkyl, and carboxy.

30. A compound according to claim 1, or a pharmaceutically acceptable salt, an optical isomer, or a mixture of optical isomers thereof, wherein $R^3$ and $R^4$, together with the nitrogen atom to which they are attached, form a 6, 7, 8, 9, or 10-membered heterobicyclic group selected from:
1-azaspiro[3.3]heptan-1-yl,
3-azabicyclo[3.1.0]hexan-3-yl,
3-azabicyclo[3.2.0]heptan-3-yl,
3-azabicyclo[3.2.1]heptan-3-yl,
3-azabicyclo[3.2.1]octan-3-yl,
3,4-dihydroisoquinolin-2(1H)-yl,
3,4-dihydro-2,7-naphthyridin-2(1H)-yl,
5-azaspiro[2.4]heptan-5-yl,
5-azaspiro[2.5]octan-5-yl,
6-azaspiro[2.5]octan-6-yl,
1-azaspiro[3.3]heptan-1-yl,
6-azabicyclo[3.2.0]heptan-6-yl,
isoindolin-2-yl, and
octahydrocyclopenta[c]pyrrol-2-yl,
each of which is optionally substituted with one or two substituents independently selected from $C_1$-$C_3$ alkyl.

31. A compound of formula:

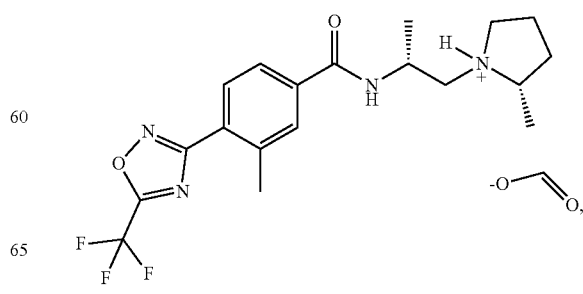

103
-continued
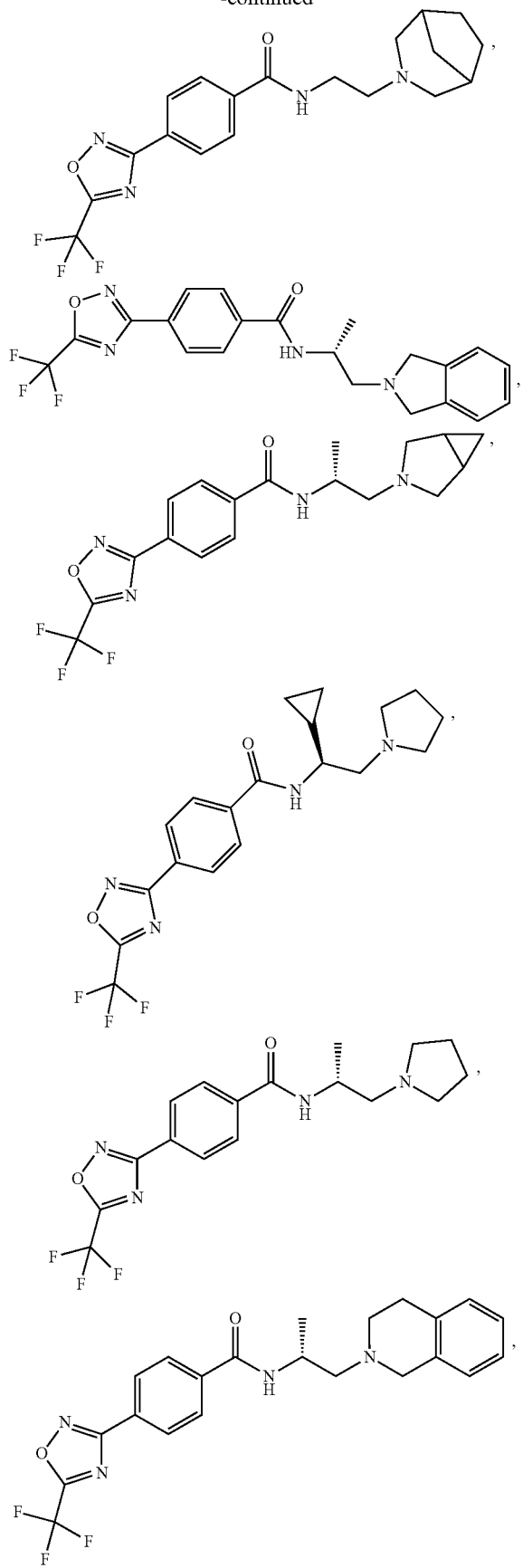
104
-continued
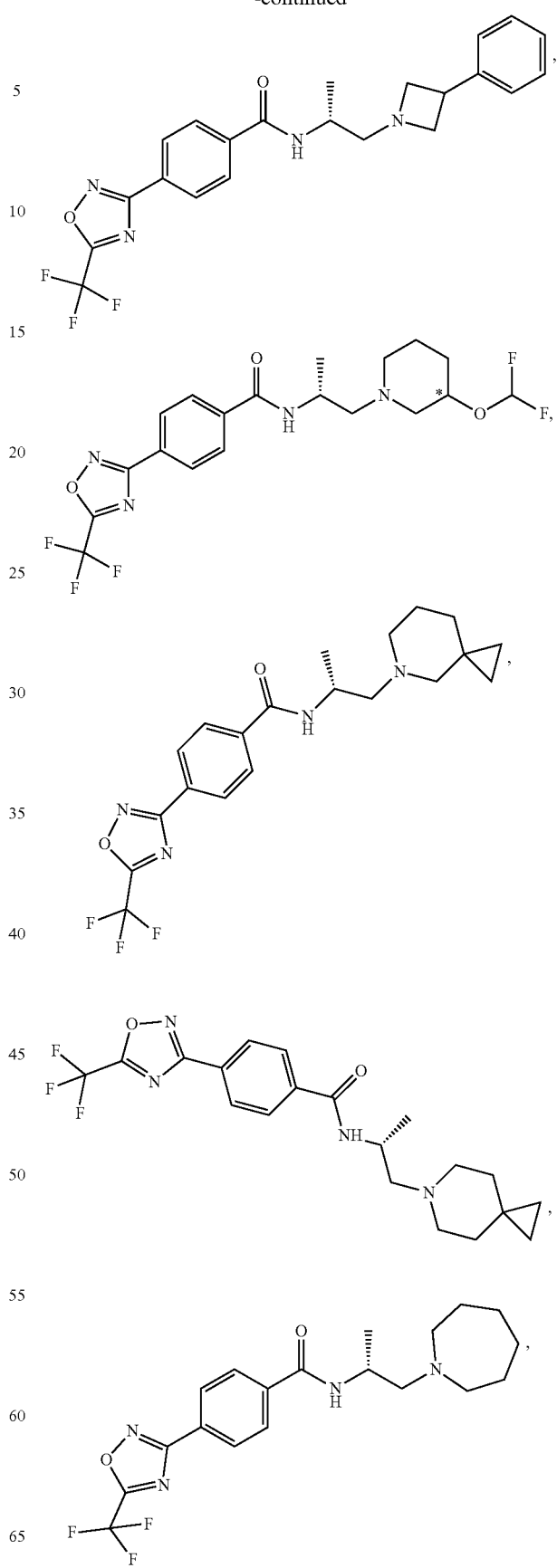

105
-continued
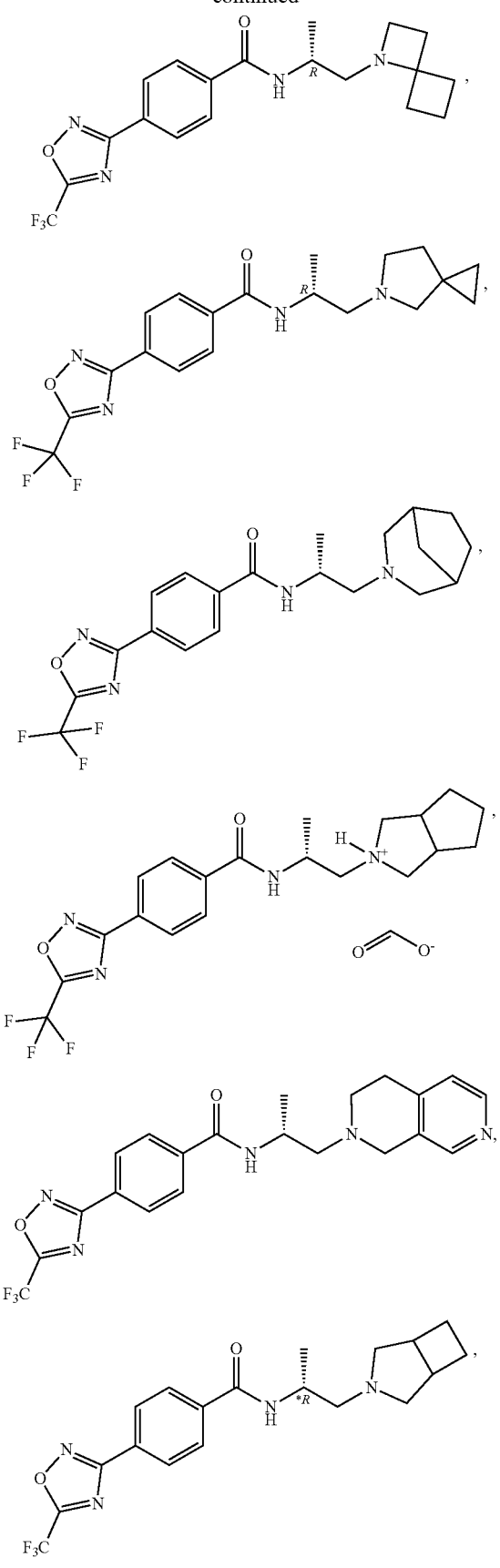
106
-continued
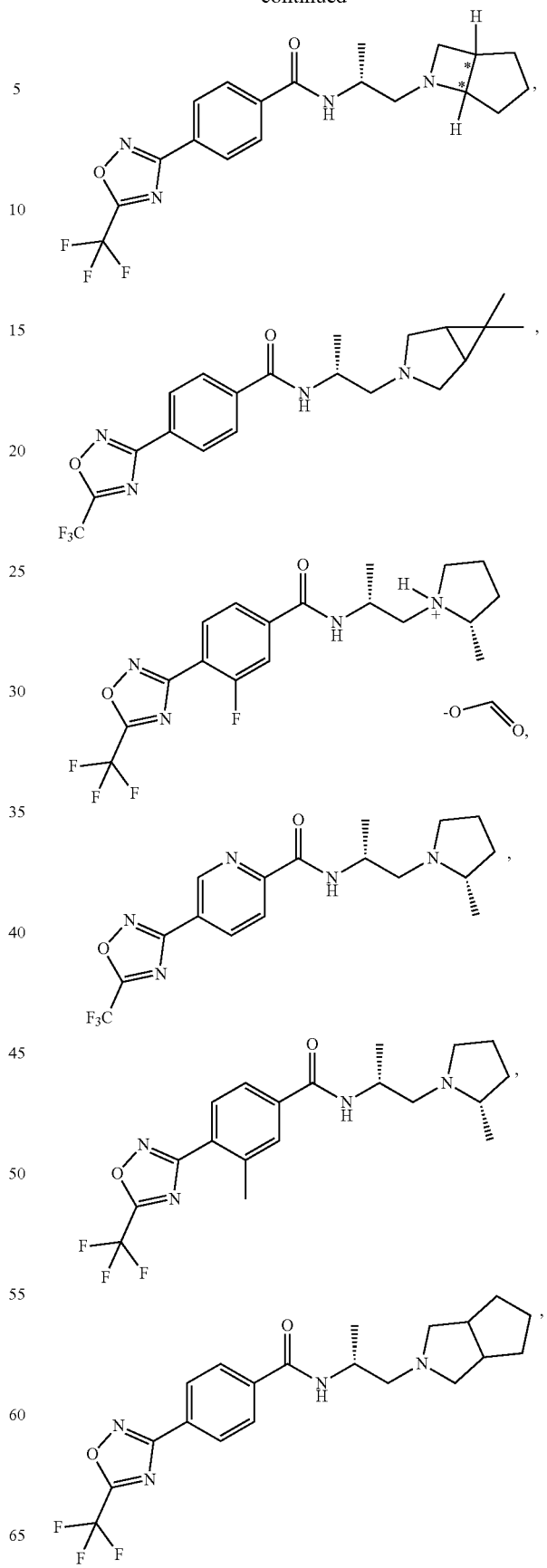

-continued
or

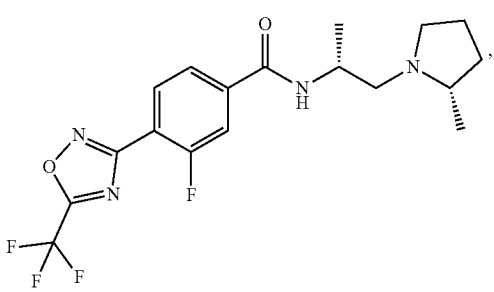

32. A pharmaceutical composition comprising a compound according to claim 1 or a pharmaceutically acceptable salt, an optical isomer, or a mixture of optical isomers thereof and a pharmaceutically acceptable carrier.

33. A process for preparing a pharmaceutical composition comprising admixing a compound according to claim 1 or a pharmaceutically acceptable salt, an optical isomer, or a mixture of optical isomers thereof and a pharmaceutically acceptable carrier.

34. A method for treating a patient suffering from Huntington's disease, wherein the method comprises administering to the patient a compound according to claim 1, or a pharmaceutically acceptable salt, an optical isomer, or a mixture of optical isomers thereof.

35. A method for treating a patient suffering from Huntington's disease, wherein the method comprises administering to the patient a compound according to claim 4, or a pharmaceutically acceptable salt, an optical isomer, or a mixture of optical isomers thereof.

36. A method for treating a patient suffering from Huntington's disease, wherein the method comprises administering to the patient a compound according to claim 31, or a pharmaceutically acceptable salt, an optical isomer, or a mixture of optical isomers thereof.

\* \* \* \* \*